US009226825B2

(12) United States Patent
Starksen et al.

(10) Patent No.: US 9,226,825 B2
(45) Date of Patent: *Jan. 5, 2016

(54) DELIVERY DEVICES AND METHODS FOR HEART VALVE REPAIR

(75) Inventors: Niel F. Starksen, Los Altos Hills, CA (US); John To, Newark, CA (US); Mariel Fabro, San Jose, CA (US); Michael F. Wei, Redwood City, CA (US); Rodolfo A. Morales, Los Gatos, CA (US)

(73) Assignee: Guided Delivery Systems, Inc., Santa Clara, CA (US)

( * ) Notice: Subject to any disclaimer, the term of this patent is extended or adjusted under 35 U.S.C. 154(b) by 2266 days.

This patent is subject to a terminal disclaimer.

(21) Appl. No.: 10/901,554

(22) Filed: Jul. 27, 2004

(65) Prior Publication Data

US 2005/0107812 A1      May 19, 2005

Related U.S. Application Data

(63) Continuation-in-part of application No. 10/792,681, filed on Mar. 2, 2004, now abandoned, which is a continuation-in-part of application No. 10/741,130, filed on Dec. 19, 2003, now Pat. No. 8,287,555, and a (Continued)

(51) Int. Cl.
*A61F 2/24* (2006.01)
*A61B 17/00* (2006.01)
(Continued)

(52) U.S. Cl.
CPC .......... *A61F 2/2436* (2013.01); *A61B 17/00234* (2013.01); *A61B 17/0401* (2013.01);
(Continued)

(58) Field of Classification Search
CPC ... A61F 2/2427; A61F 2/2442; A61F 2/2454; A61B 17/0401; A61B 2017/0409

USPC .......................................... 606/143; 128/898
See application file for complete search history.

(56) References Cited

U.S. PATENT DOCUMENTS 2,108,206 A    2/1938  Meeker
3,656,185 A    4/1972  Carpentier
(Continued)

FOREIGN PATENT DOCUMENTS

EP    0 363 661 A1    4/1990
EP    0 669 101 A1    8/1995
(Continued)

OTHER PUBLICATIONS

Non-Final Office Action mailed Jan. 9, 2008, for U.S. Appl. No. 11/232,190, filed Sep. 20, 2005, 8 pages.
(Continued)

*Primary Examiner* — Diane Yabut
(74) *Attorney, Agent, or Firm* — Morrison & Foerster LLP

(57) ABSTRACT

Devices, systems and methods facilitate positioning of a cardiac valve annulus treatment device, thus enhancing treatment of the annulus. Methods generally involve advancing an anchor delivery device through vasculature of the patient to a location in the heart for treating the valve annulus, contacting the anchor delivery device with a length of the valve annulus, delivering a plurality of coupled anchors from the anchor delivery device to secure the anchors to the annulus, and drawing the anchors together to circumferentially tighten the valve annulus. Devices generally include an elongate catheter having at least one tensioning member and at least one tensioning actuator for deforming a distal portion of the catheter to help it conform to a valve annulus. The catheter device may be used to navigate a subannular space below a mitral valve to facilitate positioning of an anchor delivery device.

47 Claims, 33 Drawing Sheets

Related U.S. Application Data continuation-in-part of application No. 10/656,797, filed on Sep. 4, 2003, now Pat. No. 7,753,922, and a continuation-in-part of application No. 10/461,043, filed on Jun. 13, 2003, now Pat. No. 6,986,775.

(60) Provisional application No. 60/459,735, filed on Apr. 1, 2003, provisional application No. 60/524,922, filed on Nov. 24, 2003, provisional application No. 60/388,935, filed on Jun. 13, 2002, provisional application No. 60/429,288, filed on Nov. 25, 2002, provisional application No. 60/445,890, filed on Feb. 6, 2003, provisional application No. 60/462,502, filed on Apr. 10, 2003.

(51) Int. Cl.
*A61B 17/04* (2006.01)
*A61B 17/064* (2006.01)
*A61B 17/068* (2006.01)
*A61B 17/29* (2006.01)

(52) U.S. Cl.
CPC ............ *A61B17/064* (2013.01); *A61B 17/068* (2013.01); *A61B 17/0643* (2013.01); *A61B 17/0644* (2013.01); *A61B 17/0682* (2013.01); *A61F 2/2445* (2013.01); *A61F 2/2466* (2013.01); *A61B 2017/00243* (2013.01); *A61B 2017/00783* (2013.01); *A61B 2017/00867* (2013.01); *A61B 2017/0409* (2013.01); *A61B 2017/0414* (2013.01); *A61B 2017/0443* (2013.01); *A61B 2017/0496* (2013.01); *A61B 2017/2905* (2013.01)

(56) References Cited

U.S. PATENT DOCUMENTS

| | | |
|---|---|---|
| 3,727,614 A | 4/1973 | Kniazuk |
| 3,773,034 A | 11/1973 | Burns et al. |
| 3,961,419 A | 6/1976 | Schwartz |
| 3,976,079 A | 8/1976 | Samuels et al. |
| 4,014,492 A | 3/1977 | Rothfuss |
| 4,034,473 A | 7/1977 | May |
| 4,042,979 A | 8/1977 | Angell |
| 4,043,504 A | 8/1977 | Hueil et al. |
| 4,053,979 A | 10/1977 | Tuthill et al. |
| 4,055,861 A | 11/1977 | Carpentier et al. |
| 4,069,825 A | 1/1978 | Akiyama |
| 4,290,151 A | 9/1981 | Massana |
| 4,384,406 A | 5/1983 | Tischlinger |
| 4,445,892 A | 5/1984 | Hussein et al. |
| 4,489,446 A | 12/1984 | Reed |
| 4,494,542 A | 1/1985 | Lee |
| 4,619,247 A | 10/1986 | Inoue et al. |
| 4,700,250 A | 10/1987 | Kuriyama |
| 4,726,371 A | 2/1988 | Gibbens |
| 4,758,221 A | 7/1988 | Jureidini |
| 4,784,133 A | 11/1988 | Mackin |
| 4,798,594 A | 1/1989 | Hillstead |
| 4,845,851 A | 7/1989 | Warthen |
| 4,848,341 A | 7/1989 | Ahmad |
| 4,850,354 A | 7/1989 | McGurk-Burleson et al. |
| 4,961,738 A | 10/1990 | Mackin |
| 4,969,893 A | 11/1990 | Swor |
| 4,976,710 A | 12/1990 | Mackin |
| 5,053,047 A | 10/1991 | Yoon |
| 5,064,431 A | 11/1991 | Gilbertson et al. |
| 5,084,058 A | 1/1992 | Li |
| 5,103,804 A | 4/1992 | Abele et al. |
| 5,108,368 A | 4/1992 | Hammerslag et al. |
| 5,133,723 A | 7/1992 | Li et al. |
| 5,221,255 A | 6/1993 | Mahurkar et al. |
| 5,221,269 A | 6/1993 | Miller et al. |
| 5,242,456 A | 9/1993 | Nash et al. |
| 5,242,457 A | 9/1993 | Akopov et al. |
| 5,257,975 A | 11/1993 | Foshee |
| 5,312,341 A | 5/1994 | Turi |
| 5,324,298 A | 6/1994 | Phillips et al. |
| 5,346,500 A | 9/1994 | Suchart |
| 5,358,479 A | 10/1994 | Wilson |
| 5,358,514 A | 10/1994 | Schulman et al. |
| 5,364,407 A | 11/1994 | Poll |
| 5,366,479 A | 11/1994 | McGarry et al. |
| 5,368,591 A | 11/1994 | Lennox et al. |
| 5,383,905 A | 1/1995 | Golds et al. |
| 5,409,483 A | 4/1995 | Campbell et al. |
| 5,417,700 A | 5/1995 | Egan |
| 5,423,837 A | 6/1995 | Mericle et al. |
| 5,437,680 A | 8/1995 | Yoon |
| 5,439,470 A | 8/1995 | Li |
| 5,450,860 A | 9/1995 | O'Connor |
| 5,452,513 A | 9/1995 | Zinnbauer et al. |
| 5,474,572 A | 12/1995 | Hayhurst |
| 5,507,760 A | 4/1996 | Wynne et al. |
| 5,520,702 A | 5/1996 | Sauer et al. |
| 5,522,873 A | 6/1996 | Jackman et al. |
| 5,524,630 A | 6/1996 | Crowley |
| 5,527,323 A | 6/1996 | Jervis et al. |
| 5,531,686 A | 7/1996 | Lundquist et al. |
| 5,545,134 A | 8/1996 | Hilaire et al. |
| 5,545,168 A | 8/1996 | Burke |
| 5,565,122 A | 10/1996 | Zinnbauer et al. |
| 5,571,215 A | 11/1996 | Sterman et al. |
| 5,591,194 A | 1/1997 | Berthiaume |
| 5,626,590 A | 5/1997 | Wilk |
| 5,626,614 A | 5/1997 | Hart |
| 5,630,824 A | 5/1997 | Hart |
| 5,643,289 A | 7/1997 | Sauer et al. |
| 5,669,917 A | 9/1997 | Sauer et al. |
| 5,674,279 A | 10/1997 | Wright et al. |
| 5,690,655 A | 11/1997 | Hart et al. |
| 5,709,695 A | 1/1998 | Northrup, III |
| 5,716,370 A | 2/1998 | Williamson, IV et al. |
| 5,718,725 A | 2/1998 | Sterman et al. |
| 5,725,542 A | 3/1998 | Yoon |
| 5,735,290 A | 4/1998 | Sterman et al. |
| 5,741,260 A | 4/1998 | Songer et al. |
| 5,741,301 A | 4/1998 | Pagedas |
| 5,752,518 A | 5/1998 | McGee et al. |
| 5,752,964 A | 5/1998 | Mericle |
| 5,752,966 A | 5/1998 | Chang |
| 5,755,730 A | 5/1998 | Swain et al. |
| 5,766,240 A | 6/1998 | Johnson |
| 5,769,812 A | 6/1998 | Stevens et al. |
| 5,782,861 A | 7/1998 | Cragg et al. |
| 5,810,848 A | 9/1998 | Hayhurst |
| 5,810,853 A | 9/1998 | Yoon |
| 5,817,107 A | 10/1998 | Schaller |
| 5,827,171 A | 10/1998 | Dobak, III et al. |
| 5,843,169 A | 12/1998 | Taheri |
| 5,848,969 A | 12/1998 | Panescu et al. |
| 5,860,992 A | 1/1999 | Daniel et al. |
| 5,860,993 A | 1/1999 | Thompson et al. |
| 5,868,733 A | 2/1999 | Ockuly et al. |
| 5,879,371 A | 3/1999 | Gardiner et al. |
| 5,885,238 A | 3/1999 | Stevens et al. |
| 5,888,240 A | 3/1999 | Carpentier et al. |
| 5,902,321 A | 5/1999 | Caspari et al. |
| 5,904,651 A | 5/1999 | Swanson et al. |
| 5,919,208 A | 7/1999 | Valenti |
| 5,935,149 A | 8/1999 | Ek |
| 5,947,983 A | 9/1999 | Solar et al. |
| 5,961,440 A | 10/1999 | Schweich, Jr. et al. |
| 5,961,539 A | 10/1999 | Northrup, III et al. |
| 5,972,004 A | 10/1999 | Williamson, IV et al. |
| 5,984,933 A | 11/1999 | Yoon |
| 5,989,284 A | 11/1999 | Laufer |
| 5,991,650 A | 11/1999 | Swanson et al. |
| 6,010,531 A | 1/2000 | Donlon et al. |
| 6,015,428 A | 1/2000 | Pagedas |
| 6,045,497 A | 4/2000 | Schweich, Jr. et al. |
| 6,050,936 A | 4/2000 | Schweich, Jr. et al. |

(56) References Cited

U.S. PATENT DOCUMENTS

| | | | |
|---|---|---|---|
| 6,059,715 A | 5/2000 | Schweich, Jr. et al. |
| 6,066,160 A | 5/2000 | Colvin et al. |
| 6,074,401 A | 6/2000 | Gardiner et al. |
| 6,077,214 A | 6/2000 | Mortier et al. |
| 6,077,989 A | 6/2000 | Kandel et al. |
| 6,099,553 A | 8/2000 | Hart et al. |
| 6,102,945 A | 8/2000 | Campbell |
| 6,125,852 A | 10/2000 | Stevens et al. |
| 6,149,658 A | 11/2000 | Gardiner et al. |
| 6,162,168 A | 12/2000 | Schweich, Jr. et al. |
| 6,165,183 A | 12/2000 | Kuehn et al. |
| 6,171,329 B1 | 1/2001 | Shaw et al. |
| 6,183,469 B1 | 2/2001 | Thapliyal et al. |
| 6,197,017 B1 | 3/2001 | Brock et al. |
| 6,221,084 B1 | 4/2001 | Fleenor |
| 6,228,096 B1 | 5/2001 | Marchand |
| 6,250,308 B1 | 6/2001 | Cox |
| 6,254,620 B1 | 7/2001 | Koh et al. |
| 6,258,118 B1 | 7/2001 | Baum et al. |
| 6,260,552 B1 | 7/2001 | Mortier et al. |
| 6,269,819 B1 | 8/2001 | Oz et al. |
| 6,283,993 B1 | 9/2001 | Cosgrove et al. |
| 6,306,149 B1 | 10/2001 | Meade |
| 6,312,447 B1 | 11/2001 | Grimes |
| 6,328,727 B1 | 12/2001 | Frazier et al. |
| 6,332,893 B1 | 12/2001 | Mortier et al. |
| 6,355,030 B1 | 3/2002 | Aldrich et al. |
| 6,378,289 B1 | 4/2002 | Trudeau et al. |
| 6,391,048 B1 | 5/2002 | Ginn et al. |
| 6,406,420 B1 | 6/2002 | McCarthy et al. |
| 6,409,743 B1 | 6/2002 | Fenton, Jr. |
| 6,423,088 B1 | 7/2002 | Fenton, Jr. |
| 6,432,123 B2 | 8/2002 | Schwartz et al. |
| 6,461,327 B1 | 10/2002 | Addis et al. |
| 6,514,265 B2 | 2/2003 | Ho et al. |
| 6,524,338 B1 | 2/2003 | Gundry |
| 6,533,753 B1 | 3/2003 | Haarstad et al. |
| 6,551,332 B1 | 4/2003 | Nguyen et al. |
| 6,575,971 B2 | 6/2003 | Hauck et al. |
| 6,575,987 B2 | 6/2003 | Gellman et al. |
| 6,589,160 B2 | 7/2003 | Schweich, Jr. et al. |
| 6,602,288 B1 | 8/2003 | Cosgrove et al. |
| 6,602,289 B1 | 8/2003 | Colvin et al. |
| 6,607,541 B1 | 8/2003 | Gardiner et al. |
| 6,613,059 B2 | 9/2003 | Schaller et al. |
| 6,619,291 B2 * | 9/2003 | Hlavka et al. ............... 128/898 |
| 6,626,899 B2 | 9/2003 | Houser et al. |
| 6,629,534 B1 * | 10/2003 | St. Goar et al. ............. 128/898 |
| 6,641,593 B1 | 11/2003 | Schaller et al. |
| 6,648,903 B1 | 11/2003 | Pierson, III |
| 6,651,671 B1 | 11/2003 | Donlon et al. |
| 6,655,386 B1 | 12/2003 | Makower et al. |
| 6,669,687 B1 | 12/2003 | Saadat |
| 6,676,702 B2 | 1/2004 | Mathis |
| 6,689,164 B1 | 2/2004 | Seguin |
| 6,699,263 B2 | 3/2004 | Cope |
| 6,702,826 B2 * | 3/2004 | Liddicoat et al. ............. 606/151 |
| 6,716,243 B1 | 4/2004 | Colvin et al. |
| 6,718,985 B2 | 4/2004 | Hlavka et al. |
| 6,723,038 B1 | 4/2004 | Schroeder et al. |
| 6,723,107 B1 | 4/2004 | Skiba et al. |
| 6,733,509 B2 | 5/2004 | Nobles et al. |
| 6,746,457 B2 | 6/2004 | Dana et al. |
| 6,749,622 B2 | 6/2004 | McGuckin et al. |
| 6,752,813 B2 | 6/2004 | Goldfarb et al. |
| 6,790,231 B2 | 9/2004 | Liddicoat et al. |
| 6,793,618 B2 | 9/2004 | Schweich, Jr. et al. |
| 6,875,224 B2 | 4/2005 | Grimes |
| 6,908,424 B2 | 6/2005 | Mortier et al. |
| 6,923,818 B2 | 8/2005 | Muramatsu et al. |
| 6,932,792 B1 | 8/2005 | St. Goar et al. |
| 6,986,775 B2 | 1/2006 | Morales et al. |
| 6,991,643 B2 | 1/2006 | Saadat |
| 6,997,931 B2 | 2/2006 | Sauer et al. |
| 7,004,958 B2 | 2/2006 | Adams et al. |
| 7,037,334 B1 | 5/2006 | Hlavka et al. |
| 7,044,957 B2 | 5/2006 | Foerster et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,166,127 B2 * | 1/2007 | Spence et al. ................ 623/2.37 |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,235,086 B2 | 6/2007 | Sauer et al. |
| 7,241,310 B2 * | 7/2007 | Taylor et al. ................ 623/2.36 |
| 7,344,544 B2 | 3/2008 | Bender et al. |
| 7,452,325 B2 | 11/2008 | Schaller |
| 7,588,582 B2 | 9/2009 | Starksen et al. |
| 7,618,449 B2 | 11/2009 | Tremulis et al. |
| 7,655,040 B2 | 2/2010 | Douk et al. |
| 7,666,193 B2 | 2/2010 | Starksen et al. |
| 7,753,922 B2 | 7/2010 | Starksen |
| 7,758,637 B2 | 7/2010 | Starksen et al. |
| 7,766,812 B2 | 8/2010 | Schroeder et al. |
| 7,883,538 B2 | 2/2011 | To et al. |
| 7,922,762 B2 | 4/2011 | Starksen |
| 7,993,368 B2 | 8/2011 | Gambale et al. |
| 8,066,766 B2 | 11/2011 | To et al. |
| 8,287,555 B2 | 10/2012 | Starksen et al. |
| 8,287,557 B2 | 10/2012 | To et al. |
| 8,641,727 B2 | 2/2014 | Starksen et al. |
| 2001/0005787 A1 | 6/2001 | Oz et al. |
| 2001/0014800 A1 | 8/2001 | Frazier et al. |
| 2001/0023332 A1 | 9/2001 | Hahnen |
| 2001/0031979 A1 | 10/2001 | Ricci |
| 2002/0013621 A1 | 1/2002 | Stobie et al. |
| 2002/0026201 A1 | 2/2002 | Foerster et al. |
| 2002/0029080 A1 | 3/2002 | Mortier et al. |
| 2002/0035361 A1 | 3/2002 | Houser et al. |
| 2002/0042621 A1 | 4/2002 | Liddicoat et al. |
| 2002/0065536 A1 | 5/2002 | Hart et al. |
| 2002/0072757 A1 | 6/2002 | Ahmed et al. |
| 2002/0077524 A1 | 6/2002 | Schweich, Jr. et al. |
| 2002/0087048 A1 | 7/2002 | Brock et al. |
| 2002/0087049 A1 | 7/2002 | Brock et al. |
| 2002/0087148 A1 | 7/2002 | Brock et al. |
| 2002/0087169 A1 | 7/2002 | Brock et al. |
| 2002/0095167 A1 | 7/2002 | Liddicoat et al. |
| 2002/0095175 A1 | 7/2002 | Brock et al. |
| 2002/0138044 A1 | 9/2002 | Streeter et al. |
| 2002/0156526 A1 | 10/2002 | Hlavka et al. |
| 2002/0161378 A1 | 10/2002 | Downing |
| 2002/0165486 A1 | 11/2002 | Bertolero et al. |
| 2002/0173841 A1 | 11/2002 | Ortiz et al. |
| 2002/0183835 A1 | 12/2002 | Taylor et al. |
| 2002/0193815 A1 | 12/2002 | Foerster et al. |
| 2003/0009196 A1 | 1/2003 | Peterson |
| 2003/0018358 A1 | 1/2003 | Saadat |
| 2003/0032979 A1 | 2/2003 | Mortier et al. |
| 2003/0033006 A1 | 2/2003 | Phillips et al. |
| 2003/0060813 A1 | 3/2003 | Loeb et al. |
| 2003/0069593 A1 | 4/2003 | Tremulis et al. |
| 2003/0074012 A1 | 4/2003 | Nguyen et al. |
| 2003/0078465 A1 | 4/2003 | Pai et al. |
| 2003/0078601 A1 | 4/2003 | Shikhman et al. |
| 2003/0078603 A1 | 4/2003 | Schaller et al. |
| 2003/0093118 A1 | 5/2003 | Ho et al. |
| 2003/0105520 A1 | 6/2003 | Alferness et al. |
| 2003/0125739 A1 | 7/2003 | Bagga et al. |
| 2003/0125767 A1 | 7/2003 | Collier et al. |
| 2003/0130731 A1 * | 7/2003 | Vidlund et al. ............. 623/2.37 |
| 2003/0144697 A1 | 7/2003 | Mathis et al. |
| 2003/0158464 A1 | 8/2003 | Bertolero |
| 2003/0158581 A1 | 8/2003 | Levinson |
| 2003/0167062 A1 | 9/2003 | Gambale et al. |
| 2003/0167071 A1 | 9/2003 | Martin et al. |
| 2003/0199974 A1 | 10/2003 | Lee et al. |
| 2003/0220685 A1 * | 11/2003 | Hlavka et al. ............... 623/2.11 |
| 2003/0225420 A1 | 12/2003 | Wardle |
| 2003/0233105 A1 | 12/2003 | Gayton |
| 2003/0233142 A1 | 12/2003 | Morales et al. |
| 2003/0236535 A1 | 12/2003 | Onuki et al. |
| 2004/0003819 A1 | 1/2004 | St. Goar et al. |

(56) References Cited

U.S. PATENT DOCUMENTS

| | | |
|---|---|---|
| 2004/0019378 A1 | 1/2004 | Hlavka et al. |
| 2004/0030382 A1 | 2/2004 | St. Goar et al. |
| 2004/0039442 A1 | 2/2004 | St. Goar et al. |
| 2004/0092962 A1 | 5/2004 | Thornton et al. |
| 2004/0093024 A1 | 5/2004 | Lousararian et al. |
| 2004/0097788 A1 | 5/2004 | Mourlas et al. |
| 2004/0122450 A1 | 6/2004 | Oren et al. |
| 2004/0172046 A1 | 9/2004 | Hlavka et al. |
| 2004/0181238 A1 | 9/2004 | Zarbatany et al. |
| 2004/0186378 A1 | 9/2004 | Gesswein |
| 2004/0193191 A1 | 9/2004 | Starksen et al. |
| 2004/0204724 A1 | 10/2004 | Kissel et al. |
| 2004/0210238 A1 | 10/2004 | Nobles et al. |
| 2004/0236372 A1 | 11/2004 | Anspach, III et al. |
| 2004/0236419 A1 | 11/2004 | Milo |
| 2004/0243227 A1 | 12/2004 | Starksen et al. |
| 2005/0021054 A1 | 1/2005 | Ainsworth et al. |
| 2005/0055052 A1 | 3/2005 | Lombardo et al. |
| 2005/0055087 A1 | 3/2005 | Starksen |
| 2005/0065550 A1 | 3/2005 | Starksen et al. |
| 2005/0075723 A1 | 4/2005 | Schroeder et al. |
| 2005/0080454 A1 | 4/2005 | Drews et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0119523 A1 | 6/2005 | Starksen et al. |
| 2005/0119673 A1 | 6/2005 | Gordon et al. |
| 2005/0137689 A1 | 6/2005 | Salahieh et al. |
| 2005/0184122 A1 | 8/2005 | Hlavka et al. |
| 2005/0192599 A1 | 9/2005 | Demarais |
| 2005/0192629 A1 | 9/2005 | Saadat et al. |
| 2005/0197694 A1 | 9/2005 | Pai et al. |
| 2005/0209690 A1 | 9/2005 | Mathis et al. |
| 2005/0216078 A1 | 9/2005 | Starksen et al. |
| 2005/0228452 A1 | 10/2005 | Mourlas et al. |
| 2005/0251157 A1 | 11/2005 | Saadat et al. |
| 2005/0251159 A1 | 11/2005 | Ewers et al. |
| 2005/0251166 A1 | 11/2005 | Vaughan et al. |
| 2005/0251177 A1 | 11/2005 | Saadat et al. |
| 2005/0251205 A1 | 11/2005 | Ewers et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267495 A1 | 12/2005 | Ginn et al. |
| 2005/0273138 A1 | 12/2005 | To et al. |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2006/0015144 A1 | 1/2006 | Burbank et al. |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0058817 A1 | 3/2006 | Starksen et al. |
| 2006/0069429 A1 | 3/2006 | Spence et al. |
| 2006/0122633 A1 | 6/2006 | To et al. |
| 2006/0129188 A1 | 6/2006 | Starksen et al. |
| 2006/0161040 A1 | 7/2006 | McCarthy et al. |
| 2006/0178682 A1 | 8/2006 | Boehlke |
| 2006/0184203 A1 | 8/2006 | Martin et al. |
| 2006/0190030 A1 | 8/2006 | To et al. |
| 2006/0241656 A1 | 10/2006 | Starksen et al. |
| 2006/0264975 A1 | 11/2006 | Pipenhagen et al. |
| 2006/0271101 A1 | 11/2006 | Saadat et al. |
| 2006/0287661 A1 | 12/2006 | Bolduc et al. |
| 2007/0005081 A1 | 1/2007 | Findlay, III et al. |
| 2007/0005394 A1 | 1/2007 | Bleyendaal et al. |
| 2007/0010857 A1 | 1/2007 | Sugimoto et al. |
| 2007/0032820 A1 | 2/2007 | Chin-Chen et al. |
| 2007/0038293 A1 | 2/2007 | St.Goar et al. |
| 2007/0049942 A1 | 3/2007 | Hindrichs et al. |
| 2007/0051377 A1* | 3/2007 | Douk et al. ............ 128/897 |
| 2007/0055206 A1 | 3/2007 | To et al. |
| 2007/0112422 A1 | 5/2007 | Dehdashtian |
| 2007/0112424 A1 | 5/2007 | Spence et al. |
| 2008/0045977 A1 | 2/2008 | To et al. |
| 2008/0045982 A1 | 2/2008 | To et al. |
| 2008/0045983 A1 | 2/2008 | To et al. |
| 2008/0051810 A1 | 2/2008 | To et al. |
| 2008/0051832 A1 | 2/2008 | To et al. |
| 2008/0051837 A1 | 2/2008 | To et al. |
| 2008/0058868 A1 | 3/2008 | To et al. |
| 2008/0234728 A1 | 9/2008 | Starksen et al. |
| 2008/0234815 A1 | 9/2008 | Starksen |
| 2008/0294177 A1 | 11/2008 | To et al. |
| 2009/0182417 A1 | 7/2009 | Tremulis et al. |
| 2009/0222083 A1 | 9/2009 | Nguyen et al. |
| 2009/0234318 A1 | 9/2009 | Loulmet et al. |
| 2009/0276038 A1 | 11/2009 | Tremulis et al. |
| 2010/0049213 A1 | 2/2010 | Serina et al. |
| 2010/0076548 A1 | 3/2010 | Konno |
| 2010/0082098 A1 | 4/2010 | Starksen et al. |
| 2010/0094314 A1 | 4/2010 | Hernlund et al. |
| 2010/0121349 A1 | 5/2010 | Meier et al. |
| 2011/0160528 A1 | 6/2011 | Starksen |
| 2013/0304093 A1 | 11/2013 | Serina et al. |
| 2014/0194976 A1 | 7/2014 | Starksen et al. |

FOREIGN PATENT DOCUMENTS

| | | |
|---|---|---|
| JP | 6-510460 A | 11/1994 |
| JP | 11-506628 A | 6/1999 |
| JP | 2004-601 A | 1/2004 |
| JP | 2004-530451 A | 10/2004 |
| JP | 2007-514455 A | 6/2007 |
| WO | WO-93/08740 A1 | 5/1993 |
| WO | WO 94/03227 | 2/1994 |
| WO | WO-95/15715 A1 | 6/1995 |
| WO | WO-96/08208 A1 | 3/1996 |
| WO | WO-96/39081 A1 | 12/1996 |
| WO | WO-96/39942 A1 | 12/1996 |
| WO | WO-97/27799 A1 | 8/1997 |
| WO | WO-97/27807 A1 | 8/1997 |
| WO | WO 98/07375 | 2/1998 |
| WO | WO-00/60995 A2 | 10/2000 |
| WO | WO-00/60995 A3 | 10/2000 |
| WO | WO-00/67640 A2 | 11/2000 |
| WO | WO-00/67640 A3 | 11/2000 |
| WO | WO 01/26586 | 4/2001 |
| WO | WO-01/54618 A1 | 8/2001 |
| WO | WO 02/03892 | 1/2002 |
| WO | WO-02/34167 A2 | 5/2002 |
| WO | WO-02/34167 A3 | 5/2002 |
| WO | WO-02/051329 A1 | 7/2002 |
| WO | WO-02/085251 A1 | 10/2002 |
| WO | WO-02/085252 A1 | 10/2002 |
| WO | WO-03/088875 A1 | 10/2003 |
| WO | WO-03/105667 A2 | 12/2003 |
| WO | WO-03/105667 A3 | 12/2003 |
| WO | WO-03/105670 A2 | 12/2003 |
| WO | WO-03/105670 A3 | 12/2003 |
| WO | WO-2004/037317 A2 | 5/2004 |
| WO | WO-2004/037317 A3 | 5/2004 |
| WO | WO-2004/082523 A2 | 9/2004 |
| WO | WO-2004/082523 A3 | 9/2004 |
| WO | WO-2004/082538 A2 | 9/2004 |
| WO | WO-2004/082538 A3 | 9/2004 |
| WO | WO-2005/025644 A2 | 3/2005 |
| WO | WO-2005/062931 A2 | 7/2005 |
| WO | WO-2005/062931 A3 | 7/2005 |
| WO | WO-2005/102181 A1 | 11/2005 |
| WO | WO-2006/034243 A2 | 3/2006 |
| WO | WO-2006/034243 A3 | 3/2006 |
| WO | WO-2006/037073 A2 | 4/2006 |
| WO | WO-2006/097931 A2 | 9/2006 |
| WO | WO-2006/097931 A3 | 9/2006 |
| WO | WO-2006/116558 A2 | 11/2006 |
| WO | WO-2006/116558 A3 | 11/2006 |
| WO | WO-2006/116558 C2 | 11/2006 |
| WO | WO-2007/005495 A1 | 1/2007 |
| WO | WO-2007/021564 A1 | 2/2007 |
| WO | WO-2007/021834 A1 | 2/2007 |
| WO | WO-2007/035449 A2 | 3/2007 |
| WO | WO-2007/056502 A1 | 5/2007 |

(56) References Cited

FOREIGN PATENT DOCUMENTS

| WO | WO-2007/100409 A2 | 9/2007 |
| WO | WO-2008/028135 A2 | 3/2008 |
| WO | WO-2008-028135 A3 | 3/2008 |

OTHER PUBLICATIONS

Non-Final Office Action mailed Jan. 31, 2008, for U.S. Appl. No. 11/255,400, filed Oct. 20, 2005, 7 pages.
Final Office Action mailed on May 28, 2008, for U.S. Appl. No. 11/270,034, filed Nov. 8, 2005, 10 pages.
Final Office Action mailed on Jun. 4, 2008, for U.S. Appl. No. 11/202,474, filed Aug. 11, 2005, 10 pages.
Non-Final Office Action (Supplementary) mailed on May 9, 2008, for U.S. Appl. No. 11/255,400, filed Oct. 20, 2005, 7 pages.
Non-Final Office Action mailed on Jun. 6, 2008, for U.S. Appl. No. 10/656,797, 5 pages.
U.S. Appl. No. 12/132,161, filed Jun. 3, 2008, by Starksen et al.
U.S. Appl. No. 12/132,375, filed Jun. 3, 2008, by Starksen et al.
De Simone, R. et al. (Apr. 15, 1993). "Adjustable Tricuspid Valve Annuloplasty Assisted by Intraoperative Transesophageal Color Doppler Echocardiography," *Am. J. Cardiol.* 71(11):926-931.
De Simone, R. et al. (Apr. 1, 1994). "Adjustable Annuloplasty for Tricuspid Insufficiency with External Control," *Reader's Comments and Reply, Am. J. Cardiol.* 73(9):721-722.
International Search Report mailed on Apr. 2, 2007, for PCT Application No. PCT/US2006/043597, filed Nov. 8, 2006, seven pages.
Final Office Action mailed on Apr. 2, 2008, for U.S. Appl. No. 10/792,681, filed Mar. 2, 2004, 15 pages.
Final Office Action mailed on Apr. 14, 2008, for U.S. Appl. No. 10/091,019, filed Jul. 27, 2004, 11 pages.
Non-Final Office Action mailed on Mar. 27, 2008, for U.S. Appl. No. 10/900,980, filed Jul. 27, 2004, 7 pages.
Final Office Action mailed on Aug. 1, 2008, for U.S. Appl. No. 11/232,190, filed Sep. 20, 2005, 8 pages.
Final Office Action mailed on Sep. 30, 2008, for U.S. Appl. No. 10/900,980, filed Jul. 27, 2004, 7 pages.
Final Office Action mailed on Oct. 14, 2008, for U.S. Appl. No. 10/741,130, filed Dec. 19, 2003, 9 pages.
Non-Final Office Action mailed on Aug. 29, 2008, for U.S. Appl. No. 10/792,681, filed Mar. 2, 2004, 15 pages.
Non-Final Office Action mailed on Sep. 26, 2008, for U.S. Appl. No. 11/414,657, filed Apr. 27, 2006, 11 pages.
Non-Final Office Action mailed on Oct. 24, 2008, for U.S. Appl. No. 10/901,019, filed Jul. 27, 2004, 11 pages.
Supplementary European Search Report mailed on Nov. 10, 2008, for EP Application No. 04 78 2847, filed on Sep. 1, 2004, 2 pages.
U.S. Appl. No. 12/187,331, filed Aug. 6, 2008, by To et al.
International Search Report mailed Dec. 19, 2006, for PCT Application No. PCT/US2006/031190, filed Aug. 10, 2006, four pages.
De Simone et al. Adjustable tricuspid valve annuloplasty assisted by intraoperative transesophageal color Doppler echocardiography, Am. J Cardiol 73:721-722 (Apr. 1993).
Downing et al. Feasibility of Off-Pump ASD Closure Using Real-Time 3-D Echocardiography, Heart Surgery Forum, (Jun. 27, 2001).
Nagy, Zsolt L. et al., "Mitral annuplasty with a suture technique", European Journal of Cardio-thoracic Surgery 18 (2000) p. 739.
Shumway, Sara J. et al., "A "Designer" Annuplasty Ring for Patients with Massive Mitral Annular Dilation", Ann Thorac Surg, Dec. 1988, 46:695-696.
Final Office Action mailed on Feb. 6, 2007, for U.S. Appl. No. 10/656,797, filed Sep. 4, 2003, 8 pages.
Final Office Action mailed on Jul. 12, 2007, for U.S. Appl. No. 11/202,474, filed Aug. 11, 2005, 10 pages.
Final Office Action mailed on Jul. 24, 2007, for U.S. Appl. No. 10/741,130, filed Dec. 19, 2003, 10 pages.
Final Office Action mailed on Aug. 6, 2007, for U.S. Appl. No. 10/901,019, filed Jul. 27, 2004, 12 pages.
Final Office Action mailed on Aug. 6, 2007, for U.S. Appl. No. 11/137,833, filed May 24, 2005, 8 pages.
Final Office Action mailed on Aug. 13, 2007, for U.S. Appl. No. 10/900,980, filed Jul. 27, 2004, 9 pages.
Final Office Action mailed on Aug. 14, 2007, for U.S. Appl. No. 11/255,400, filed Oct. 20, 2005, 8 pages.
Final Office Action mailed on Aug. 30, 2007, for U.S. Appl. No. 11/232,190, filed Sep. 20, 2005, 9 pages.
Final Office Action mailed on Oct. 30, 2007, for U.S. Appl. No. 10/656,797, filed Sep. 4, 2003, 6 pages.
Non-Final Office Action mailed on Aug. 9, 2006, for U.S. Appl. No. 10/900,980, filed Jul. 27, 2004, 17 pages.
Non-Final Office Action mailed on Aug. 22, 2006, for U.S. Appl. No. 10/656,797, filed Sep. 4, 2003, 6 pages.
Non-Final Office Action mailed on Nov. 15, 2006, for U.S. Appl. No. 11/137,833, filed May 24, 2005, 12 pages.
Non-Final Office Action mailed on Nov. 28, 2006, for U.S. Appl. No. 10/901,019, filed Jul. 27, 2004, 20 pages.
Non-Final Office Action mailed on Dec. 27, 2006, for U.S. Appl. No. 10/741,130, filed Dec. 19, 2003, 9 pages.
Non-Final Office Action mailed on Dec. 27, 2006, for U.S. Appl. No. 11/270,034, filed Nov. 8, 2005, 8 pages.
Non-Final Office Action mailed on Jan. 4, 2007, for U.S. Appl. No. 11/255,400, filed Oct. 20, 2005, 7 pages.
Non-Final Office Action mailed on Feb. 27, 2007, for U.S. Appl. No. 11/202,474, filed Aug. 11, 2005, 8 pages.
Non-Final Office Action mailed on Mar. 12, 2007, for U.S. Appl. No. 11/232,190, filed Sep. 20, 2005, 11 pages.
Non-Final Office Action mailed on Jul. 24, 2007, for U.S. Appl. No. 10/656,797, filed Sep. 4, 2003, 6 pages.
Non-Final Office Action mailed on Aug. 1, 2007, for U.S. Appl. No. 10/792,681, filed Mar. 2, 2004, 16 pages.
Non-Final Office Action mailed on Aug. 30, 2007, for U.S. Appl. No. 11/270,034, filed Nov. 8, 2005, 10 pages.
Non-Final Office Action mailed on Oct. 19, 2007, for U.S. Appl. No. 11/202,474, filed Aug. 11, 2005, 7 pages.
Non-Final Office Action mailed on Oct. 29, 2007, for U.S. Appl. No. 10/901,019, filed Jul. 27, 2004, 10 pages.
Non-Final Office Action mailed on Nov. 14, 2007, for U.S. Appl. No. 10/741,130, filed Dec. 19, 2003, 8 pages.
Non-Final Office Action mailed on Nov. 14, 2007, for U.S. Appl. No. 11/137,833, filed May 24, 2005, 8 pages.
U.S. Appl. No. 11/656,141, filed Jan. 19, 2007, by Straksen et al.
U.S. Appl. No. 11/875,774, filed Oct. 19, 2007, by Serina et al.
U.S. Appl. No. 11/894,340, filed Aug. 20, 2007, by To et al.
U.S. Appl. No. 11/894,368, filed Aug. 20, 2007, by To et al.
U.S. Appl. No. 11/894,397, filed Aug. 20, 2007, by To et al.
U.S. Appl. No. 11/894,401, filed Aug. 20, 2007, by To et al.
U.S. Appl. No. 11/894,463, filed Aug. 20, 2007, by To et al.
U.S. Appl. No. 11/894,468, filed Aug. 20, 2007, by To et al.
U.S. Appl. No. 11/894,530, filed Aug. 20, 2007, by To et al.
Final Office Action mailed on Jan. 22, 2009, for U.S. Appl. No. 11/255,400, filed Oct. 20, 2005, 9 pages.
Final Office Action mailed on Mar. 11, 2009, for U.S. Appl. No. 10/656,797, filed Sep. 4, 2003, 10 pages.
Final Office Action mailed on Apr. 10, 2009, for U.S. Appl. No. 11/414,657, filed Apr. 27, 2006, 8 pages.
Final Office Action mailed on Apr. 10, 2009, for U.S. Appl. No. 11/255,400, filed Oct. 20, 2005, 8 pages.
Final Office Action mailed on Apr. 29, 2009, for U.S. Appl. No. 10/901,019, filed Jul. 27, 2004, 9 pages.
Non-Final Office Action mailed on Jan. 13, 2009, for U.S. Appl. No. 10/901,555, filed Jul 27, 2004, 11 pages.
Non-Final Office Action mailed on Jan. 23, 2009, for U.S. Appl. No. 11/232,190, filed Sep. 20, 2005, 8 pages.
Non-Final Office Action mailed on Jan. 23, 2009, for U.S. Appl. No. 11/270,034, filed Nov. 8, 2005, 8 pages.
Non-Final Office Action mailed on Jan. 29, 2009, for U.S. Appl. No. 10/900,980, filed Jul. 27, 2004, 6 pages.
Non-Final Office Action mailed on Mar. 5, 2009, for U.S. Appl. No. 11/202,474, filed Aug. 11, 2005, 10 pages.
Non-Final Office Action mailed on Mar. 27, 2009, for U.S. Appl. No. 10/741,130, filed Dec. 19, 2003, 9 pages.
Non-Final Office Action mailed on Mar. 31, 2009, for U.S. Appl. No. 10/792,681, filed Mar. 2, 2004, 15 pages.

(56) References Cited

OTHER PUBLICATIONS

European Examination Communication mailed on Dec. 8, 2009, for EP Application No. 06 837 222.6 filed on Nov. 8, 2006, three pages.
Final Office Action mailed on Jul. 21, 2009, for U.S. Appl. No. 11/270,034, filed Nov. 8, 2005, 8 pages.
Final Office Action mailed on Sep. 2, 2009, for U.S. Appl. No. 11/232,190, filed Sep. 20, 2005, 8 pages.
Final Office Action mailed on Sep. 28, 2009, for U.S. Appl. No. 11/202,474, filed Aug. 11, 2005, 10 pages.
Final Office Action mailed on Nov. 10, 2009, for U.S. Appl. No. 10/741,130, filed Dec. 19, 2003, 9 pages.
Non-Final Office Action mailed on Aug. 25, 2009, for U.S. Appl. No. 10/900,980, filed Jul. 27, 2004, 7 pages.
Non-Final Office Action mailed on Aug. 26, 2009, for U.S. Appl. No. 11/414,657, filed Apr. 27, 2006, 6 pages.
Non-Final Office Action mailed on Sep. 17, 2009, for U.S. Appl. No. 10/656,797, filed Sep. 4, 2003, 13 pages.
Non-Final Office Action mailed on Oct. 19, 2009, for U.S. Appl. No. 10/901,019, filed Jul. 27, 2004, 21 pages.
Notice of Allowance mailed on Aug. 4, 2009, for U.S. Appl. No. 10/901,555, filed Jul. 27, 2004, 7 pages.
U.S. Appl. No. 12/581,040, filed Oct. 16, 2009, by Starksen et al.
Final Office Action mailed on Mar. 3, 2010, for U.S. Appl. No. 11/414,657, filed Apr. 27, 2006, 7 pages.
Final Office Action mailed on Mar. 25, 2010, for U.S. Appl. No. 10/900,980, filed Jul. 27, 2004, 8 pages.
Final Office Action mailed on Jun. 8, 2010, for U.S. Appl. No. 10/792,681, filed Mar. 2, 2004, 17 pages.
Final Office Action mailed on Jul. 26, 2010, for U.S. Appl. No. 11/270,034, filed Nov. 8, 2005, 8 pages.
Final Office Action mailed on Sep. 15, 2010, for U.S. Appl. No. 11/894,401, filed Aug. 20, 2007, 6 pages.
Final Office Action mailed on Oct. 6, 2010, for U.S. Appl. No. 12/132,375, filed Jun. 3, 2008, 9 pages.
Non-Final Office Action mailed on Jan. 19, 2010, for U.S. Appl. No. 11/270,034, filed Nov. 8, 2005, 10 pages.
Non-Final Office Action mailed on Feb. 18, 2010, for U.S. Appl. No. 11/894,401, filed Aug. 20, 2007, 6 pages.
Non-Final Office Action mailed on Mar. 16, 2010, for U.S. Appl. No. 11/894,340, filed Aug. 20, 2007, 14 pages.
Non-Final Office Action mailed on Mar. 29, 2010, for U.S. Appl. No. 11/894,463, filed Aug. 20, 2007, 14 pages.
Non-Final Office Action mailed on Apr. 2, 2010, for U.S. Appl. No. 12/132,375, filed Jun. 3, 2008, 9 pages.
Non-Final Office Action mailed on Jun. 9, 2010, for U.S. Appl. No. 11/894,468, filed Aug. 20, 2007, 14 pages.
Non-Final Office Action mailed on Aug. 17, 2010, for U.S. Appl. No. 11/414,657, filed Apr. 27, 2006, 7 pages.
Non-Final Office Action mailed on Oct. 8, 2010, for U.S. Appl. No. 11/894,368, filed Aug. 20, 2007, 10 pages.
Non-Final Office Action mailed on Oct. 25, 2010, for U.S. Appl. No. 11/202,474, filed Aug. 11, 2005, 8 pages.
Non-Final Office Action mailed on Oct. 29, 2010, for U.S. Appl. No. 11/894,530, filed Aug. 20, 2007, 11 pages.
Non-Final Office Action mailed on Nov. 24, 2010, for U.S. Appl. No. 10/900,980, filed Jul. 27, 2004, 8 pages.
Notice of Allowance mailed on Feb. 24, 2010, for U.S. Appl. No. 10/656,797, filed Sep. 4, 2003, 8 pages.
Notice of Allowance mailed on Apr. 28, 2010, for U.S. Appl. No. 10/901,019, filed Jul. 27, 2004, 7 pages.
Notice of Allowance mailed on Nov. 17, 2010, for U.S. Appl. No. 11/232,190, filed Sep. 20, 2005, 11 pages.
U.S. Appl. No. 12/850,531, filed Aug. 4, 2010, by Starksen et al.
Final Office Action mailed on Dec. 6, 2011, for U.S. Appl. No. 12/366,553, filed Feb. 5, 2009, 7 pages.
Non-Final Office Action mailed on Jul. 29, 2011, for U.S. Appl. No. 12/574,563, filed Oct. 6, 2009, 5 pages.
Non-Final Office Action mailed on Dec. 22, 2011, for U.S. Appl. No. 11/270,034, filed Nov. 8, 2005, 9 pages.
Extended European Search Report mailed on Sep. 9, 2011, for EP Patent Application No. 11158896.8, filed on Sep. 1, 2004, 7 pages.
Extended European Search Report mailed on Sep. 16, 2011, for EP Patent Application No. 11158898.4, filed on Sep. 1, 2004, 8 pages.
Final Office Action mailed on Nov. 26, 2010, for U.S. Appl. No. 11/894,340, filed Aug. 20, 2007, 12 pages.
Final Office Action mailed on Nov. 29, 2010, for U.S. Appl. No. 11/894,463, filed Aug. 20, 2007, 12 pages.
Final Office Action mailed on Feb. 24, 2011, for U.S. Appl. No. 11/894,397, filed Aug. 20, 2007, 12 pages.
Final Office Action mailed on Feb. 24, 2011, for U.S. Appl. No. 11/894,468, filed Aug. 20, 2007, 12 pages.
Final Office Action mailed on Mar. 17, 2011, for U.S. Appl. No. 11/202,474, filed Aug. 11, 2005, 9 pages.
Final Office Action mailed on Apr. 20, 2011, for U.S. Appl. No. 11/414,657, filed Apr. 27, 2006, 8 pages.
Final Office Action mailed on Aug. 4, 2011, for U.S. Appl. No. 10/900,980, filed Jul. 27, 2004, 9 pages.
Final Office Action mailed on Nov. 3, 2011, for U.S. Appl. No. 12/581,040, filed Oct. 16, 2009, 5 pages.
Final Office Action mailed on Nov. 10, 2011, for U.S. Appl. No. 10/792,681, filed Mar. 2, 2004, 20 pages.
Non-Final Office Action mailed on Feb. 2, 2011, for U.S. Appl. No. 12/581,040, filed Oct. 16, 2009, 5 pages.
Non-Final Office Action mailed on Apr. 27, 2011, for U.S. Appl. No. 12/366,533, filed Feb. 5, 2009, 9 pages.
Non-Final Office Action mailed on Oct. 13, 2011, for U.S. Appl. No. 12/187,331, filed Aug. 6, 2008, 5 pages.
Non-Final Office Action mailed on Oct. 18, 2011, for U.S. Appl. No. 12/132,161, filed Jun. 3, 2008, 15 pages.
Non-Final Office Action mailed on Oct. 18, 2011, for U.S. Appl. No. 10/741,130, filed Dec. 19, 2003, 9 pages.
Notice of Allowance mailed on Dec. 6, 2010, for U.S. Appl. No. 12/132,375, filed Jun. 3, 2008, 9 pages.
Notice of Allowance mailed on Jul. 26, 2011, for U.S. Appl. No. 11/894,530, filed Aug. 20, 2007, 10 pages.
Final Office Action mailed on Mar. 19, 2012, for U.S. Appl. No. 12/574,563, filed Oct. 6, 2009, 6 pages.
Final Office Action mailed on Jun. 11, 2012, for U.S. Appl. No. 12/132,161, filed Jun. 3, 2008, 13 pages.
Final Office Action mailed on Jun. 11, 2012, for U.S. Appl. No. 12/187,331, filed Jun. 6, 2008, 7 pages.
Non-Final Office Action mailed on Jun. 7, 2012, for U.S. Appl. No. 12/850,531, filed Aug. 4, 2010, 8 pages.
Non-Final Office Action mailed on Nov. 7, 2014, for U.S. Appl. No. 12/187,331, filed Aug. 6, 2008, 8 pages.
Notice of Allowance mailed on Jun. 11, 2012, for U.S. Appl. No. 10/741,130, filed Dec. 19, 2003, 9 pages.
Notice of Allowance mailed on Sep. 25, 2013, for U.S. Appl. No. 12/132,161, filed Jun. 3, 2008, 12 pages.

* cited by examiner

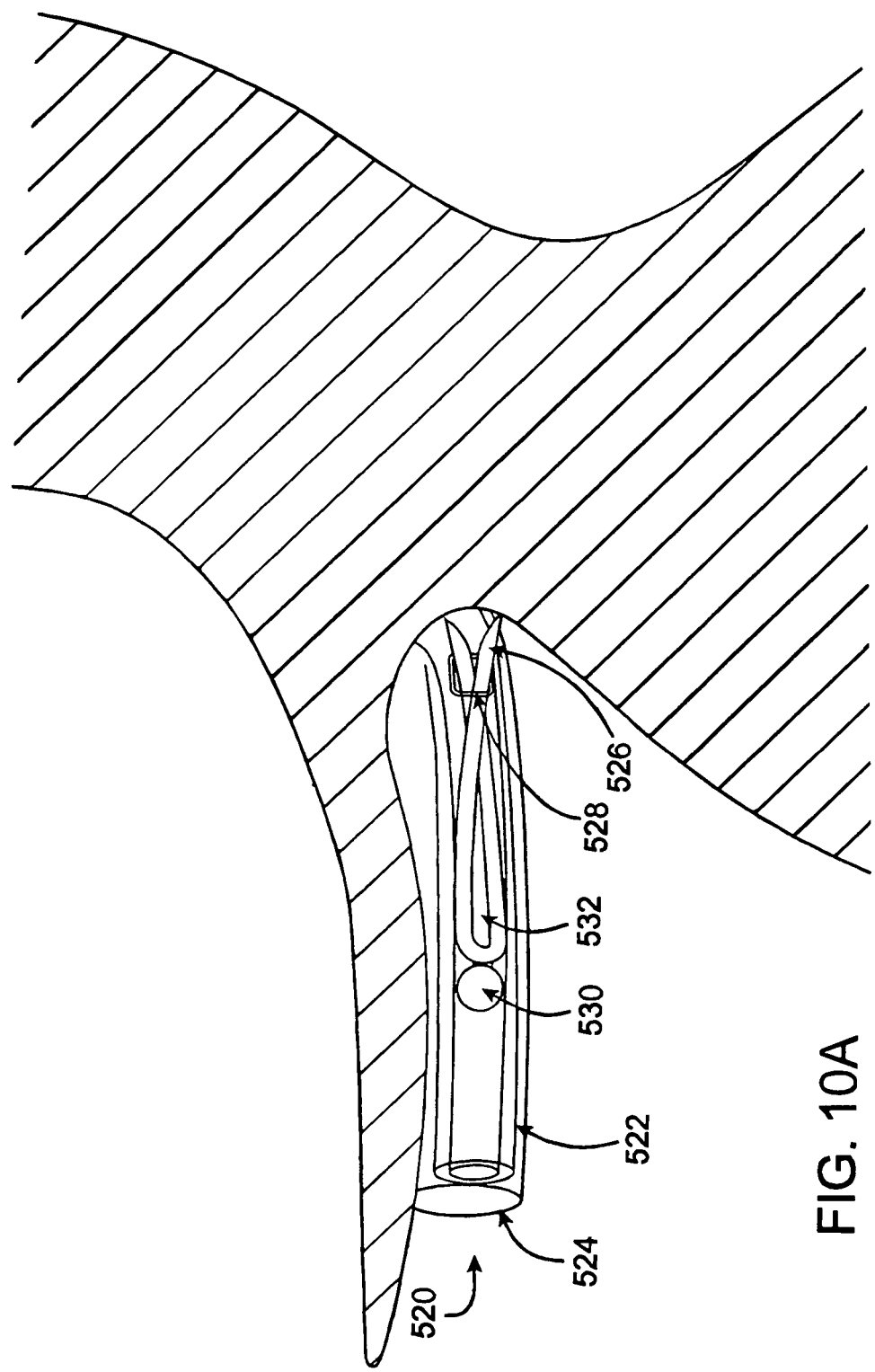

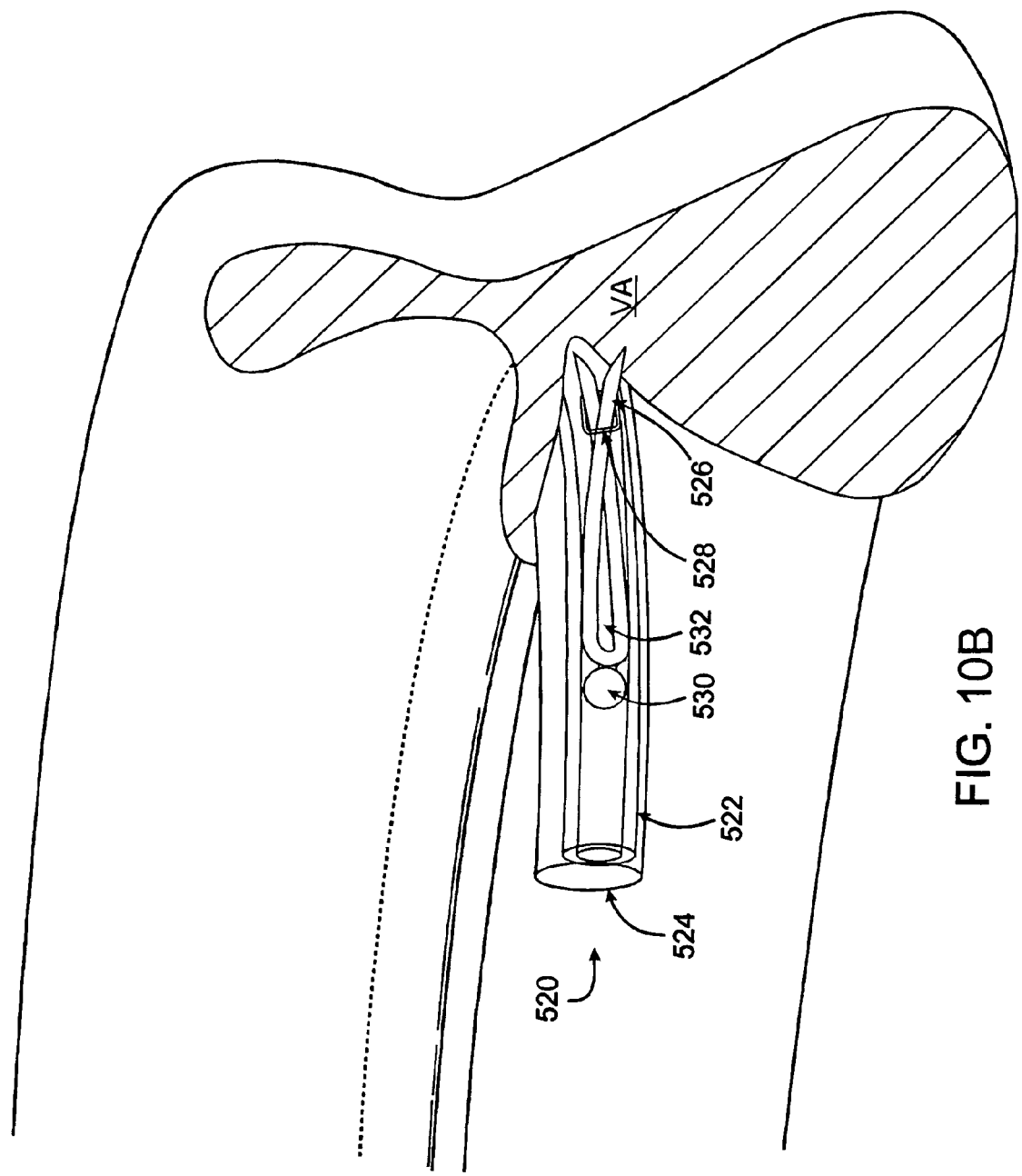

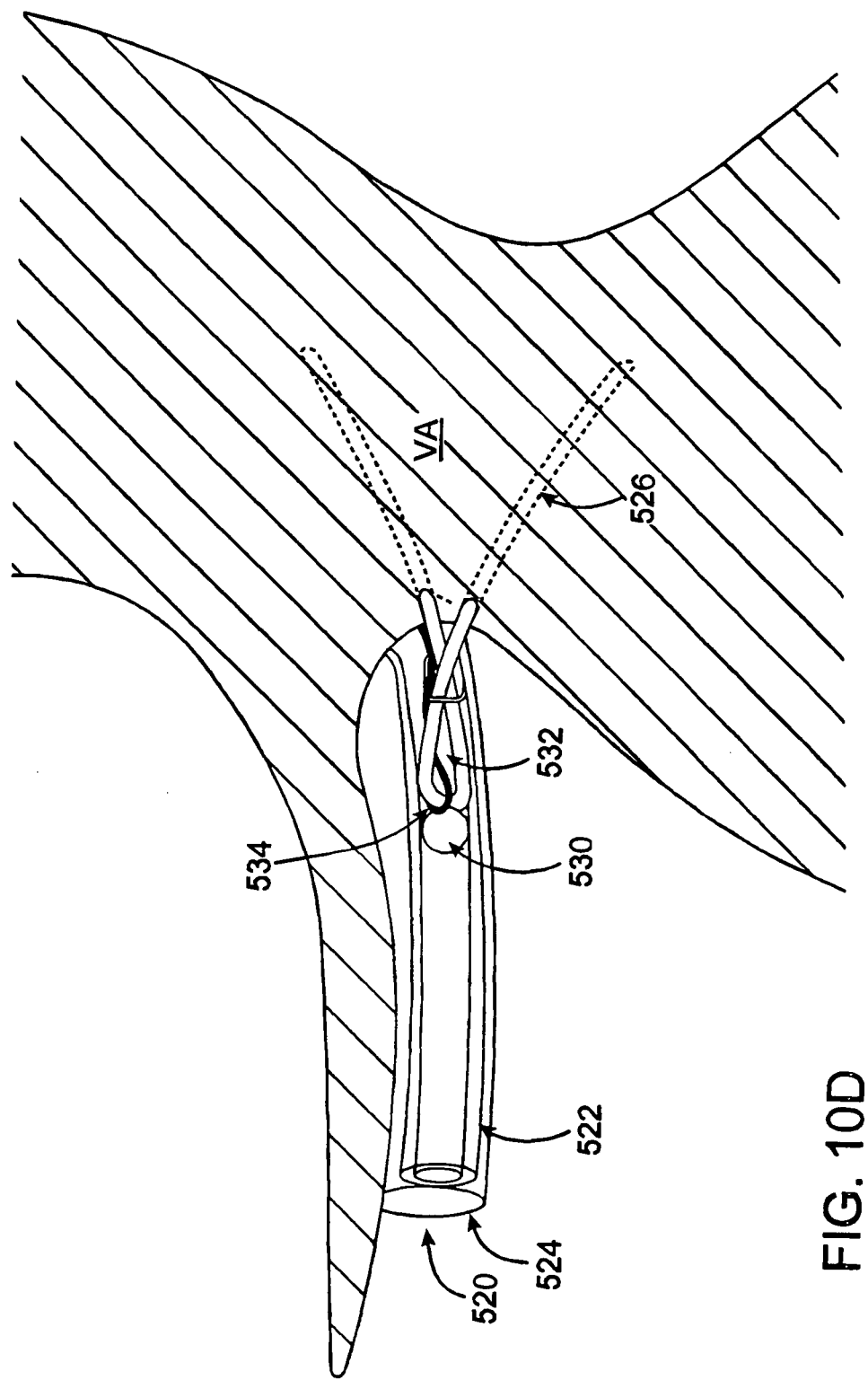

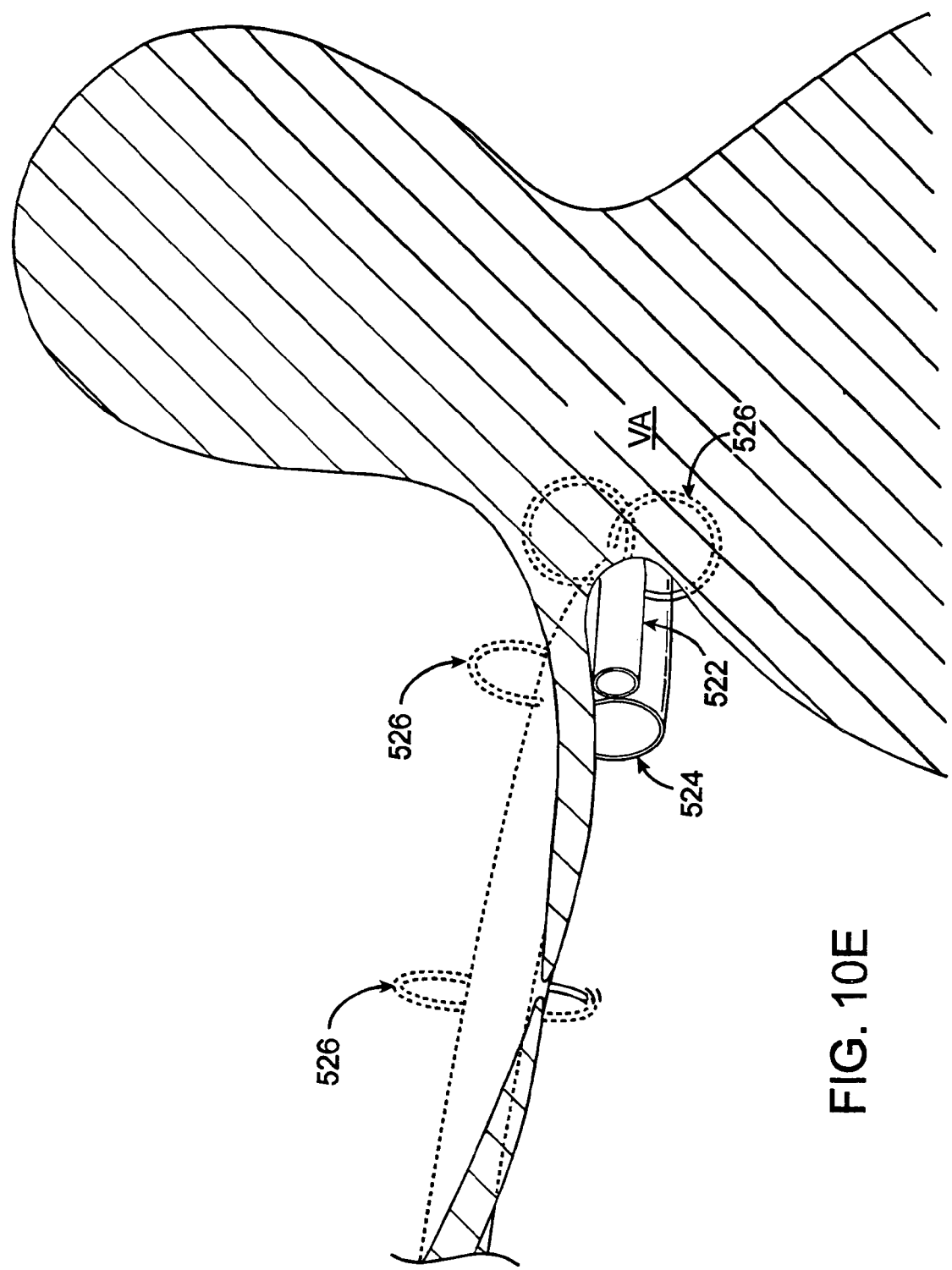

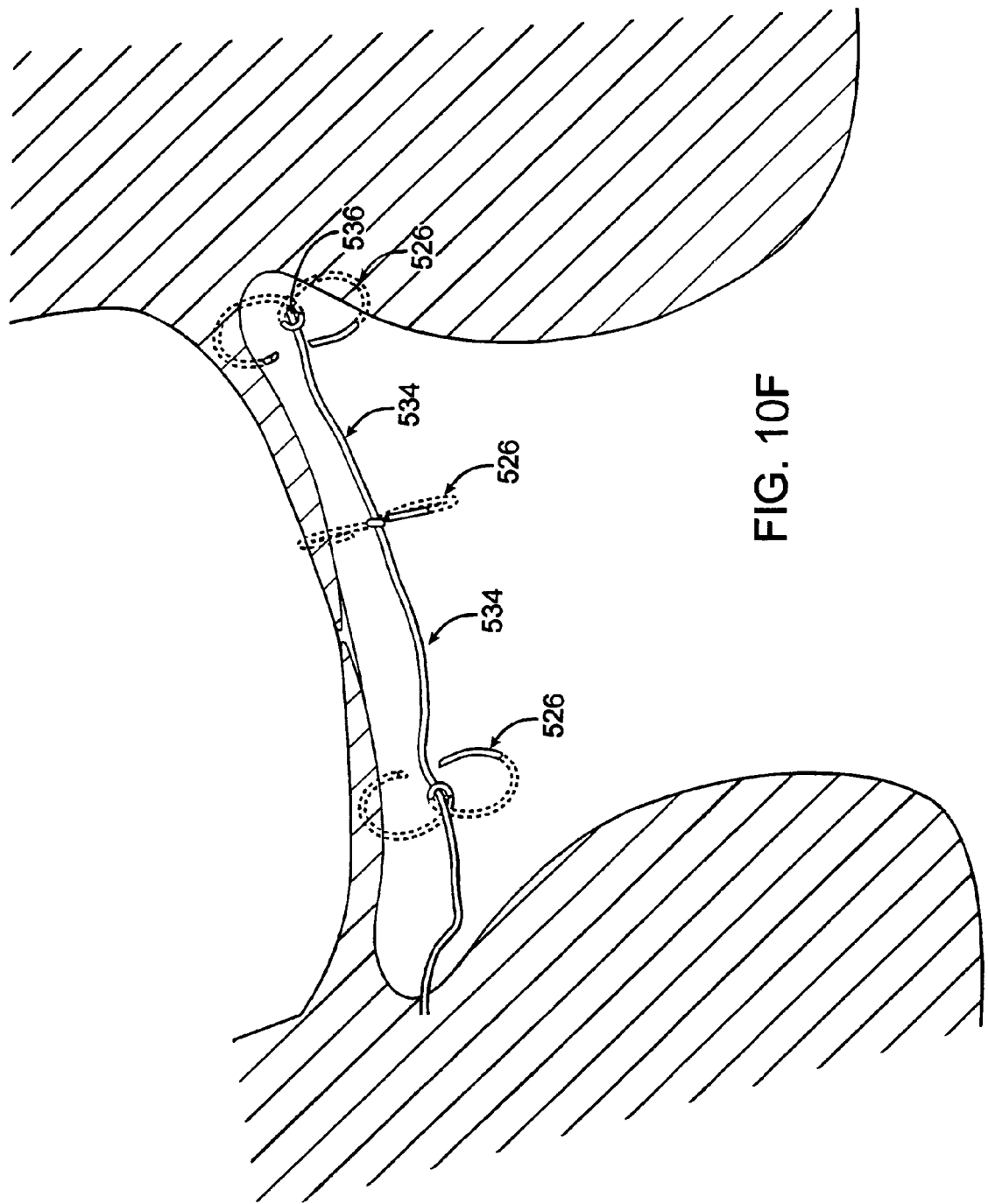

DELIVERY DEVICES AND METHODS FOR HEART VALVE REPAIR

CROSS REFERENCE TO RELATED APPLICATIONS

The present application is a continuation-in-part of U.S. patent application Ser. No. 10/792,681, filed on Mar. 2, 2004, now abandoned, which is a continuation-in-part of U.S. patent application Ser. No. 10/741,130, filed on Dec. 19, 2003, now U.S. Pat. No. 8,287,555, which claims the benefit of U.S. Provisional Patent Application Nos. 60/459,735, filed on Apr. 1, 2003 and 60/524,922, filed on Nov. 24, 2003, and which is a continuation-in-part of U.S. patent application Ser. No. 10/656,797, filed on Sep. 4, 2003, now U.S. Pat. No. 7,753,922 and Ser. No. 10/461,043, filed on Jun. 13, 2003, now U.S. Pat. No. 6,986,775, the latter of which claims the benefit of U.S. Provisional Patent Application Nos. 60/388,935, filed on Jun. 13, 2002; 60/429,288, filed on Nov. 25, 2002; 60/445,890, filed on Feb. 6, 2003; and 60/462,502, filed on Apr. 10, 2003. The full disclosures of all the above-listed references are hereby incorporated by reference.

The present application is related to U.S. patent application Ser. No. 10/901,019, filed on Jul. 27, 2004; Ser. No. 10/900,980, filed on Jul. 27, 2004; Ser. No. 10/901,444, filed on Jul. 27, 2004; Ser. No. 10/901,455 filed on Jul. 27, 2004; and Ser. No. 10/901,555, filed on Jul. 27, 2004, all of which are hereby fully incorporated by reference.

BACKGROUND OF THE INVENTION

1. Field of the Invention

The present invention relates generally to medical devices and methods. More particularly, the invention relates to devices, systems and methods for enhancing cardiovascular valve repair, especially the repair of heart valves such as the mitral and tricuspid valves.

In recent years, many advances have been made to reduce the invasiveness of cardiac surgery. In an attempt to avoid open, stopped-heart procedures, which may be accompanied by high patient morbidity and mortality, many devices and methods have been developed for operating on a heart through smaller incisions, operating on a beating heart, and even performing cardiac procedures via transvascular access. Different types of cardiac procedures, such as cardiac ablation techniques for treating atrial fibrillation, stenting procedures for atherosclerosis, and valve repair procedures for treating conditions such as mitral valve regurgitation have experienced significant technological advances. In implementing many minimally invasive cardiac surgery techniques, especially beating-heart techniques, one of the most significant challenges is positioning a treatment device (or multiple devices) in a desired location in or around the heart for performing the procedure. Another challenge, once a device is positioned, is to effectively deploy a given treatment into or on the target cardiac tissue.

One type of cardiac surgery which may benefit from less invasive techniques is heart valve repair. Traditional treatment of heart valve stenosis or regurgitation, such as mitral or tricuspid regurgitation, typically involves an open-heart surgical procedure to replace or repair the valve. Valve repair procedures typically involve annuloplasty, a set of techniques designed to restore the valve annulus shape and strengthen the annulus. Conventional annuloplasty surgery generally requires a large incision into the thorax of the patient (a thoracotomy), and sometimes a median sternotomy (cutting through the middle of the sternum). These open heart, open chest procedures routinely involve placing the patient on a cardiopulmonary bypass machine for sustained periods so that the patient's heart and lungs can be artificially stopped during the procedure. Finally, valve repair and replacement procedures are typically technically challenging and require a relatively large incision through the wall of the heart to access the valve.

Due to the highly invasive nature of open heart valve repair or replacement, many patients, such as elderly patients, patients having recently undergone other surgical procedures, patients with comorbid medical conditions, children, late-stage heart failure patients, and the like, are often considered too high-risk to undergo heart valve surgery and are relegated to progressive deterioration and cardiac enlargement. Often, such patients have no feasible alternative treatments for their heart valve conditions.

To obviate this situation, a number of devices and methods for repairing cardiac valves in a less invasive manner have been described. Some devices provide for heart valve repair through minimally invasive incisions or intravascularly, while others improve upon open heart surgical procedures on beating hearts, stopped hearts or both. As mentioned above, difficulties in performing minimally invasive intracardiac surgery include positioning a minimally invasive treatment device in a desired location for performing a procedure and effectively deploying a given treatment into or on the target cardiac tissue. In heart valve repair procedures, for example, it is often essential for a physician to secure one or more treatment devices to valve annulus tissue. Annular tissue tends to be more fibrous than surrounding muscular or valve leaflet tissue, thus providing a more suitable location for securing such treatment devices, such as anchors, to treat a heart valve. Positioning an anchor deliver device in a desired location adjacent the annular tissue may often be challenging, especially in an intravascular procedure when visualization of the location is limited.

Devices and methods that address these difficulties are described in U.S. patent application Ser. Nos. 10/792,681, 10/741,130, 10/656,797, 10/461,043, 60/388,935, 60/429,288, 60/445,890, 60/462,502 and 60/524,622, which were previously incorporated by reference. For example, these references describe devices and methods for exposing, stabilizing and/or performing a procedure on a heart valve annulus, such as a mitral valve annulus. Many of the devices and methods previously described by the inventors have been found to be highly effective, but improvements are still being sought.

Therefore, it would be beneficial to have improved methods, devices and systems for enhancing heart valve annulus treatment procedures. Ideally, such methods, devices and systems would facilitate positioning of one or more devices in a left ventricle or elsewhere for performing a procedure on a heart valve annulus, visualizing the annulus and/or the like. Additionally, such methods, devices and systems would ideally be introduced intravascularly. At least some of these objectives will be met by the present invention.

2. Description of the Background Art

Published U.S. application Nos. 2002/0156526, 2003/0220685, 2004/0019378, 2004/0003819, 2004/0030382 and 2004/0039442, and U.S. Pat. Nos. 6,629,534 and 6,619,291 describe catheter-based methods for performing annuloplasty. Published U.S. application 2002/0042621 describes a heart valve annuloplasty system with constrictable plication bands which are optionally attached to a linkage strip. Published U.S. application 2002/0087169 describes a remote controlled catheter system which can be used to deliver anchors and a tether for performing an annuloplasty procedure. Other patent publications of interest include WO01/26586; US2001/0005787; US2001/0014800; US2002/0013621; US2002/0029080; US2002/0035361; US2002/0042621; US2002/0095167; and US2003/0074012. U.S. patents of interest include U.S. Pat. Nos. 4,014,492; 4,042,979; 4,043,504; 4,055,861; 4,700,250; 5,366,479; 5,450,860; 5,571,215; 5,674,279; 5,709,695; 5,752,518; 5,848,969; 5,860,992; 5,904,651; 5,961,539; 5,972,004; 6,165,183; 6,197,017; 6,250,308; 6,260,552; 6,283,993; 6,269,819; 6,312,447; 6,332,893; and 6,524,338. Publications of interest include De Simone et al. (1993) *Am. J. Cardiol.* 73:721-722, and Downing et al. (2001) *Heart Surgery Forum*, Abstract 7025. All of the above cited references are hereby incorporated by reference in the present application.

BRIEF SUMMARY OF THE INVENTION

Devices, systems and methods of the present invention are generally used to facilitate transvascular, minimally invasive and other "less invasive" surgical procedures, by facilitating the delivery of treatment devices at a treatment site. "Less invasive," for the purposes of this application, means any procedure that is less invasive than traditional, large-incision, open surgical procedures. Thus, a less invasive procedure may be an open surgical procedure involving one or more relatively small incisions, a procedure performed via transvascular percutaneous access, a transvascular procedure via cut-down, a laparoscopic or other endoscopic procedure, or the like. Generally, any procedure in which a goal is to minimize or reduce invasiveness to the patient may be considered less invasive. Furthermore, although the terms "less invasive" and "minimally invasive" may sometimes be used interchangeably in this application, neither these nor terms used to describe a particular subset of surgical or other procedures should be interpreted to limit the scope of the invention. Generally, devices and methods of the invention may be used in performing or enhancing any suitable procedure.

The present application typically describes devices, systems and methods for performing heart valve repair procedures, and more specifically heart valve annuloplasty procedures such as mitral valve annuloplasty to treat mitral regurgitation. Devices and methods of the invention, however, may be used in any suitable procedure, both cardiac and non-cardiac. For example, they may be used in procedures to repair any heart valve, to repair an atrial-septal defect, to access and possibly perform a valve repair or other procedure from (or through) the coronary sinus, to place one or more pacemaker leads, to perform a cardiac ablation procedure such as ablating around pulmonary veins to treat atrial fibrillation, and/or the like. In other embodiments, the devices and methods may be used to enhance a laparoscopic or other endoscopic procedure on any part of the body, such as the bladder, stomach, gastroesophageal junction, vasculature, gall bladder, or the like. Therefore, although the following description typically focuses on mitral valve and other heart valve repair, such description should not be interpreted to limit the scope of the invention as defined by the claims.

That being said, the present invention generally provides devices, systems and methods for enhanced treatment of a cardiac valve annulus such as a mitral valve annulus. Methods generally involve contacting an anchor delivery device with a length of a valve annulus, delivering a plurality of coupled anchors from the anchor delivery device to secure the anchors to the annulus, and drawing the anchors together to circumferentially tighten the annulus. One device generally includes an elongate catheter having a housing at or near the distal end for releasably housing a plurality of coupled anchors. The device may be positioned such that the housing abuts or is close to valve annular tissue, such as at an intersection of the left ventricular wall and one or more mitral valve leaflets of the heart. Some embodiments include self-securing anchors, which may change from undeployed to deployed configurations. Anchors may be drawn together to tighten the annulus by cinching a tether slidably coupled with the anchors and/or by a self-deforming member coupled with the anchors. Another device includes a steerable guide catheter for helping position the anchor delivery device for treating a valve annulus.

In many cases, methods of the present invention will be performed on a beating heart. Access to the beating heart may be accomplished by any available technique, including intravascular, transthoracic, and the like. Intravascular access to a heart valve may be achieved using any suitable route or method. To perform a procedure on a mitral valve, for example, in one embodiment a catheter may be advanced through a femoral artery, to the aorta, and into the left ventricle of the heart, to contact a length of the mitral valve. Alternatively, access may be gained through the venous system, to a central vein, into the right atrium of the heart, and across the interatrial septum to the left side of the heart to contact a length of the mitral valve. In either of these two types of intravascular access, the catheter will often easily be advanced, once it enters the left side of the heart, into a space defined by the left ventricular wall, one or more mitral valve leaflets, and chordae tendineae of the left ventricle. This space provides a convenient conduit for further advancement of the catheter to a desired location for performing mitral valve repair. In alternative embodiments, a catheter device may access the coronary sinus and a valve procedure may be performed directly from the sinus. Furthermore, in addition to beating heart access, methods of the present invention may be used for intravascular stopped heart access as well as stopped heart open chest procedures. Any suitable intravascular or other access method is contemplated within the scope of the invention.

In one aspect of the present invention, a method for advancing an operational device into a left ventricle of a heart to contact the mitral valve annulus comprises: advancing an operational device into a left ventricle and along at least a portion of a mitral valve annulus of a heart; urging the operational device radially outwardly to seat the operational device against the mitral valve annulus; the urging step being carried out at least in part by virtue of the operational device having a radius of curvature when in an expanded state larger than the radius of curvature of the mitral valve annulus; and acting on the mitral valve annulus by the operational device. In some embodiments, the radius of curvature of the operational device in the expanded state is about 25%-50% larger than the radius of curvature of the mitral valve annulus. Also in some embodiments, the advancing step is carried out in a retrograde manner into the left ventricle. For example, the advancing step may involve passing the operational device through the aorta.

In one embodiment, the urging step further comprises radially outwardly expanding an expansible element associated with the operational device. For example the radially outwardly expanding step may be carried out with an expansible element having a radius larger than the radius of the operational device. In some embodiments, the urging step further comprises radially outwardly expanding a balloon associated with the operational device. Optionally, in some embodiments the urging step is carried out with an operational device having a length to seat the entire length of the operational device against the mitral valve annulus. The urging step may further comprise magnetically urging the operational device towards the mitral valve annulus. In some embodiments, the operational device advancing step is carried out using a steerable operational device.

In some embodiments, the operational device advancing step comprises: advancing a guide catheter into a left ventricle and along at least a portion of a mitral valve annulus of a heart; passing a flexible guide sheath over the guide catheter and along at least a portion of the mitral valve annulus; and advancing the operational device through the guide sheath. Optionally, the method may further include withdrawing the guide catheter from the guide sheath before advancing the operational device through the guide sheath. Some embodiments further include removing the guide sheath from the mitral valve annulus before the acting on step. In some embodiments the guide catheter advancing step is carried out using a steerable guide catheter.

In some embodiments, the acting on step comprises: securing a series of anchors of the operational device to the mitral valve annulus, the series of anchors comprising a proximal anchor coupled to a tether and a distal anchor secured to the tether; and pulling on the tether to reduce the distance between the proximal and distal anchors. Optionally, the securing step may be carried out using self-forming anchors.

In one embodiment, the advancing step is carried out using an operational device comprising: an elongate housing having a longitudinal axis and an open interior; a self-forming tissue-engageable anchor within the open interior of the housing; the anchor having a first part and a second part, the second part having a tissue-piercing tip; the housing having an opening sized for passage of the anchor tip-first through the opening; the anchor placeable in a relatively straight, undeployed state generally parallel to the longitudinal axis within the housing; and the acting on step comprises driving the anchor tip-first through the opening with the anchor naturally assuming a curved, tissue-engaging deployed state after passing through the opening in the housing. Optionally, the advancing step may be carried out using an anchor comprising said first part and two of said second parts extending from the first part. In one embodiment, the second parts extend in directions generally opposite one another when in the deployed state. Alternatively, the second parts may have generally circular or semicircular shapes when in the deployed state.

In some embodiments, the anchor is oriented generally perpendicular to the longitudinal axis when in the deployed state. The anchor may also have a generally circular or semicircular shape when in the deployed state. In some embodiments, the advancing step is carried out using an operational device comprising: a series of the anchors, the anchors comprising a distal anchor and a proximal anchor; and a tether serially coupling the anchors to one another with the proximal anchor coupled to the tether and the distal anchor secured to the tether; and the acting on step comprises: securing the series of anchors to the mitral valve annulus; and pulling on the tether to reduce the distance between the proximal and distal anchors. Some embodiments further comprise selecting an operational device comprising a housing having a diametrical dimension d and an anchor having a diametrical dimension D in the deployed state, and wherein the ratio of D to d is at least 3.5. Other embodiments further comprise selecting an operational device comprising a housing having a diametrical dimension d and an anchor having a diametrical dimension D in the deployed state, and wherein the ratio of D to d is at least 4.4. Still other embodiments further comprise selecting an operational device comprising a housing having a diametrical dimension d and an anchor having a diametrical dimension D in the deployed state, and wherein the ratio of D to d is at least 7. Alternatively, the method may further comprise selecting an operational device comprising a housing having a diametrical dimension d and an anchor having a diametrical dimension D in the deployed state, and wherein the ratio of D to d is at least 8.8.

In some embodiments, the acting on step comprises delivering anchors from a housing of the operational device into tissue at the mitral valve annulus. In one embodiment, the anchors delivering step is carried out using a series of tethered anchors, comprising a tether and said anchors, and the acting on step further comprises circumferentially tightening the mitral valve annulus by placing the tether in tension. Optionally, the anchors delivering step may comprise driving at least one of the anchors through a biocompatible material thereby attaching the biocompatible material to the mitral valve annulus. In some embodiments, the anchor delivering step is carried out using a strip of the biocompatible material and the anchors driving step comprises driving a plurality of the anchors through the strip of biocompatible material. In some embodiments, the anchor delivering step is carried out using a plurality of pieces of the biocompatible material, and the anchors driving step comprises driving a plurality of the anchors through the pieces of biocompatible material.

In some embodiments, the advancing step comprises advancing the operational device through a guide sheath. The acting on step may also comprise delivering anchors from a housing of the operational device, through a distal portion of the guide sheath and into tissue at the mitral valve annulus thereby attaching the distal portion of the guide sheath to the mitral valve annulus. Optionally, the method may also comprise detaching the distal portion of the guide sheath from a proximal portion of the guide sheath. In some embodiments, the acting on step comprises delivering anchors from a housing of the operational device, through a distal portion of the operational device and into tissue at the mitral valve annulus thereby attaching the distal portion of the operational device to the mitral valve annulus, and further comprising detaching the distal portion of the operational device from a proximal portion of the operational device.

In another aspect of the present invention, a method for advancing an operational device into a left ventricle of a heart to contact the mitral valve annulus comprises: advancing an operational device into a left ventricle and along at least a portion of a mitral valve annulus of a heart, the operational device comprising an expansible element; the operational device advancing step comprising steering the operational device; radially outwardly expanding the expansible element to urge the operational device radially outwardly to seat the operational device against the mitral valve annulus; and acting on the mitral valve annulus by the operational device. In some embodiments, the advancing step is carried out in a retrograde manner into the left ventricle. For example, the advancing step may comprise passing the operational device through the aorta.

In some embodiments, the radially outwardly expanding step is carried out with an expansible element having a radius larger than the radius of the operational device. Also in some embodiments, the urging step may be carried out with a balloon as the expansible element. The acting on step may optionally involve: securing a series of anchors of the operational device to the mitral valve annulus, the series of anchors comprising a proximal anchor coupled to a tether and a distal anchor secured to the tether; and pulling on the tether to reduce the distance between the proximal and distal anchors. The securing step may be carried out, for example, using self-forming anchors. In other embodiments, the acting on step may involve delivering anchors from a housing of the operational device into tissue at the mitral valve annulus. For example, in one embodiment the anchors delivering step is carried out using a series of tethered anchors, comprising a tether and said anchors, and the acting on step further comprises circumferentially tightening the mitral valve annulus by placing the tether in tension.

In some embodiments, the acting on step comprises delivering anchors from a housing of the operational device, through a distal portion of the operational device and into tissue at the mitral valve annulus thereby attaching the distal portion of the operational device to the mitral valve annulus, and further comprising detaching the distal portion of the operational device from a proximal portion of the operational device. In some embodiments, the advancing step is carried out using the operational device as the only steerable element.

In another aspect of the invention, a method for advancing an operational device into a left ventricle of a heart to contact the mitral valve annulus comprises: advancing a guide catheter into a left ventricle and along at least a portion of a mitral valve annulus of a heart, the mitral valve annulus having a mitral valve annulus radius; selecting a flexible guide sheath having a curveable portion, said curveable portion having a guide sheath radius when in an outwardly expanded curved state, the guide sheath radius being larger than the mitral valve annulus radius; passing the guide sheath over the guide catheter and along at least a portion of the mitral valve annulus; urging the curveable portion of the guide sheath in the curved state towards the mitral valve annulus at least in part by virtue of the guide sheath radius; advancing an operational device through the guide sheath; and acting on the mitral valve annulus by the operational device. In some embodiments, the guide sheath radius is about 25%-50% larger than the mitral valve annulus radius. In some embodiments, the guide catheter advancing step is carried out using a steerable guide catheter.

In one embodiment, the method further comprises withdrawing the guide catheter from the guide sheath before the operational device advancing step. Some embodiments further comprise removing the guide sheath from the mitral valve annulus before the acting on step. The acting on step may optionally include urging the operational device radially outwardly to engage the mitral valve annulus. In some embodiments, the acting on step comprises: securing a series of anchors of the operational device, comprising a proximal anchor coupled to a tether and a distal anchor secured to the tether, to the mitral valve annulus; and pulling on the tether to reduce the distance between the proximal and distal anchors. In some embodiments, the securing step is carried out using self-forming anchors.

In another aspect of the present invention, a method for advancing an operational device into a left ventricle of a heart to contact the mitral valve annulus comprises: selecting a flexible guide catheter having a curveable portion, said curveable portion having a guide catheter radius when in outwardly expanded curved state; advancing the guide catheter into a left ventricle and along at least a portion of a mitral valve annulus of a heart, the mitral valve annulus having a mitral valve annulus radius; the selecting step being carried out with the guide catheter radius being larger than the mitral valve annulus radius; passing a curveable portion of the a guide sheath over the guide catheter and along at least a portion of the mitral valve annulus; urging the curveable portion of the guide sheath towards the mitral valve annulus at least in part by virtue of the guide catheter radius; advancing an operational device through the guide sheath; and acting on the mitral valve annulus by the operational device.

In some embodiments, the guide catheter radius is about 25%-50% larger than the mitral valve annulus radius. Optionally, the guide catheter advancing step is carried out using a steerable guide catheter. The method may further include withdrawing the guide catheter from the guide sheath before the operational device advancing step. The method may also include removing the guide sheath from the mitral valve annulus before the acting on step. In some embodiments, the acting on step comprises urging the operational device radially outwardly to engage the mitral valve annulus. In some embodiments, the acting on step comprises: securing a series of anchors of the operational device, comprising a proximal anchor coupled to a tether and a distal anchor secured to the tether, to the mitral valve annulus; and pulling on the tether to reduce the distance between the proximal and distal anchors. In one embodiment, the securing step is carried out using self-forming anchors.

These and other aspects and embodiments are described more fully below with reference to the drawing figures.

BRIEF DESCRIPTION OF THE DRAWINGS

FIGS. 10A-10F demonstrate a method for applying anchors to a valve annulus and cinching the anchors to tighten the annulus, using an anchor delivery device according to an embodiment of the invention;

DETAILED DESCRIPTION OF THE INVENTION

Devices, systems and methods of the present invention are generally used to facilitate transvascular, minimally invasive and other "less invasive" surgical procedures, by facilitating the delivery of treatment devices at a treatment site. Although the following description focuses on use of devices and methods of the invention for mitral valve repair, the devices and methods may be used in any suitable procedure, both cardiac and non-cardiac. When used for treatment of a cardiac valve annulus, the inventive methods generally involve contacting an anchor delivery device with a length of the valve annulus, delivering a plurality of coupled anchors from the anchor delivery device, and drawing the anchors together to tighten the annulus. Devices include an elongate catheter having a housing at or near the distal end for releasably housing a plurality of coupled anchors, as well as delivery devices for facilitating advancement and/or positioning of an anchor delivery device. Devices may be positioned such that the housing abuts or is close to valve annular tissue, such as in a location within the left ventricle defined by the left ventricular wall, a mitral valve leaflet and chordae tendineae. Self-securing anchors having any of a number of different configurations may be used in some embodiments. Additional devices include delivery devices for facilitating delivery and/or placement of an anchor delivery device at a treatment site.

In many cases, methods of the present invention will be performed on a beating heart. Access to the beating heart may be accomplished by any available technique, including intravascular, transthoracic, and the like. In addition to beating heart access, the methods of the present invention may be used for intravascular stopped heart access as well as stopped heart open chest procedures.

Figure 1:
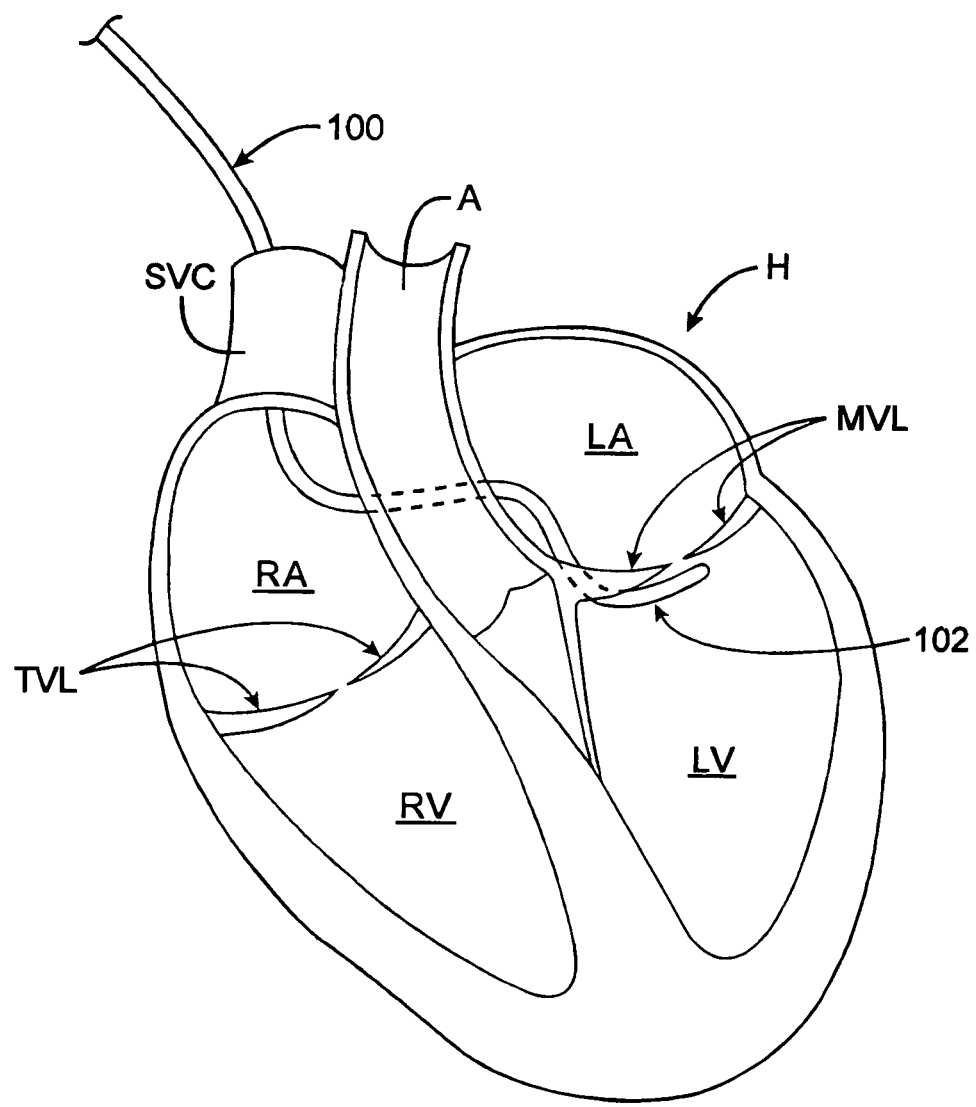
FIG. 1 is a cross-sectional view of a heart with a flexible anchor delivery device being positioned for treatment of a mitral valve annulus, according to one embodiment of the present invention.

Referring now to FIG. 1, a heart H is shown in cross section, with an elongate anchor delivery device 100 introduced within the heart H. Generally, delivery device 100 comprises an elongate body with a distal portion 102 configured to deliver anchors to a heart valve annulus. (In FIGS. 1, 2A and 2B, distal portion 102 is shown diagrammatically without anchors or anchor-delivery mechanism to enhance clarity of the figures.) In some embodiments, the elongate body comprises a rigid shaft, while in other embodiments it comprises a flexible catheter, so that distal portion 102 may be positioned in the heart H and under one or more valve leaflets to engage a valve annulus via a transvascular approach. Transvascular access may be gained, for example, through the internal jugular vein (not shown) to the superior vena cava SVC to the right atrium RA, across the interatrial septum to the left atrium LA, and then under one or more mitral valve leaflets MVL to a position within the left ventricle (LV) under the valve annulus (not shown). Alternatively, access to the heart may be achieved via the femoral vein and the inferior vena cava. In other embodiments, access may be gained via the coronary sinus (not shown) and through the atrial wall into the left atrium. In still other embodiments, access may be achieved via a femoral artery and the aorta, into the left ventricle, and under the mitral valve. This access route will be described in further detail below. Any other suitable access route is also contemplated within the scope of the present invention.

In other embodiments, access to the heart H may be transthoracic, with delivery device 100 being introduced into the heart via an incision or port on the heart wall. Even open heart surgical procedures may benefit from methods and devices of the invention. Furthermore, some embodiments may be used to enhance procedures on the tricuspid valve annulus, adjacent the tricuspid valve leaflets TVL, or any other cardiac or vascular valve. Therefore, although the following description typically focuses on minimally invasive or less invasive mitral valve repair for treating mitral regurgitation, the invention is in no way limited to that use.

Figure 2A:
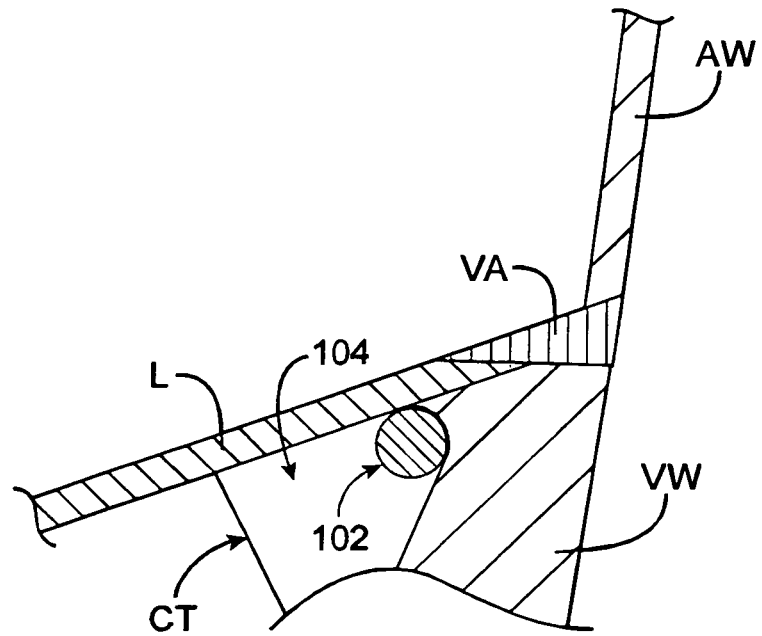
FIGS. 2A and 2B are cross-sectional views of a portion of a heart, schematically showing positioning of a flexible device for treatment of a mitral valve annulus, according to one embodiment of the present invention.
Figure 2B:
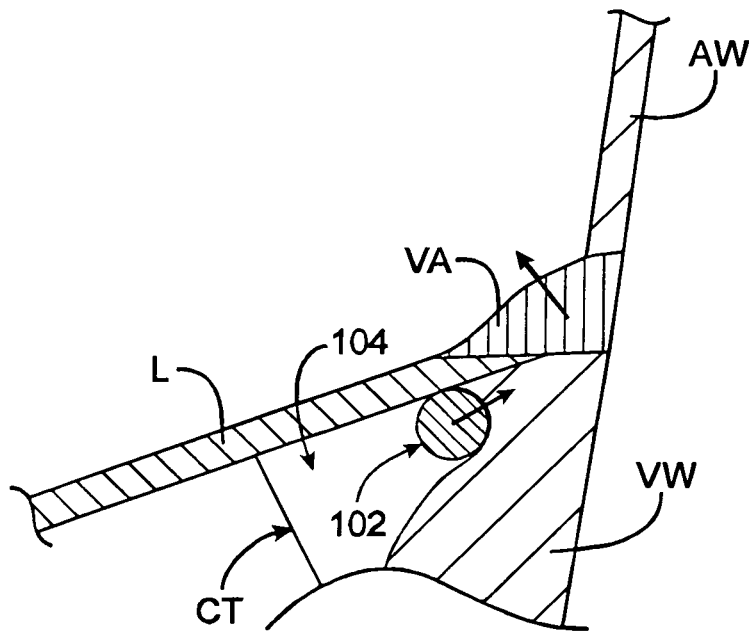

With reference now to FIGS. 2A and 2B, a method for positioning delivery device 100 for treating a mitral valve annulus VA is depicted diagrammatically in a cross-sectional view. First, as in FIG. 2A, distal portion 102 is positioned in a desired location under a mitral valve leaflet L and adjacent a ventricular wall VW. (Again, distal portion 102 is shown without anchors or anchor-delivery mechanism for demonstrative purposes.) The valve annulus VA generally comprises an area of heart wall tissue at the junction of the ventricular wall VW and the atrial wall AW that is relatively fibrous and, thus, significantly stronger that leaflet tissue and other heart wall tissue.

Distal portion 102 may be advanced into position under the valve annulus by any suitable technique, some of which are described below in further detail. Generally, distal portion 102 may be used to deliver anchors to the valve annulus, to stabilize and/or expose the annulus, or both. In one embodiment, using a delivery device having a flexible elongate body as shown in FIG. 1, a flexible distal portion 102 may be passed from the right atrium RA through the interatrial septum in the area of the foramen ovale (not shown—behind the aorta A), into the left atrium LA and thus the left ventricle LV. Alternatively, flexible distal portion 102 may be advanced through the aorta A and into the left ventricle LV, for example using access through a femoral artery. Oftentimes, distal portion 102 will then naturally travel, upon further advancement, under the posterior valve leaflet L into a space defined above a subvalvular space 104 roughly defined for the purposes of this application as a space bordered by the inner surface of the left ventricular wall VW, the inferior surface of mitral valve leaflets L, and cordae tendineae CT connected to the ventricular wall VW and the leaflet L. It has been found that a flexible anchor delivery catheter, such as the delivery devices of the present invention, when passed under the mitral valve via an intravascular approach, often enters subvalvular space 104 relatively easily and may be advanced along space 104 either partially or completely around the circumference of the valve. Once in space 104, distal portion 102 may be conveniently positioned at the intersection of the valve leaflet(s) and the ventricular wall VW, which intersection is immediately adjacent or very near to the valve annulus VA, as shown in FIG. 2A. These are but examples of possible access routes of an anchor delivery device to a valve annulus, and any other access routes may be used.

In some embodiments, distal portion 102 includes a shape-changing portion which enables distal portion 102 to conform to the shape of the valve annulus VA. The catheter may be introduced through the vasculature with the shape-changing distal portion in a generally straight, flexible configuration. Once it is in place beneath the leaflet at the intersection between the leaflet and the interior ventricular wall, the shape of distal portion 102 is changed to conform to the annulus and usually the shape is "locked" to provide sufficient stiffness or rigidity to permit the application of force from distal portion 102 to the annulus. Shaping and optionally locking distal portion 102 may be accomplished in any of a number of ways. For example, in some embodiments, a shape-changing portion may be sectioned, notched, slotted or segmented and one of more tensioning members such as tensioning cords, wires or other tensioning devices coupled with the shape-changing portion may be used to shape and rigidify distal portion 102. A segmented distal portion, for example, may include multiple segments coupled with two tensioning members, each providing a different direction of articulation to the distal portion. A first bend may be created by tensioning a first member to give the distal portion a C-shape or similar shape to conform to the valve annulus, while a second bend may be created by tensioning a second member to articulate the C-shaped member upwards against the annulus. In another embodiment, a shaped expandable member, such as a balloon, may be coupled with distal portion 102 to provide for shape changing/deforming. In various embodiments, any configurations and combinations may be used to give distal portion 102 a desired shape.

In transthoracic and other embodiments, distal portion 102 may be shaped, and the method may simply involve introducing distal portion 102 under the valve leaflets. The shaped distal portion 102 may be rigid or formed from any suitable super-elastic or shape memory material, such as nitinol, spring stainless steel, or the like.

In addition to delivering anchors to the valve annulus VA, delivery device 100 (and specifically distal portion 102) may be used to stabilize and/or expose the valve annulus VA. Such stabilization and exposure are described fully in U.S. patent application Ser. No. 10/656,797, which was previously incorporated by reference. For example, once distal portion 102 is positioned under the annulus, force may be applied to distal portion 102 to stabilize the valve annulus VA, as shown in FIG. 2B. Such force may be directed in any suitable direction to expose, position and/or stabilize the annulus. For example, upward and lateral force is shown in FIG. 2B by the solid-headed arrow drawn from the center of distal portion 102. In other cases, only upward, only lateral, or any other suitable force(s) may be applied. With application of force to distal portion 102, the valve annulus VA is caused to rise or project outwardly, thus exposing the annulus for easier viewing and access. The applied force may also stabilize the valve annulus VA, also facilitating surgical procedures and visualization.

Some embodiments may include a stabilization component as well as an anchor delivery component. For example, some embodiments may include two flexible members, one for contacting the atrial side of a valve annulus and the other for contacting the ventricular side. In some embodiments, such flexible members may be used to "clamp" the annulus between them. One of such members may be an anchor delivery member and the other may be a stabilization member, for example. Any combination and configuration of stabilization and/or anchor delivery members is contemplated.

Figure 2C:
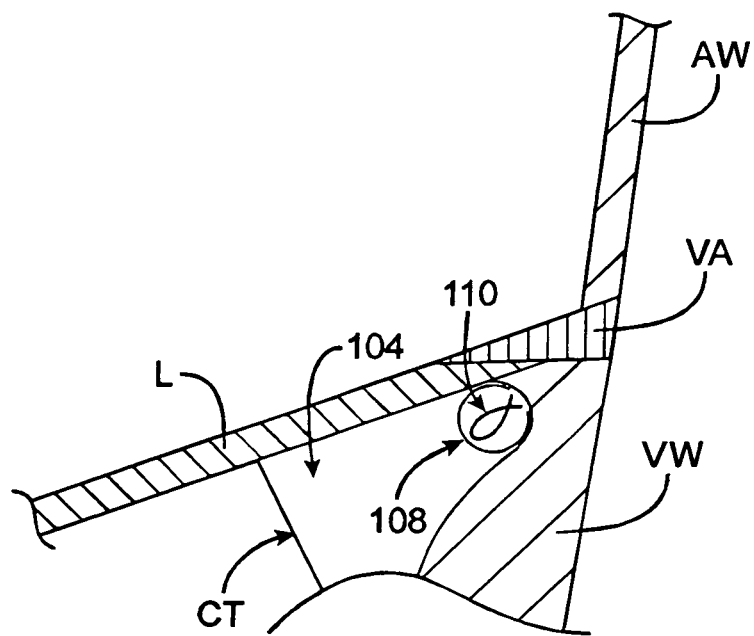
FIGS. 2C and 2D are cross-sectional views of a portion of a heart, showing positioning of a flexible anchor delivery device for treatment of a mitral valve annulus, according to one embodiment of the present invention.
Figure 2D:
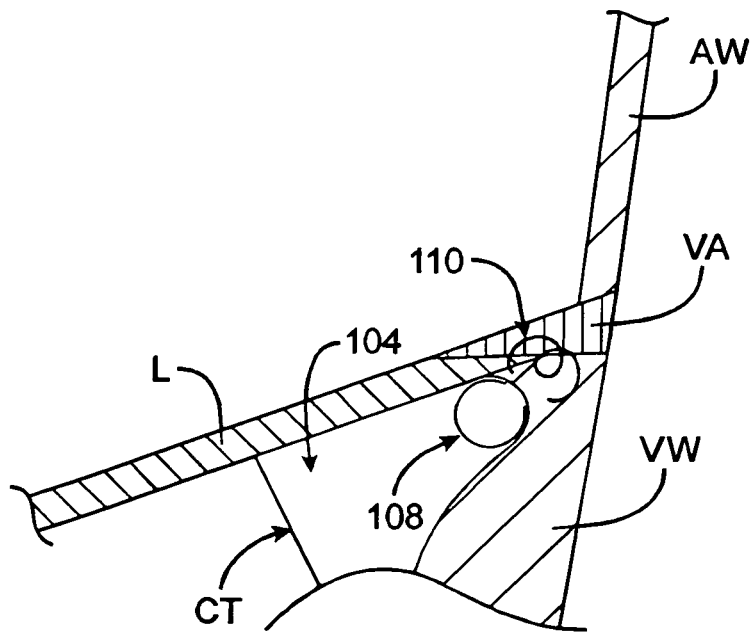

Referring now to FIGS. 2C and 2D, an anchor delivery device 108 is shown delivering an anchor 110 to a valve annulus VA. Of course, these are again representational figures and are not drawn to scale. Anchor 110 is shown first housed within delivery device 108 (FIG. 2C) and then delivered to the annulus VA (FIG. 2D). As is shown, in one embodiment anchors 110 may have a relatively straight configuration when housed in delivery device 108, perhaps with two sharpened tips and a loop in between the tips. Upon deployment from delivery device 108, the tips of anchor 110 may curve in opposite directions to form two semi-circles, circles, ovals, overlapping helices or the like. This is but one example of a type of self-securing anchor which may be delivered to a valve annulus. Typically, multiple coupled anchors 110 are delivered, and the anchors 110 are drawn together to tighten the valve annulus. Methods for anchor delivery and for drawing anchors, together are described further below.

Although delivery device 108 is shown having a circular cross-sectional shape in FIGS. 2C and 2D, it may alternatively have any other suitable shape. In one embodiment, for example, it may be advantageous to provide a delivery device having an ovoid or elliptical cross-sectional shape. Such a shape may help ensure that the device is aligned, when positioned between in a corner formed by a ventricular wall and a valve leaflet, such that one or more openings in the delivery device is oriented to deliver the anchors into valve annulus tissue. To further enhance contacting of the valve annulus and/or orientation of the delivery device, some embodiments may further include an expandable member, coupled with the delivery device, which expands to urge or press or wedge the delivery device into the corner formed by the ventricle wall and the leaflet to contact the valve annulus. Such enhancements are described further below.

Figure 3:
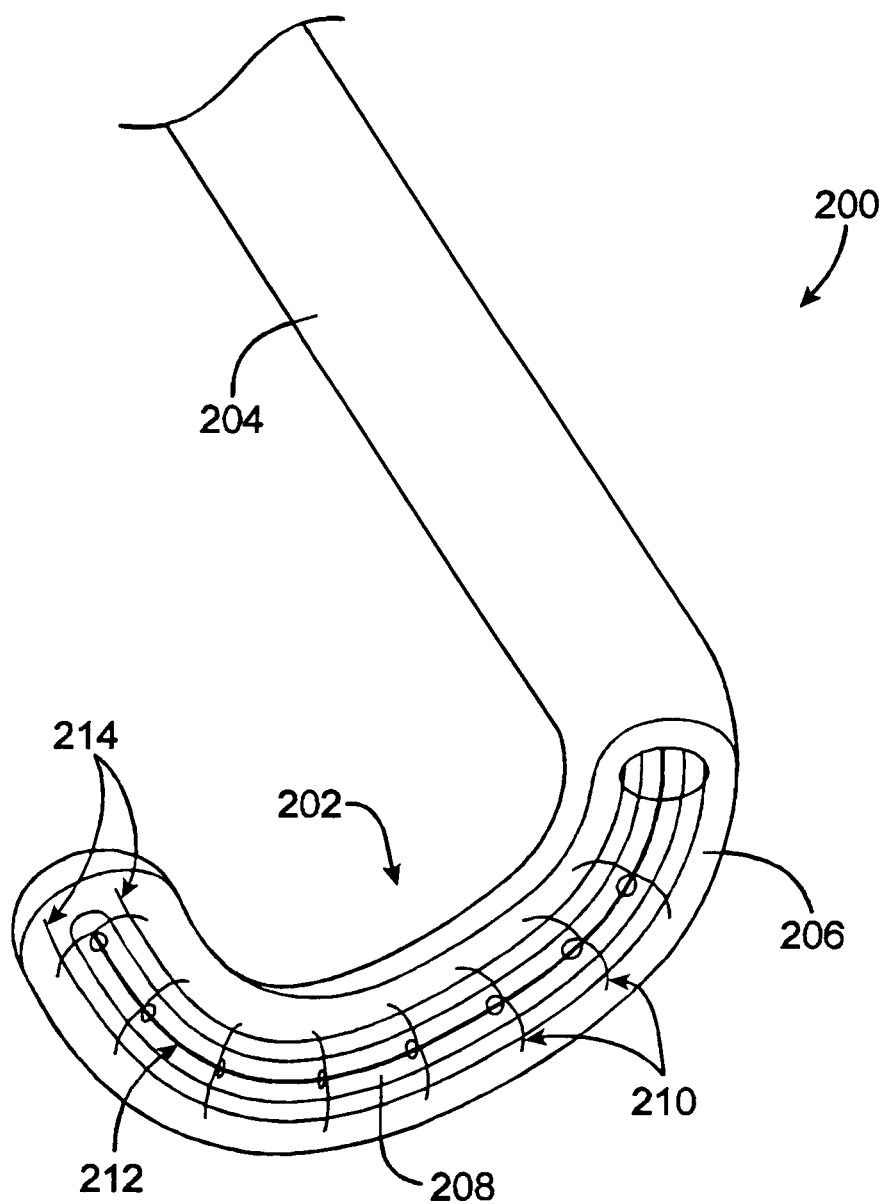
FIG. 3 is a perspective view of a distal portion of an anchor delivery device, according to one embodiment of the invention.

With reference now to FIG. 3, one embodiment of a portion of an anchor delivery device 200 suitably includes an elongate shaft 204 having a distal portion 202 configured to deliver a plurality of anchors 210, coupled with a tether 212, to tissue of a valve annulus. Tethered anchors 210 are housed within a housing 206 of distal portion 202, along with one or more anchor retaining mandrels 214 and an expandable member 208. Many variations may be made to one or more of these features, and various parts may be added or eliminated, without departing from the scope of the invention. Some of these variations are described further below, but no specific embodiment(s) should be construed to limit the scope of the invention as defined by the appended claims.

Housing 206 may be flexible or rigid in various embodiments. In some embodiments, for example, flexible housing 206 may be comprised of multiple segments configured such that housing 206 is deformable by tensioning a tensioning member coupled to the segments. In some embodiments, housing 206 is formed from an elastic material having a geometry selected to engage and optionally shape or constrict the valve annulus. For example, the rings may be formed from super-elastic material, shape memory alloy such as Nitinol, spring stainless steel, or the like. In other instances, housing 206 could be formed from an inflatable or other structure can be selectively rigidified in situ, such as a gooseneck or lockable element shaft, any of the rigidifying structures described above, or any other rigidifying structure.

"Anchors," for the purposes of this application, is defined to mean any fasteners. Thus, anchors 210 may comprise C-shaped or semicircular hooks, curved hooks of other shapes, straight hooks, barbed hooks, clips of any kind, T-tags, or any other suitable fastener(s). In one embodiment, as described above, anchors may comprise two tips that curve in opposite directions upon deployment, forming two intersecting semi-circles, circles, ovals, helices or the like. In some embodiments, anchors 210 are self-deforming. By "self-deforming" it is meant that anchors 210 change from a first undeployed shape to a second deployed shape upon release of anchors 210 from restraint in housing 206. Such self-deforming anchors 210 may change shape as they are released from housing 206 and enter valve annulus tissue, to secure themselves to the tissue. Thus, a crimping device or other similar mechanism is not required on distal end 202 to apply force to anchors 210 to attach them to annular tissue.

Self-deforming anchors 210 may be made of any suitable material, such as a super-elastic or shape-memory material like Nitinol or spring stainless steel. In other embodiments, anchors 210 may be made of a non-shape-memory material and made be loaded into housing 206 in such a way that they change shape upon release. Alternatively, anchors 210 that are not self-deforming may be used, and such anchors may be secured to tissue via crimping, firing or the like. Even self-securing anchors may be crimped in some embodiments, to provide enhanced attachment to tissue. In some embodiments, anchors 210 may comprise one or more bioactive agent. In another embodiment, anchors 210 may comprise electrodes. Such electrodes, for example, may sense various parameters, such as but not limited to impedance, temperature and electrical signals. In other embodiments, such electrodes may be used to supply energy to tissue at ablation or sub-ablation amounts. Delivery of anchors may be accomplished by any suitable device and technique, such as by simply releasing the anchors by hydraulic balloon delivery as discussed further below. Any number, size and shape of anchors 210 may be included in housing 206.

In one embodiment, anchors 210 are generally C-shaped or semicircular in their undeployed form, with the ends of the C being sharpened to penetrate tissue. Midway along the C-shaped anchor 210, an eyelet may be formed for allowing slidable passage of tether 212. To maintain anchors 210 in their C-shaped, undeployed state, anchors 210 may be retained within housing 206 by two mandrels 214, one mandrel 214 retaining each of the two arms of the C-shape of each anchor 210. Mandrels 214 may be retractable within elongate catheter body 204 to release anchors 210 and allow them to change from their undeployed C-shape to a deployed shape. The deployed shape, for example, may approximate a complete circle or a circle with overlapping ends, the latter appearing similar to a key ring. Such anchors are described further below, but generally may be advantageous in their ability to secure themselves to annular tissue by changing from their undeployed to their deployed shape. In some embodiments, anchors 210 are also configured to lie flush with a tissue surface after being deployed. By "flush" it is meant that no significant amount of an anchor protrudes from the surface, although some small portion may protrude.

Tether 212 may be one long piece of material or two or more pieces and may comprise any suitable material, such as suture, suture-like material, a Dacron strip or the like. Retaining mandrels 214 may also have any suitable configuration and be made of any suitable material, such as stainless steel, titanium, Nitinol, or the like. Various embodiments may have one mandrel, two mandrels, or more than two mandrels.

In some embodiments, anchors 210 may be released from mandrels 214 to contact and secure themselves to annular tissue without any further force applied by delivery device 200. Some embodiments, however, may also include one or more expandable members 208, which may be expanded to help drive anchors 210 into tissue. Expandable member(s) 208 may have any suitable size and configuration and may be made of any suitable material(s). Hydraulic systems such as expandable members are known in the art, and any known or as yet undiscovered expandable member may be included in housing 206 as part of the present invention.

Figure 4:
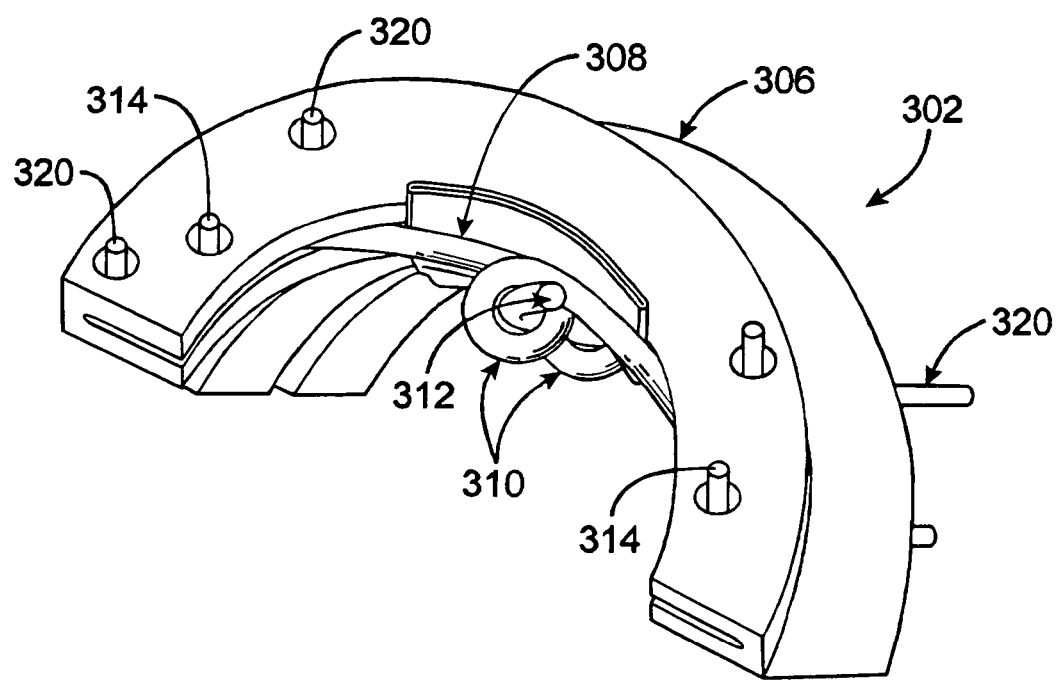
FIG. 4. is a perspective view of a segment of a distal portion of an anchor delivery device, with anchors in an undeployed shape and position.
Figure 5:
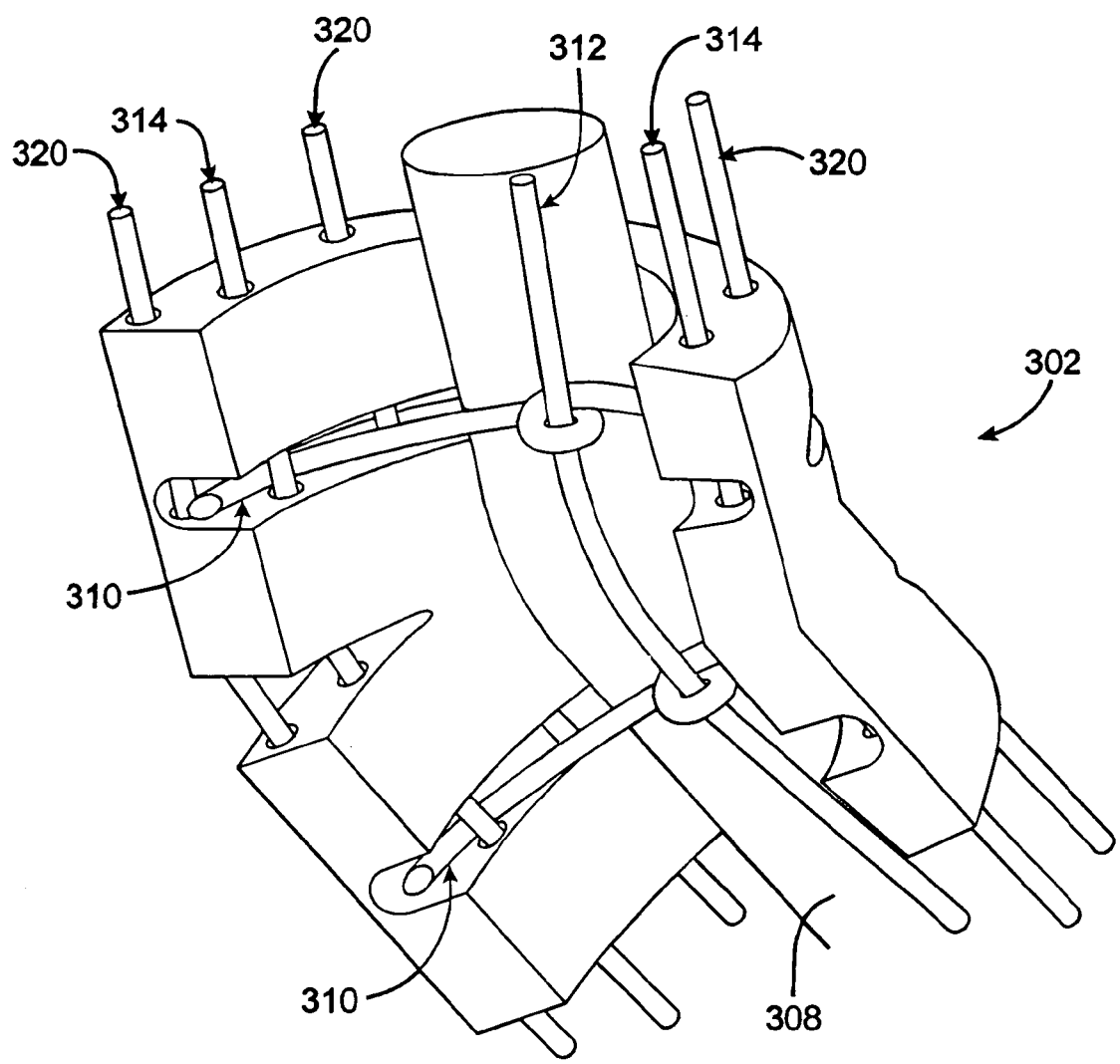
FIG. 5 is a different perspective view of the segment of the device shown in FIG. 4.

Referring now to FIGS. 4 and 5, a segment of a distal portion 302 of an anchor delivery device suitably includes a housing 306, multiple tensioning members 320 for applying tension to housing 306 to change its shape, two anchor retaining mandrels 314 slidably disposed in housing 306, multiple anchors 310 slidably coupled with a tether 312, and an expandable member 308 disposed between anchors 310 and housing 306. As can be seen in FIGS. 4 and 5, housing 306 may include multiple segments to allow the overall shape of housing 306 to be changed by applying tension to tensioning members 320. As also is evident from the drawings, "C-shaped" anchors 310 may actually have an almost straight configuration when retained by mandrels 314 in housing 306. Thus, for the purposes of this application, "C-shaped" or "semicircular" refers to a very broad range of shapes including a portion of a circle, a slightly curved line, a slightly curved line with an eyelet at one point along the line, and the like.

Figure 6:
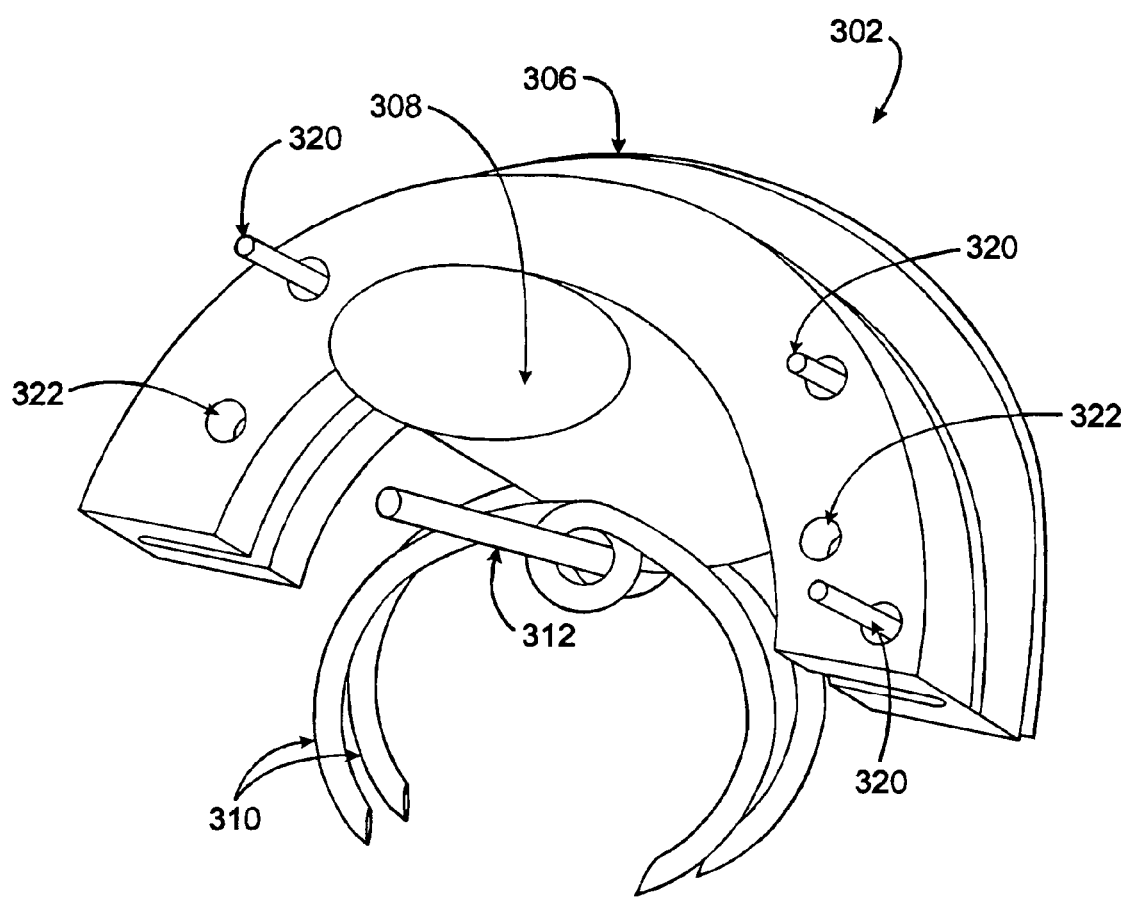
FIG. 6. is a perspective view of a segment of a distal portion of an anchor delivery device, with anchors in a deployed shape and position.

With reference now to FIG. 6, the same segment of distal portion 302 is shown, but mandrels 314 have been withdrawn from two mandrel apertures 322, to release anchors 310 from housing 306. Additionally, expandable member 308 has been expanded to drive anchors out of housing 306. Anchors 310, having been released from mandrels 314, have begun to change from their undeployed, retained shape to their deployed, released shape.

Figure 7A:
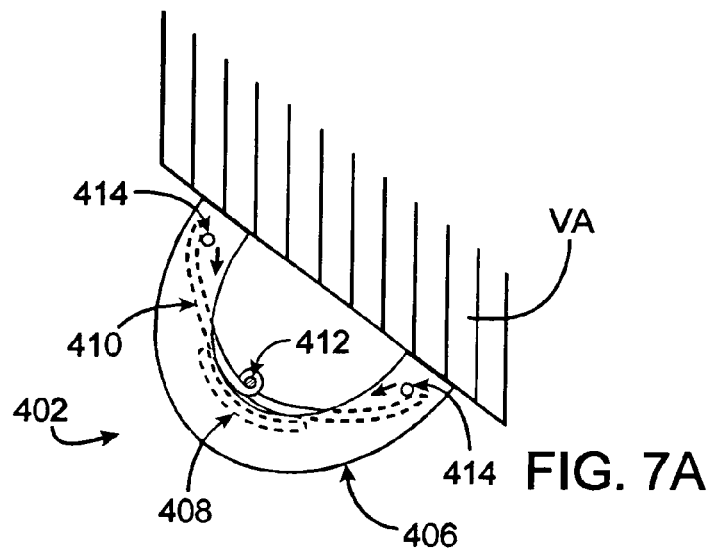
FIGS. 7A-7E are cross-sectional views of an anchor delivery device, illustrating a method for delivering anchors to valve annulus tissue, according to one embodiment of the invention.

Referring now to FIGS. 7A-7E, a cross-section of a distal portion 402 of an anchor delivery device is shown in various stages of delivering an anchor to tissue of a valve annulus VA. In FIG. 7A, distal portion 402 is positioned against the valve annulus, an anchor 410 is retained by two mandrels 414, a tether 412 is slidably disposed through an eyelet on anchor 410, and an expandable member 408 is coupled with housing 406 in a position to drive anchor 410 out of housing 406. When retained by mandrels 414, anchor 410 is in its undeployed shape. As discussed above, mandrels 414 may be slidably retracted, as designated by the solid-tipped arrows in FIG. 7A, to release anchor 410. In various embodiments, anchors 410 may be released one at a time, such as by retracting mandrels 414 slowly, may be released in groups, or may all be released simultaneously, such as by rapid retraction of mandrels 414.

Figure 7B:
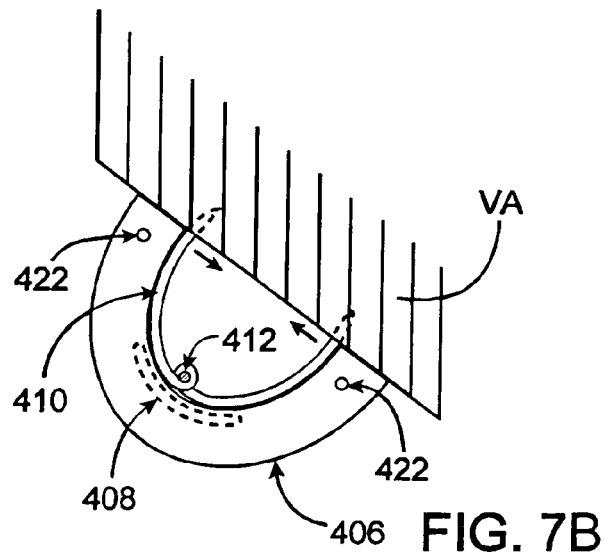
Figure 7C:
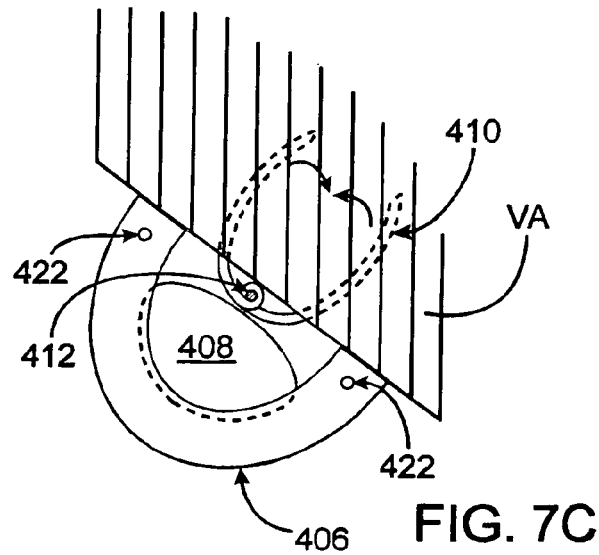
Figure 7D:
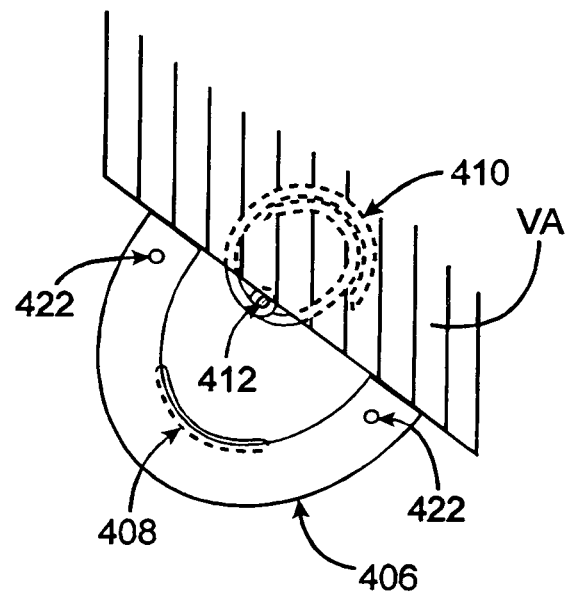
Figure 7E:
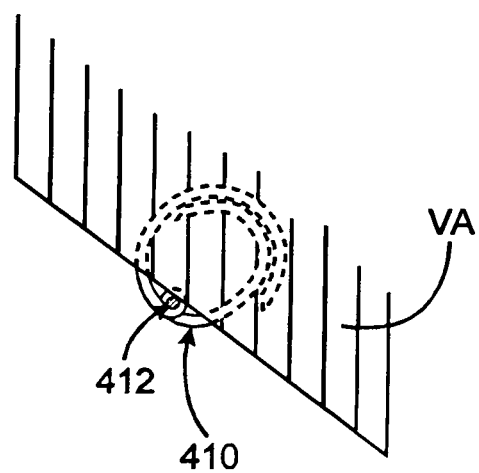

In FIG. 7B, anchor 410 has begun to change from its undeployed shape to its deployed shape (as demonstrated by the hollow-tipped arrows) and has also begun to penetrate the annular tissue VA. Empty mandrel apertures 422 demonstrate that mandrels 414 have been retracted at least far enough to release anchor 410. In FIG. 7B, expandable member 408 has been expanded to drive anchor 410 partially out of housing 406 and further into the valve annulus VA. Anchor 410 also continues to move from its undeployed towards its deployed shape, as shown by the hollow-tipped arrows. In FIG. 7D, anchor 410 has reached its deployed shape, which is roughly a completed circle with overlapping ends or a "key ring" shape. In FIG. 7E, delivery device 402 has been removed, leaving a tethered anchor in place in the valve annulus. Of course, there will typically be a plurality of tethered anchors secured to the annular tissue. Tether 412 may then be cinched to apply force to anchors 410 and cinch and tighten the valve annulus.

Figure 8A:
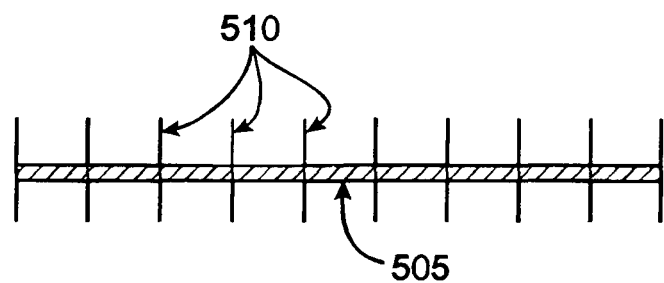
FIGS. 8A and 8B are top-views of a plurality of anchors coupled to a self-deforming coupling member or "backbone," with the backbone shown in an undeployed shape and a deployed shape.
Figure 8B:
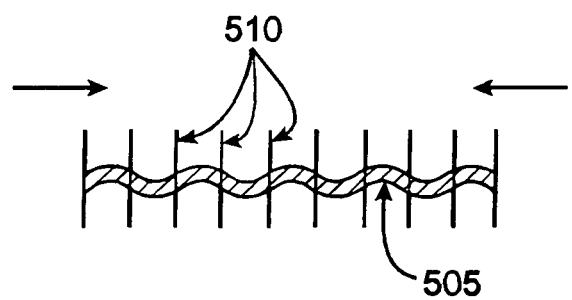

With reference now to FIGS. 8A and 8B, a diagrammatic representation of another embodiment of coupled anchors is shown. Here, anchors 510 are coupled to a self-deforming or deformable coupling member or backbone 505. Backbone 505 may be fabricated, for example, from Nitinol, spring stainless steel, or the like, and may have any suitable size or configuration. In one embodiment, as in FIG. 8A, backbone 505 is shaped as a generally straight line when held in an undeployed state, such as when restrained within a housing of an anchor deliver device. When released from the delivery device, backbone 505 may change to a deployed shape having multiple bends, as shown in FIG. 8B. By bending, backbone 505 shortens the longitudinal distance between anchors, as demonstrated by the solid-tipped arrows in FIG. 8B. This shortening process may act to cinch a valve annulus into which anchors 510 have be secured. Thus, anchors 510 coupled to backbone 505 may be used to cinch a valve annulus without using a tether or applying tethering force. Alternatively, a tether may also be coupled with anchors 510 to further cinch the annulus. In such an embodiment, backbone 505 will be at least partially conformable or cinchable, such that when force is applied to anchors 510 and backbone 505 via a tether, backbone 505 bends further to allow further cinching of the annulus.

Figure 9A:
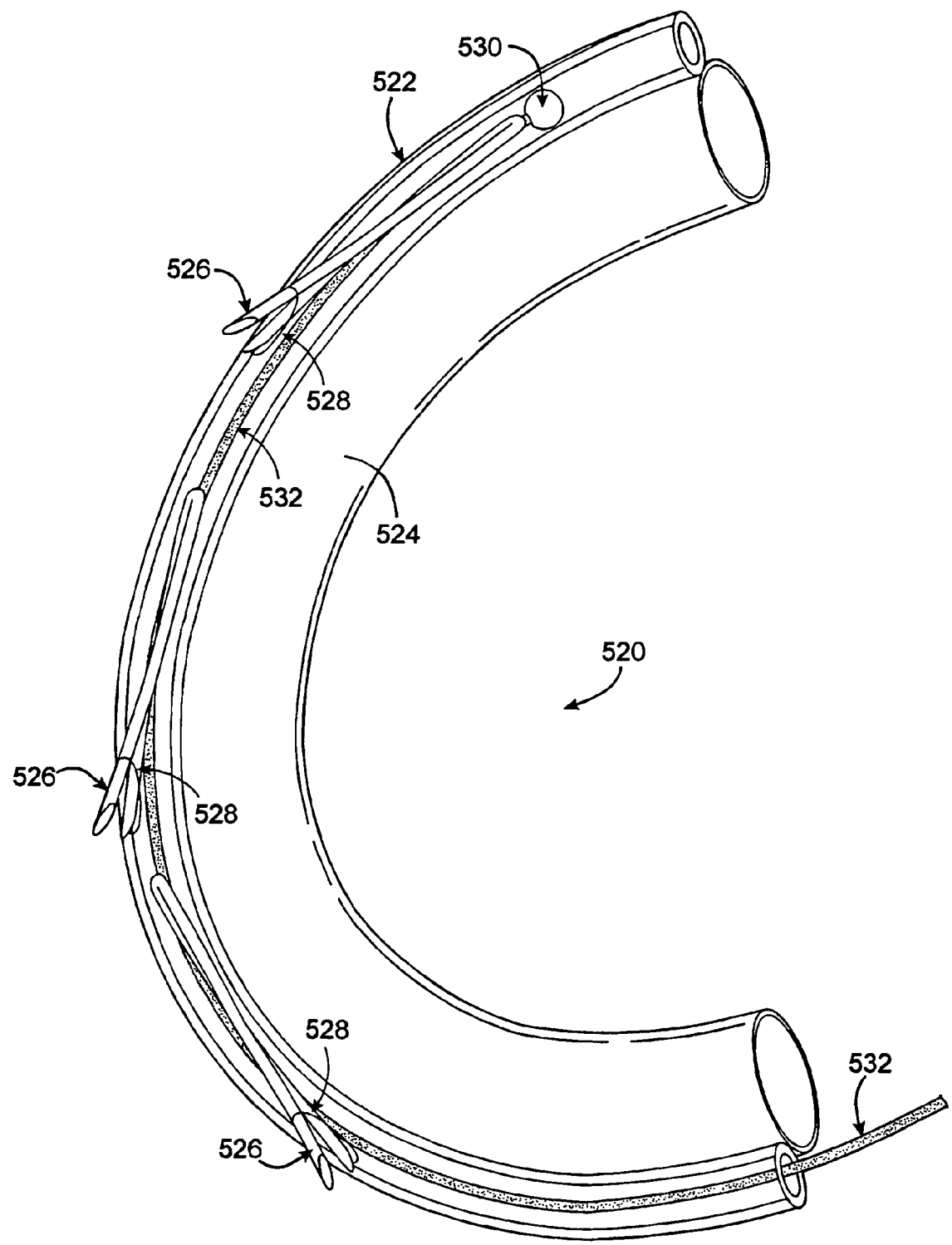
FIGS. 9A-9C are various perspective views of a distal portion of a flexible anchor delivery device according to one embodiment of the present invention.
Figure 9B:
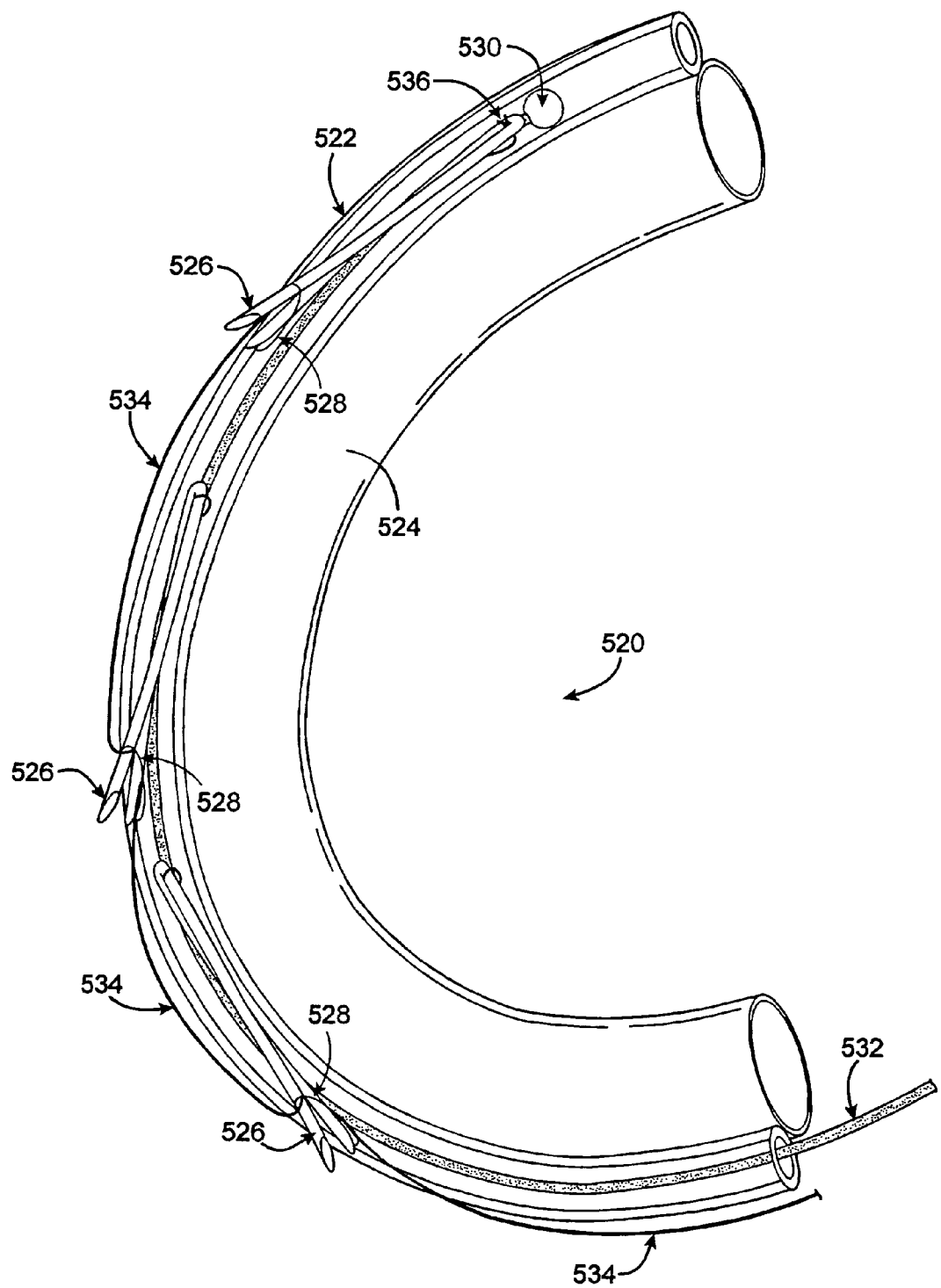
Figure 9C:
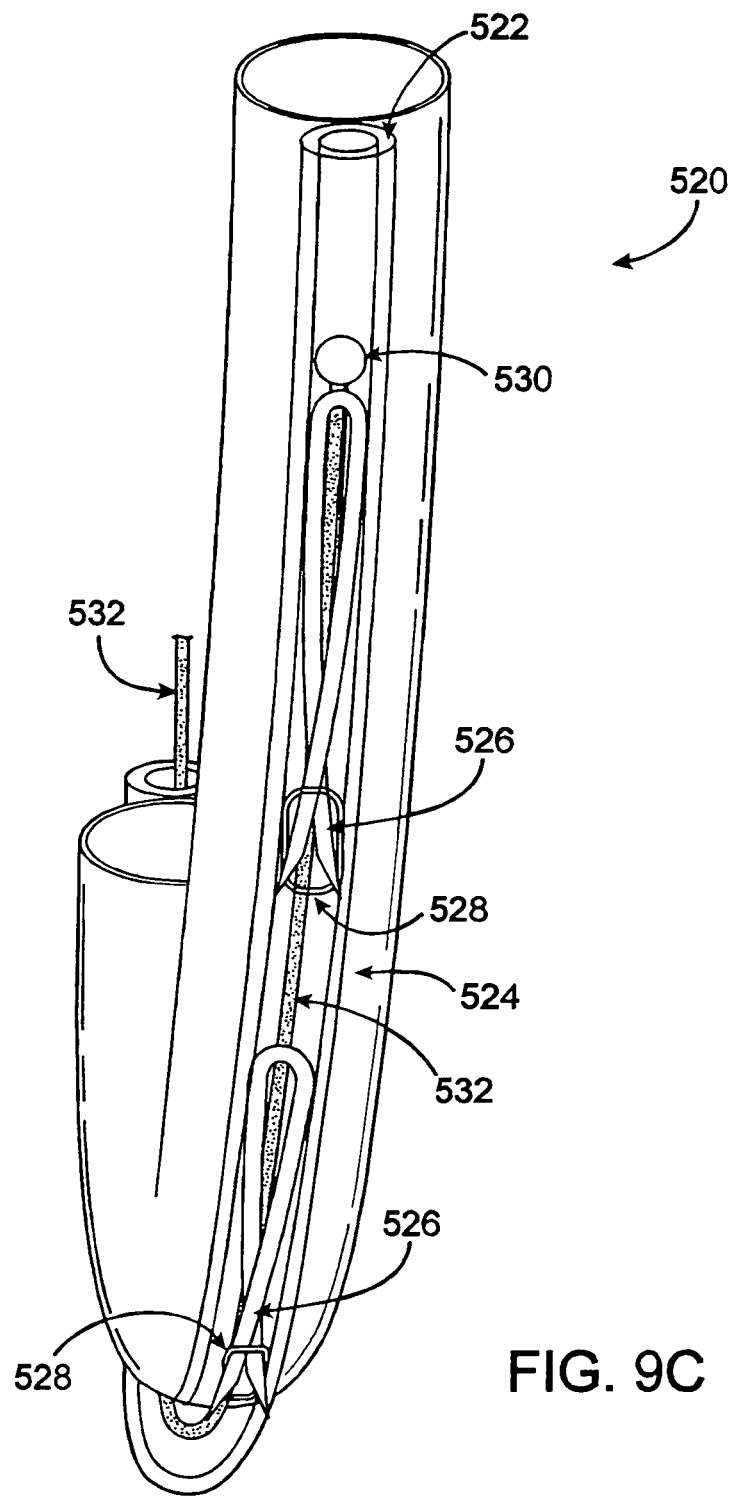

Referring now to FIGS. 9A-9C, in one embodiment a flexible distal portion of an anchor delivery device 520 suitably includes a housing 522 coupled with an expandable member 524. Housing 522 may be configured to house multiple coupled anchors 526 and an anchor contacting member 530 coupled with a pull cord 532. Housing 522 may also include multiple apertures 528 for allowing egress of anchors 526. For clarity, delivery device 520 is shown without a tether in FIGS. 9A and 9C, but FIG. 9B shows that a tether 534 may extend through an eyelet, loop or other portion of each anchor 526, and may exit each aperture 528 to allow for release of the plurality of anchors 526. The various features of this embodiment are described further below.

In the embodiment shown in FIGS. 9A-9C, anchors 526 are relatively straight and lie relatively in parallel with the long axis of delivery device 522. Anchor contacting member 530, which may comprise any suitable device, such as a ball, plate, hook, knot, plunger, piston, or the like, generally has an outer diameter that is nearly equal to or slightly less than the inner diameter of housing 522. Contacting member 530 is disposed within the housing, distal to a distal-most anchor 526, and is retracted relative to housing 522 by pulling pull cord 532. When retracted, anchor contacting member 530 contacts and applies force to a distal-most anchor 526 to release cause that anchor 526 to exit housing 522 via one of the apertures 528. Contacting member 530 is then pulled farther proximally to contact and apply force to the next anchor 526 to deploy that anchor 526, and so on.

Retracting contacting member 530 to push anchors 526 out of apertures 528 may help cause anchors 526 to avidly secure themselves to adjacent tissue. Using anchors 526 that are relatively straight/flat when undeployed allows anchors 526 with relatively large deployed sizes to be disposed in (and delivered from) a relatively small housing 522. In one embodiment, for example, anchors 526 that deploy into a shape approximating two intersecting semi-circles, circles, ovals, helices, or the like, and that have a radius of one of the semi-circles of about 3 mm may be disposed within a housing 522 having a diameter of about 5 French (1.67 mm) and more preferably 4 French (1.35 mm) or even smaller. Such anchors 526 may measure about 6 mm or more in their widest dimension. In some embodiments, housing 522 may have a diametrical dimension ("d") and anchor 526 may have a diametrical dimension ("D") in the deployed state, and the ratio of D to d may be at least about 3.5. In other embodiments, the ratio of D to d may be at least about 4.4, and more preferably at least about 7, and even more preferably at least about 8.8. These are only examples, however, and other larger or smaller anchors 526 may be disposed within a larger or smaller housing 522. Furthermore, any convenient number of anchors 526 may be disposed within housing 522. In one embodiment, for example, housing 522 may hold about 1-20 anchors 526, and more preferably about 3-10 anchors 526. Other embodiments may hold more anchors 526.

Anchor contacting member 530 and pull cord 532 may have any suitable configuration and may be manufactured from any material or combination of materials. In alternative embodiments, contacting member 530 may be pushed by a pusher member to contact and deploy anchors 526. Alternatively, any of the anchor deployment devices and methods previously described may be used.

Tether 534, as shown in FIG. 9B, may comprise any of the tethers 534 or tether-like devices already described above, or any other suitable device. Tether 534 is generally attached to a distal-most anchor 526 at an attachment point 536. The attachment itself may be achieved via a knot, weld, adhesive, or by any other suitable attachment means. Tether 234 then extends through an eyelet, loop or other similar configuration on each on each of the anchors 526 so as to be slidably coupled with the anchors 526. In the embodiment shown, tether 534 exits each aperture 528, then enters the next-most-proximal aperture, passes slidably through a loop on an anchor 526, and exits the same aperture 528. By entering and exiting each aperture 528, tether 534 allows the plurality of anchors 526 to be deployed into tissue and cinched. Other configurations of housing 522, anchors 526 and tether 534 may alternatively be used. For example, housing 522 may include a longitudinal slit through which tether 534 may pass, thus allowing tether 534 to reside wholly within housing before deployment.

Expandable member 524 is an optional feature of anchor delivery device 520, and thus may be included in some embodiments and not in others. In other words, a distal portion of anchor delivery device 520 may include housing, contents of housing, and other features either with or without an attached expandable member. Expandable member 524 may comprise any suitable expandable member currently known or discovered in the future, and any method and substance(s) may be used to expand expandable member 524. Typically, expandable member 524 will be coupled with a surface of housing 522, will have a larger radius than housing 522, and will be configured such that when it is expanded as housing 522 nears or contacts the valve annulus, expandable member 524 will push or press housing 522 into enhanced contact with the annulus. For example, expandable member 524 may be configured to expand within a space near the corner formed by a left ventricular wall and a mitral valve leaflet.

Figure 10C:
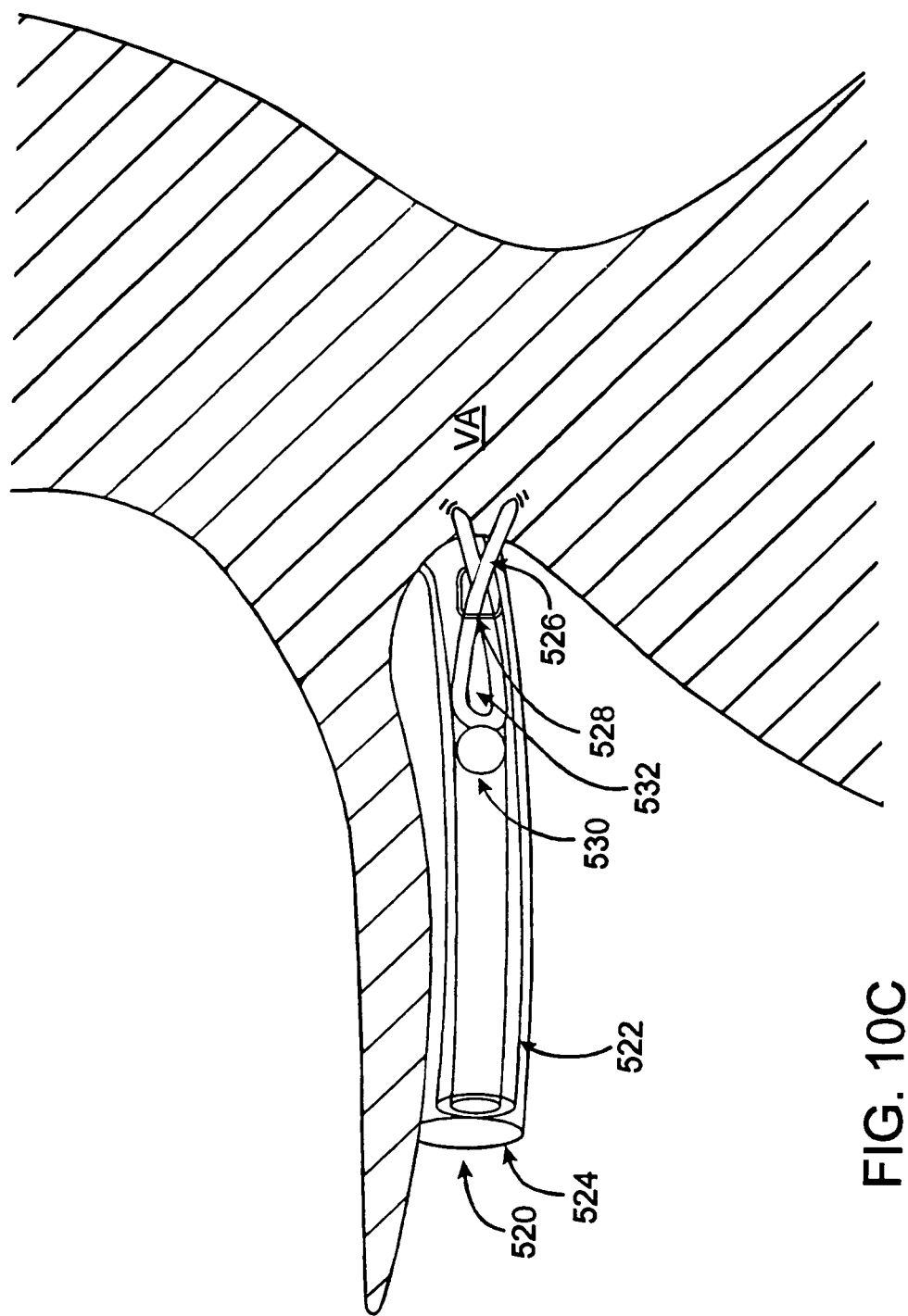

With reference now to FIGS. 10A-10F, a method is shown for applying a plurality of tethered anchors 526 to a valve annulus VA in a heart. As shown in FIG. 10A, an anchor delivery device 520 is first contacted with the valve annulus VA such that openings 528 are oriented to deploy anchors 526 into the annulus. Such orientation may be achieved by any suitable technique. In one embodiment, for example, a housing 522 having an elliptical cross-sectional shape may be used to orient openings 528. As just described, contact between housing 522 and the valve annulus VA may be enhanced by expanding expandable member 524 to wedge housing within a corner adjacent the annulus.

Generally, delivery device 520 may be advanced into any suitable location for treating any valve by any suitable advancing or device placement method. Many catheter-based, minimally invasive devices and methods for performing intravascular procedures, for example, are well known, and any such devices and methods, as well as any other devices or method later developed, may be used to advance or position delivery device 520 in a desired location. For example, in one embodiment a steerable guide catheter is first advanced in retrograde fashion through an aorta, typically via access from a femoral artery. The steerable catheter is passed into the left ventricle of the heart and thus into the space formed by the mitral valve leaflets, the left ventricular wall and cordae tendineae of the left ventricle. Once in this space, the steerable catheter is easily advanced along a portion (or all) of the circumference of the mitral valve. A sheath is advanced over the steerable catheter within the space below the valve leaflets, and the steerable catheter is removed through the sheath. Anchor delivery device 520 may then be advanced through the sheath to a desired position within the space, and the sheath may be removed. In some cases, an expandable member coupled to delivery device 520 may be expanded to wedge or otherwise move delivery device 520 into the corner formed by the left ventricular wall and the valve leaflets to enhance its contact with the valve annulus. Of course, this is but one exemplary method for advancing delivery device 520 to a position for treating a valve, and any other suitable method, combination of devices, etc. may be used.

As shown in FIG. 10B, when delivery device 520 is positioned in a desired location for deploying anchors 526, anchor contacting member 530 is retracted to contact and apply force to a most-distal anchor 526 to begin deploying anchor 526 through aperture 528 and into tissue of the valve annulus VA. FIG. 10C show anchor 526 further deployed out of aperture 528 and into valve annulus VA. FIG. 10D shows the valve annulus VA transparently so that further deployment of anchors 526 can be seen. As shown, in one embodiment of the invention, anchors 526 include two sharpened tips that move in opposite directions upon release from housing 522 and upon contacting the valve annulus VA. Between the two sharpened tips, an anchor 526 may be looped or have any other suitable eyelet or other device for allowing slidable coupling with a tether 534.

Referring now to FIG. 10E, anchors 526 are seen in their fully deployed or nearly fully deployed shape, with each pointed tip (or "arm") of each anchor 526 having curved to form a circle or semi-circle. Of course, in various embodiments anchors 526 may have any other suitable deployed and undeployed shapes, as described more fully above. FIG. 10F shows anchors 526 deployed into the valve annulus VA and coupled with tether 534, with the distal-most anchor 526 coupled attached fixedly to tether 524 at attachment point 536. At this stage, tether 534 may be cinched to tighten the annulus, thus reducing valve regurgitation. In some embodiments, valve function may be monitored by means such as echocardiogram and/or fluoroscopy, and tether 534 may be cinched, loosened, and adjusted to achieve a desired amount of tightening as evident via the employed visualization technique(s). When a desired amount of tightening is achieved, tether 534 is then attached to a most-proximal anchor 526 (or two or more most-proximal anchors 526), using any suitable technique, and tether 534 is then cut proximal to the most-proximal anchor 526, thus leaving the cinched, tethered anchors 526 in place along the valve annulus VA. Attachment of tether 534 to the most-proximal anchor(s) 526 may be achieved via adhesive, knotting, crimping, tying or any other technique, and cutting tether 534 may also be performed via any technique, such as with a cutting member coupled with housing 522.

In one embodiment, cinching tether 534, attaching tether 534 to most-proximal anchor 526, and cutting tether 534 are achieved using a termination device (not shown). The termination device may comprise, for example, a catheter advancable over tether 534 that includes a cutting member and a nitinol knot or other attachment member for attaching tether 534 to most-proximal anchor. The termination catheter may be advanced over tether 534 to a location at or near the proximal end of the tethered anchors 526. It may then be used to apply opposing force to the most-proximal anchor 526 while tether 534 is cinched. Attachment and cutting members may then be used to attach tether 534 to most-proximal anchor 526 and cut tether 534 just proximal to most-proximal anchor 526. Such a termination device is only one possible way of accomplishing the cinching, attachment and cutting steps, and any other suitable device(s) or technique(s) may be used.

In some embodiments, it may be advantageous to deploy a first number of anchors 526 along a first portion of a valve annulus VA, cinch the first anchors to tighten that portion of the annulus, move the delivery device 520 to another portion of the annulus, and deploy and cinch a second number of anchors 526 along a second portion of the annulus. Such a method may be more convenient, in some cases, than extending delivery device 520 around all or most of the circumference of the annulus, and may allow a shorter, more maneuverable housing 522 to be used.

In an embodiment similar to that shown in FIGS. 10A-10F, an analogous method may be used but anchors 526 may be driven out of delivery device 520 through a biocompatible material attached to delivery device 520, thereby attaching the biocompatible material to the valve annulus VA. For example, in one embodiment a Dacron strip may be attached to delivery device 520, extending along device 520 and covering apertures 528. Anchors 526 are then driven out of delivery device 520, through the Dacron strip, into the valve annulus VA, thus detaching the Dacron strip from device 520 and attaching it to the valve annulus VA. Such a biocompatible material may facilitate tissue ingrowth of anchors 526 and may enhance attachment generally to the valve annulus VA. In an alternative embodiment, multiple pieces of biocompatible material, such as separate pieces of material disposed over each of apertures 528, may be used. For example, in one embodiment multiple discs of Dacron material are disposed over multiple apertures 528.

In another embodiment, a distal portion of delivery device 520 may be detachable from a proximal portion of delivery device 520. Such an embodiment may be configured such that when anchors 526 are deployed from device 520, the distal portion of device 520 detaches from the proximal portion and is attached, via anchors 526, to the valve annulus VA. In one embodiment, for example, anchors 526 may pierce through the distal portion of device 520, rather than exiting device 520 through apertures 528. The distal portion may be detachable via any suitable means, such as perforations or the like.

Figure 11:
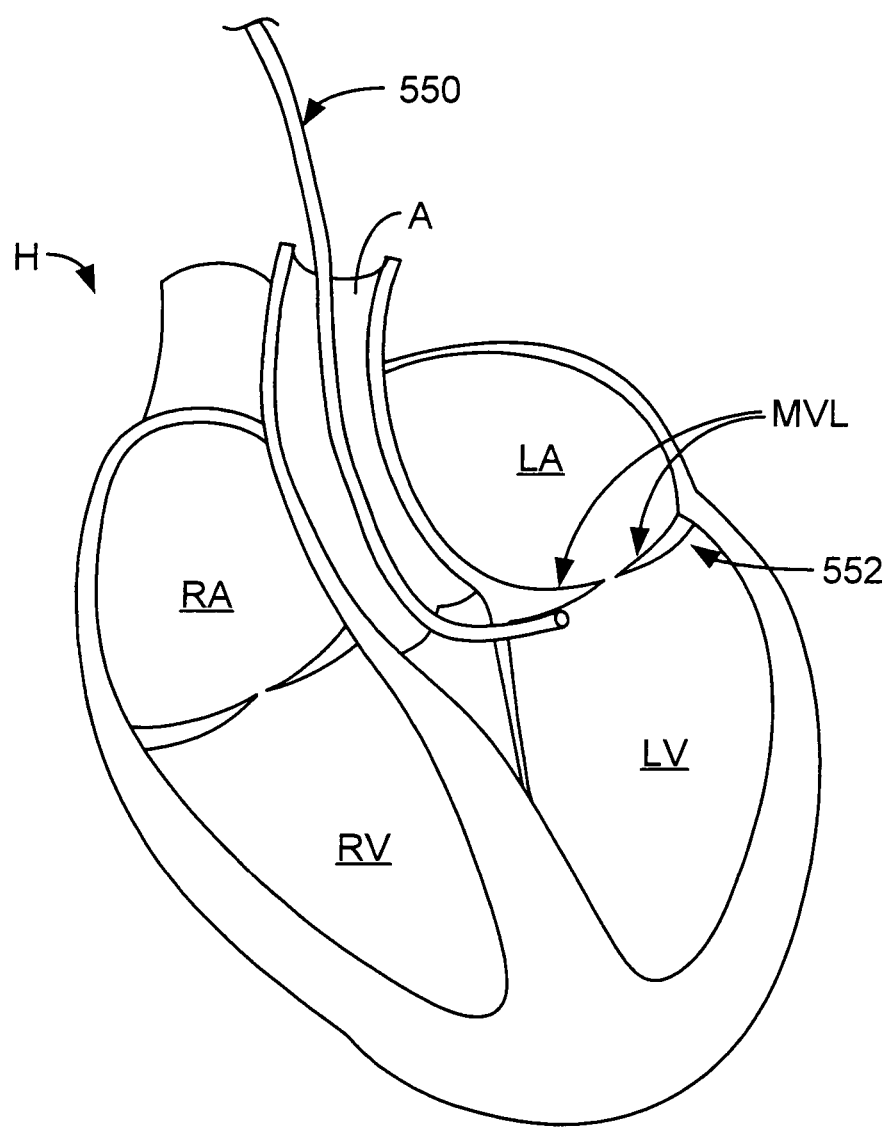
FIG. 11 shows a heart in cross-section with a guide catheter device advanced through the aorta into the left ventricle according to an embodiment of the invention.

Referring now to FIG. 11, a cross-sectional depiction of a heart H is shown with an anchor delivery device guide catheter 550 advanced through the aorta A and into the left ventricle LV. In a preferred embodiment, this access route to the subannular space and the valve annulus may used. Guide catheter 550 is generally a flexible elongate catheter which may have one or more curves or bends toward its distal end to facilitate placement of the distal end of catheter 550 in a subannular space 552. Subannular space 552, which has been described above in detail, is generally defined by the left ventricular wall, the mitral valve leaflets MVL, and cordae tendiniae, and travels along most or all of the circumference of the valve annulus. The distal end of guide catheter 550 may be configured to be positioned at an opening into space 552 or within space 552, such that subsequent catheter devices may be passed through guide catheter 550 into space 552. In some embodiments, it may be advantageous to provide guide catheter 550 with a curvable portion with a radius in an expanded/curved state that is greater than a radius of the valve annulus. For example, in one embodiment guide catheter 550 in the expanded state has a radius about 25%-50% larger that the valve annulus.

Figure 11A:
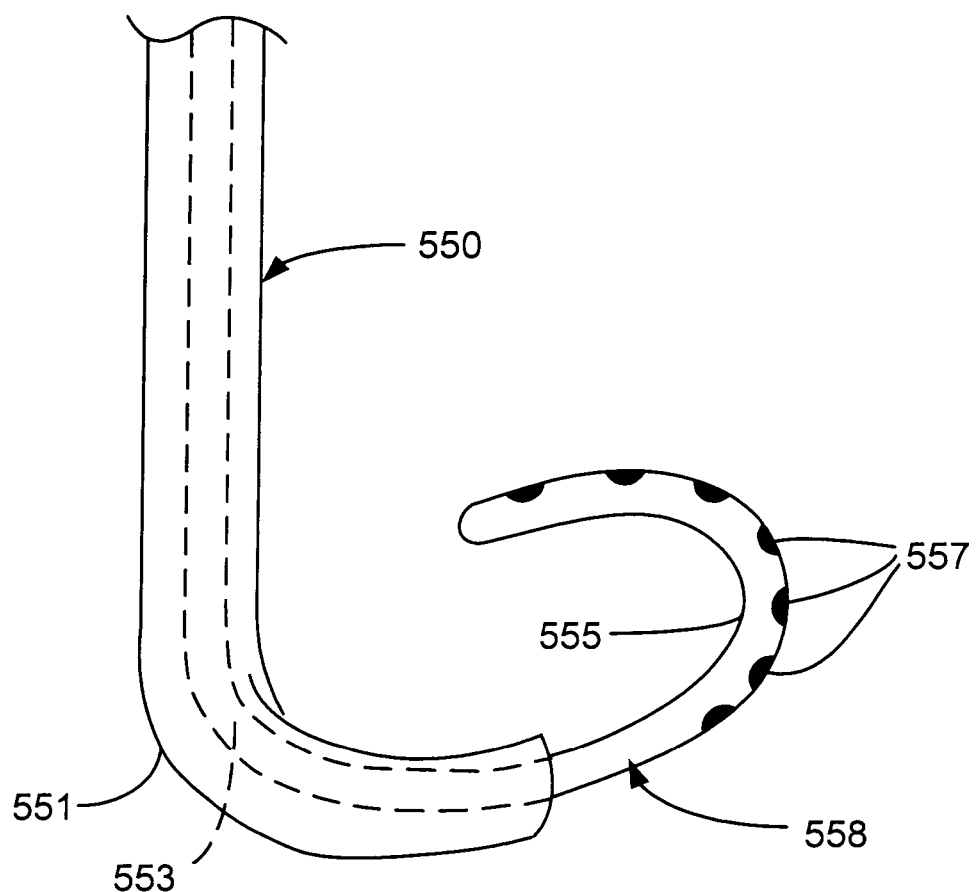
FIG. 11A shows a distal end of an anchor delivery device passing through a guide catheter according to an embodiment of the invention.
Figure 11B:
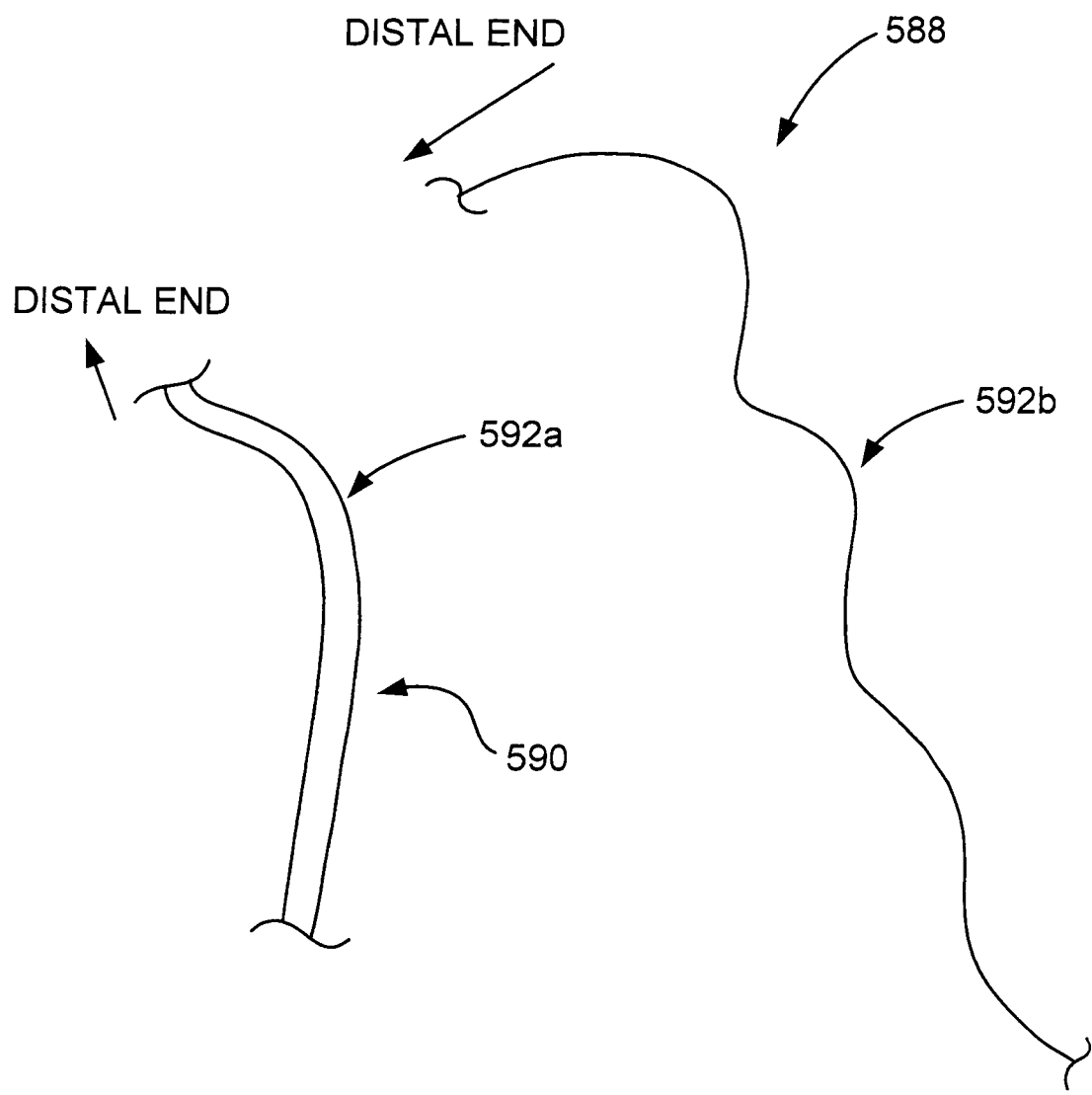
FIG. 11B shows middle portions of an anchor delivery device and a guide catheter having corresponding orientation portions according to an embodiment of the invention.

With reference now to FIG. 11B, in the embodiment described immediately above and/or in alternative embodiments, an anchor delivery device 588 and a guide catheter 590 may include one or more corresponding (or "registering") bends or orientation portions 592a, 592b at other locations along their lengths. In other words, although bends 551, 553, 555 are shown in FIG. 11A at or near the distal ends of guide catheter 550 and anchor delivery device 558, similar bends could be formed at more proximal locations. For example, FIG. 11B shows guide catheter 590 with orientation portion 592a having a chosen shape when relaxed. The chosen shape may lie along a two-dimensional or three-dimensional path. Anchor delivery device 588 has a corresponding orientation portion 592b along its length which is complementary to the shape of orientation portion 592a. The chosen shape may also be created by the application of energy, mechanical manipulation or the like. Such orientation portions 592a, 592b could be used for further registering or orienting delivery device 588 to a desired orientation. Typically, when orientation portions 592a, 592b are axially aligned, which can be indicated by orientation markers at the proximal ends of guide catheter 590 and anchor delivery device 588 external of the patient, proper rotary orientation can be sensed tactically by the physician to help insure the distal end of anchor delivery device 588 is properly oriented. Delivery device 588 may be rotated, advanced or moved in any suitable fashion within guide catheter 590 to achieve a desired orientation. The use of one or more complementary orientation portions 592a, 592b may be used with any of a number of various embodiments of guide catheters and anchor delivery devices.

Figure 12A:
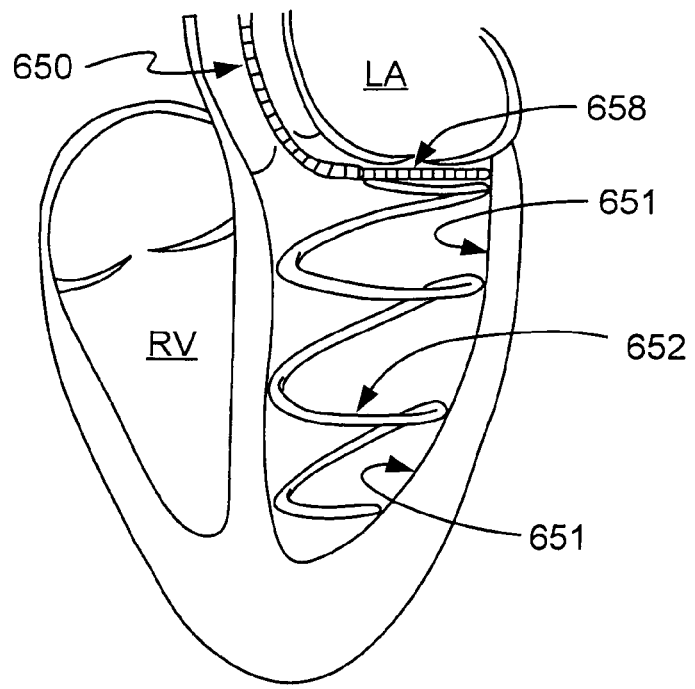
FIGS. 12A-12D show various embodiments of support members for supporting an anchor delivery device against a valve annulus.

In a number of cases, and with reference now to FIGS. 12A-12D, it may be advantageous to provide further support to an anchor delivery device 658, to support the device 658 against valve annulus tissue and/or to push the device 658 against valve annulus tissue to enhance contact with, and anchor delivery into, the tissue. In one embodiment, as shown in FIG. 12A, a helical support member 652 may be coupled with a distal end of anchor delivery device 658 and may be extended into the left ventricle of a heart (or other heart chamber in other embodiments) to contact the heart wall 651 and thus support anchor delivery device 658 against the valve annulus tissue. In alternative embodiments, helical support member 651 may extend out of a guide catheter 650 to contact the heart wall 651 and support anchor delivery device 658. Any suitable means may be used for extending helical member 652 into the left ventricle or other chamber. For example, helical member 652 is pushed out of guide catheter 650 in one embodiment, but may alternatively be extended out of anchor delivery device 658. Helical member 652 may be made of any suitable material, such as but not limited to Nitinol, stainless steel or the like.

Figure 12B:
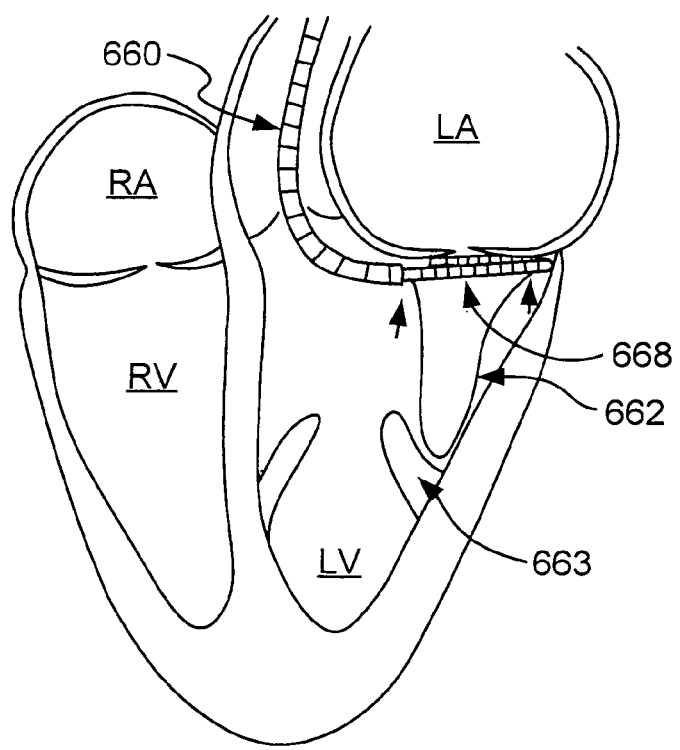

In an alternative embodiment, pictured in FIG. 12B, a deployable U-shaped support member 662 may be movably coupled with a distal portion of an anchor delivery device 668, both of which are advanceable through a guide catheter 660. Upon being advanced out of the distal end of guide catheter 660, U-shaped member 662 may automatically spring out, or alternatively may be manually manipulated to extend outward, to contact the inner surface of the heart wall and/or to contact a papillary muscle 663. As shown in FIG. 12B, in one embodiment U-shaped member 663 contacts an intersection of a papillary muscle 663 with the heart wall, and thus provides upward support (solid-tipped arrows) to anchor delivery device 668. Again, such a U-shaped member 662 may automatically deform from a straight configuration for delivery through guide catheter 660 into a U-shaped configuration, such as if member 662 is made of Nitinol, spring stainless steel, or other shape memory or super-elastic material. Alternatively, U-shaped member 662 may be connected to anchor delivery device 668 at or near the distal end of the device 668 and may be pushed distally to force the U-shaped member 662 to expand into its U-shape. In an alternative embodiment, U-shaped member 662 may be attached proximally and may be pulled into its expanded configuration. Any suitable method for changing the shape of U-shaped member 662 from straight to U-shaped may be used in various embodiments.

Figure 12C:
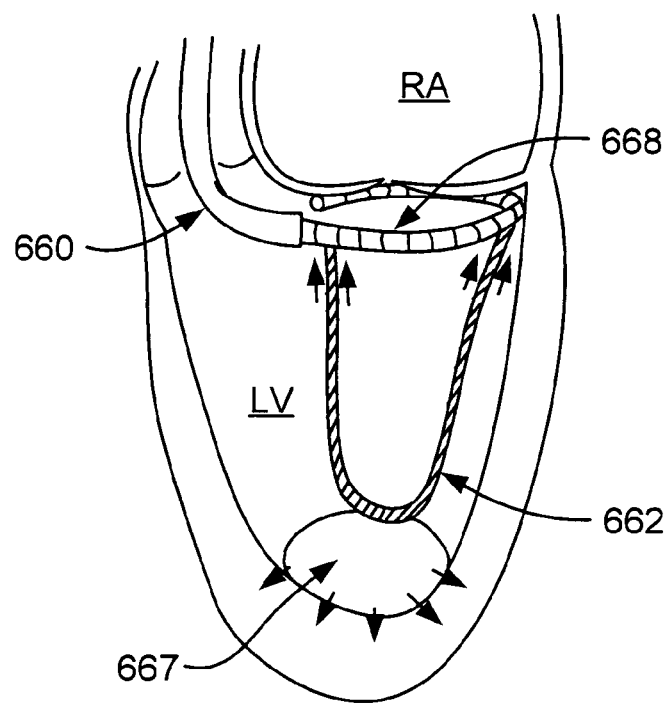
Figure 12D:
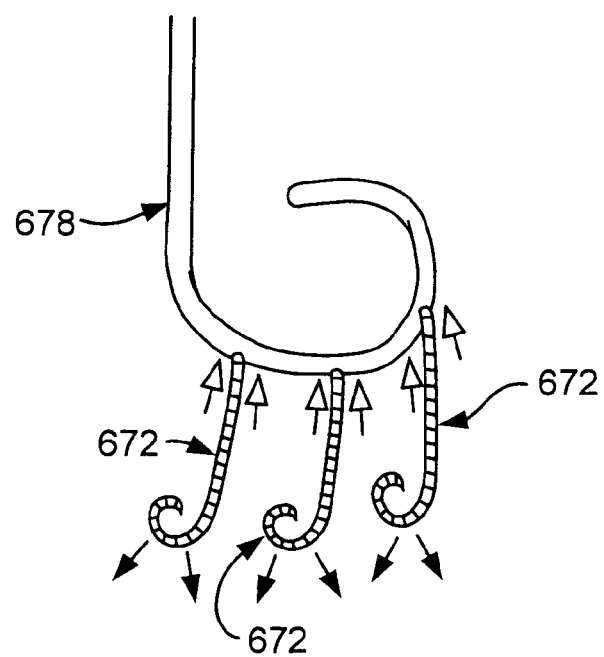

As shown in FIG. 12C, U-shaped member 662 may optionally include an expandable member 667, such as an inflatable balloon. Expandable member 667 may be expanded to provide further force against and support of anchor delivery device 668, to enhance its contact with valve annulus tissue. In another embodiment, as shown in FIG. 12D, multiple spring members 672 may be coupled with a distal end of an anchor delivery device 678 to provide force against an inner surface of a heart wall (solid tipped arrows) to thus support anchor delivery device 678 against annulus tissue (hollow tipped arrows). Thus, various embodiments of the invention may include any of a number of suitable support devices for enhancing support of an anchor delivery device against valve annulus tissue, thus enhancing the ability of the delivery device to delivery tissue anchors into the annulus.

Figure 13A:
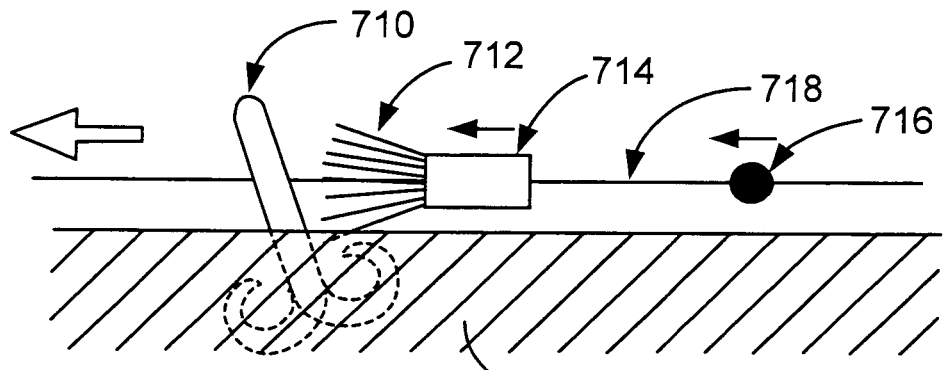
FIGS. 13A-13C show a device and method for facilitating termination and load distribution of a series of anchors according to one embodiment of the invention.
Figure 13B:
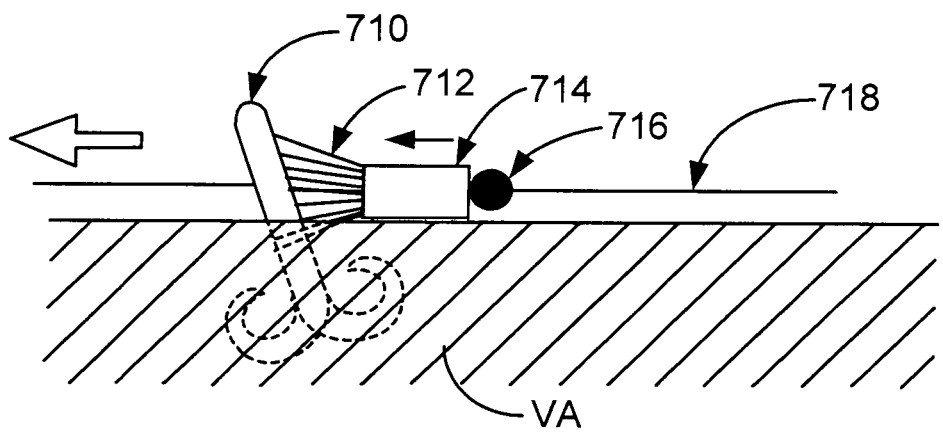
Figure 13C:
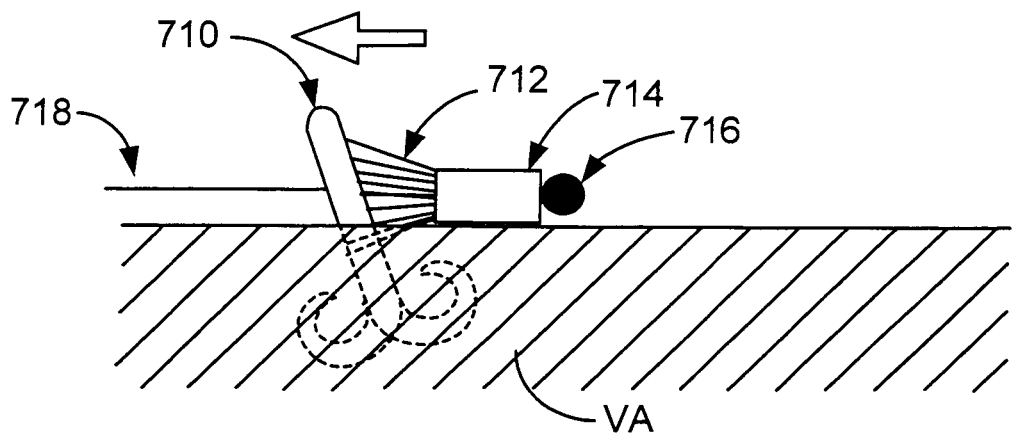

Referring now to FIGS. 13A-13C, in some embodiments it may be advantageous to provide one or more devices to enhance the attachment of a terminal tissue anchor 710 to valve annulus tissue VA. Typically, in attaching tissue anchors to valve annulus tissue VA, a first tethered anchor (not shown) is attached, and subsequent anchors are then attached, ending in a final or terminal anchor 710. A tether 718 is then cinched, to apply force between the attached anchors (hollow arrow), thus cinching the valve annulus VA. Tether 718 is then typically attached by any suitable means to terminal anchor 710 and then cut or otherwise detached proximal to the terminal anchor 710, leaving the cinched, tethered anchors in place, attached to the valve annulus VA. To relieve some of the tension placed on terminal anchor 710 and/or to provide additional attachment/anchoring strength to the terminal end of the tethered anchors, one or more locking members 714 may be deployed at or near the terminal end. For example, in one embodiment locking member 714 comprises a cylinder slidably disposed over tether 718, with prongs 712 extending from one end of the cylinder. Locking member 714 is deployed out of the distal end of a termination catheter, guide catheter or the like (not shown) and is then slid along tether 718, such that prongs 712 contact and enter into valve annulus tissue VA. In one embodiment, a pusher member 716, such as a ball slidably disposed over tether 718, may be used to push locking member 714 forward and into engagement with tissue, as shown in FIG. 13B and as designated by solid tipped arrows. In some embodiments, locking member 714 engages with terminal anchor 710, as shown in FIGS. 13B and 13C, though such engagement is not required. Once locking member 714 is fully engaged with valve tissue VA, tether 718 is cut proximal to locking member 714. In some embodiments, pusher member 716 remains in place, while in others it may be removed before cutting tether 718.

A number of different variations of locking members are contemplated in various embodiments. For example, a two-pronged member may be used, with the prongs deployable from a delivery position to and expanded configuration, and with the prongs optionally engaging with the terminal anchor 710. In another embodiment, multiple prongs may be aligned in a linear fashion along a locking member, such as in a rake-like configuration. Yet another embodiment include two prongs for engaging with the terminal anchor 710 and another prong for engaging with valve annulus tissue VA. Thus, any of a number of different embodiments may be employed as part of the present invention. Such locking members may be constructed from any suitable material or combination of materials, such as Nitinol, spring stainless steel and/or other shape memory or super-elastic materials.

Figure 14A:
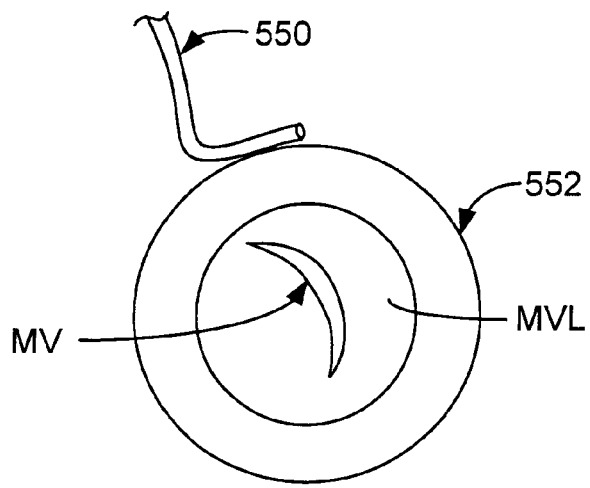
FIGS. 14A-14F demonstrate a method for advancing an anchor delivery device to a position for treating a heart valve according to an embodiment of the invention.
Figure 14B:
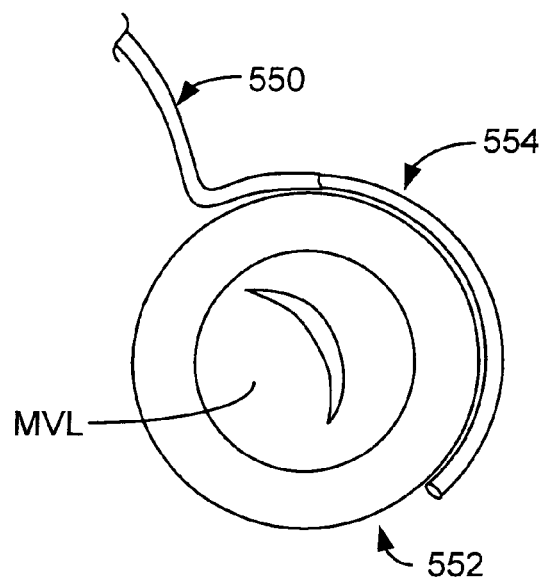

FIGS. 14A-14F demonstrate a method for advancing an anchor delivery device to a position for treating a mitral valve MV. The mitral valve MV, including mitral valve leaflets MVL are represented diagrammatically from an inferior perspective looking up, to depict a method for delivering a device into subannular space 552. In FIG. 14A, first guide catheter 550 is show extending up to or into subannular space 552, as in FIG. 11. As shown in FIG. 14B, in one method a second guide catheter 554 may be advanced through first guide catheter 550 to pass through/along subannular space 554. This second guide catheter 554 is steerable in one embodiment, as will be described further below, to help conform second guide catheter 554 to subannular space 552.

Figure 14C:
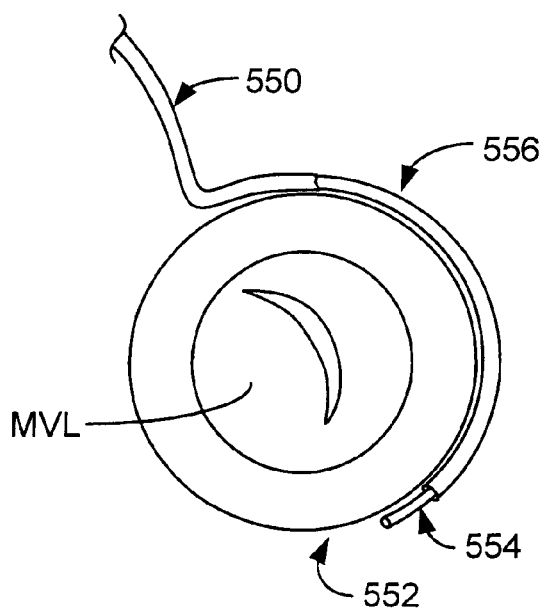
Figure 14D:
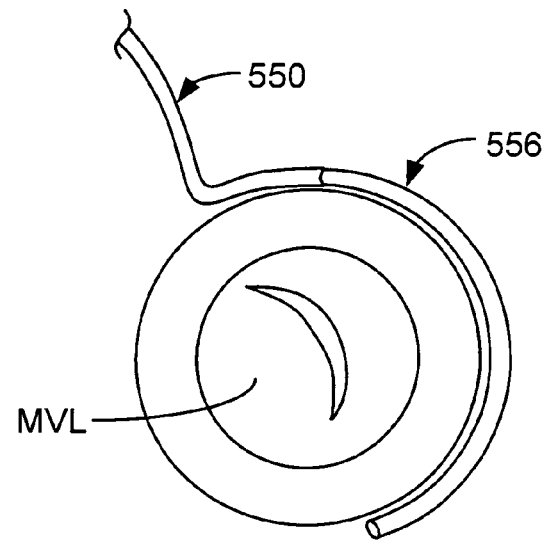
Figure 14E:
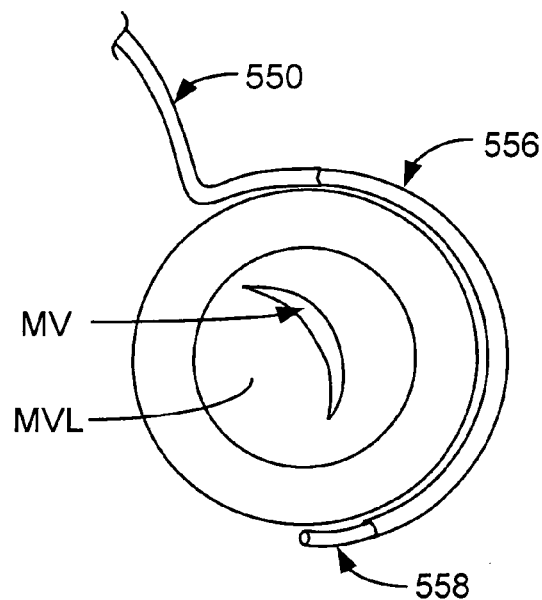
Figure 14F:
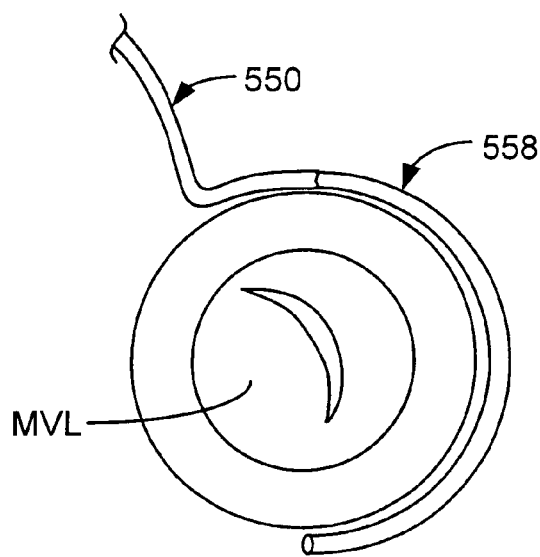

Next, as in FIG. 14C, a guide sheath 556 may be passed over second guide catheter 554 to extend along subannular space. Sheath 556 is generally a flexible, tubular member that can be passed over second guide catheter 554 and within first guide catheter 550. To enhance passage and exchange, any of these and other described catheter members, sheath members, or the like may be manufactured from and/or coated with one or more friction resistant materials. Once sheath 556 is in place, second guide catheter 554 may be withdrawn, as shown in FIG. 14D. As shown in FIG. 14E, an anchor delivery device 558 may then be advanced through sheath 556 to a position for treating the mitral valve MV. Sheath 556 may then be withdrawn, as in FIG. 14F, leaving anchor delivery device 558 in place for performing a treatment. A valve annulus treatment may be performed, as described extensively above, and anchor delivery device 558 may be withdrawn. In some embodiments, anchor delivery device 558 is used to treat one portion of the valve annulus and is then moved to another portion, typically the opposite side, to treat the other portion of the annulus. In such embodiments, any one or more of the steps just described may be repeated. In some embodiments, anchor delivery device 558 is withdrawn through first guide catheter 550, and first guide catheter 550 is then withdrawn. In alternative embodiments, first guide catheter 550 may be withdrawn before anchor delivery device 558.

In various embodiments, alternative means may be used to urge anchor delivery device 558 into contact with the valve annulus. For example, in one embodiment an expandable member is coupled with anchor delivery device 558 and expanded within the subannular space 552. In an alternative embodiment, a magnet may be coupled with anchor delivery device 558, and another anchor may be disposed within the coronary sinus, in proximity to the first magnet. The two magnets may attract one another, thus pulling the anchor delivery device 558 into greater contact with the annulus. In another embodiment, anchor delivery device 558 in an expanded (or deployed) state may have a radius of curvature that is larger than the radius of curvature of the mitral valve annulus, thus causing device 558 to be urged against the annulus. In one embodiment, for example, the radius of curvature of device 558 in the expanded/deployed state is about 25%-50% larger than the radius of curvature of the mitral valve annulus.

Various embodiments may also include visualizing the annulus using a visualization member coupled with the anchor delivery device 558 or separate from the device 558. In some embodiments, anchors may be driven through a strip of detachable, biocompatible material, such as Dacron, that is coupled with anchor delivery device 558 but that detaches to affix to the valve annulus via the anchors. In some embodiments, the strip may then be cinched to tighten the annulus. In other embodiments, the anchors may be driven through a detachable, biocompatible, distal portion of the guide sheath 556, and guide sheath 556 may then remain attached to the annulus via the anchors. Again, in some embodiments, the detached sheath may be cinched to tighten the annulus.

Of course, the method just described is but one embodiment of a method for delivering an anchor delivery device to a location for treating a valve annulus. In various alternative embodiments, one or more steps may be added, deleted or modified while achieving a similar result. In some embodiments, a similar method may be used to treat the mitral valve from a superior/right atrial position or to treat another heart valve. Additionally, other devices or modifications of the system just described may be used in other embodiments.

Figure 15A:
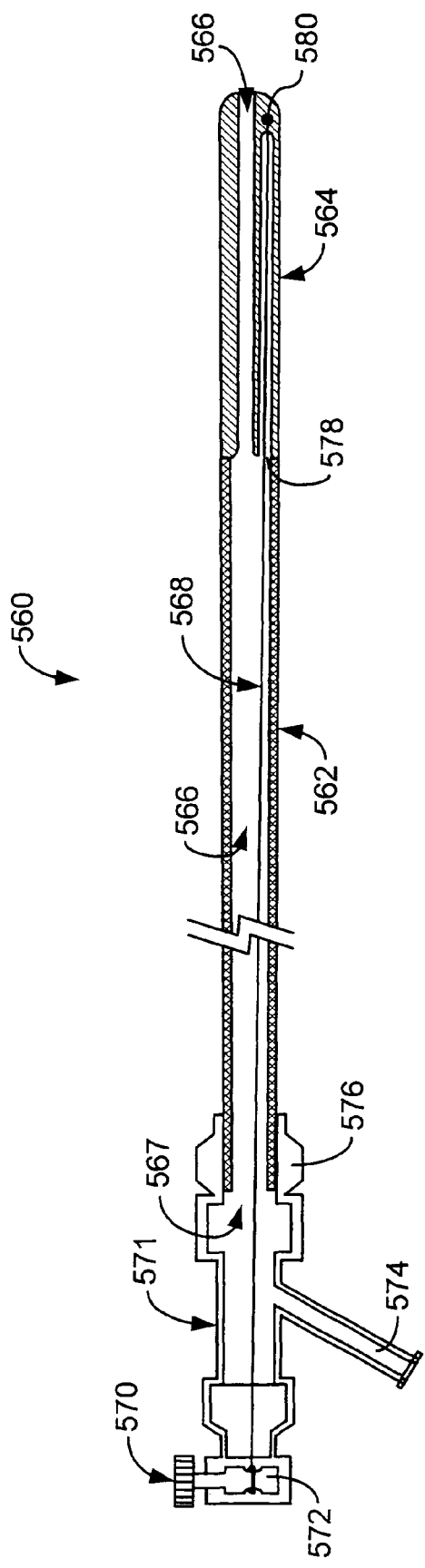
FIGS. 15A and 15B are side cross-sectional views of a guide catheter device for facilitating positioning of an anchor delivery device according to an embodiment of the invention.
Figure 15B:
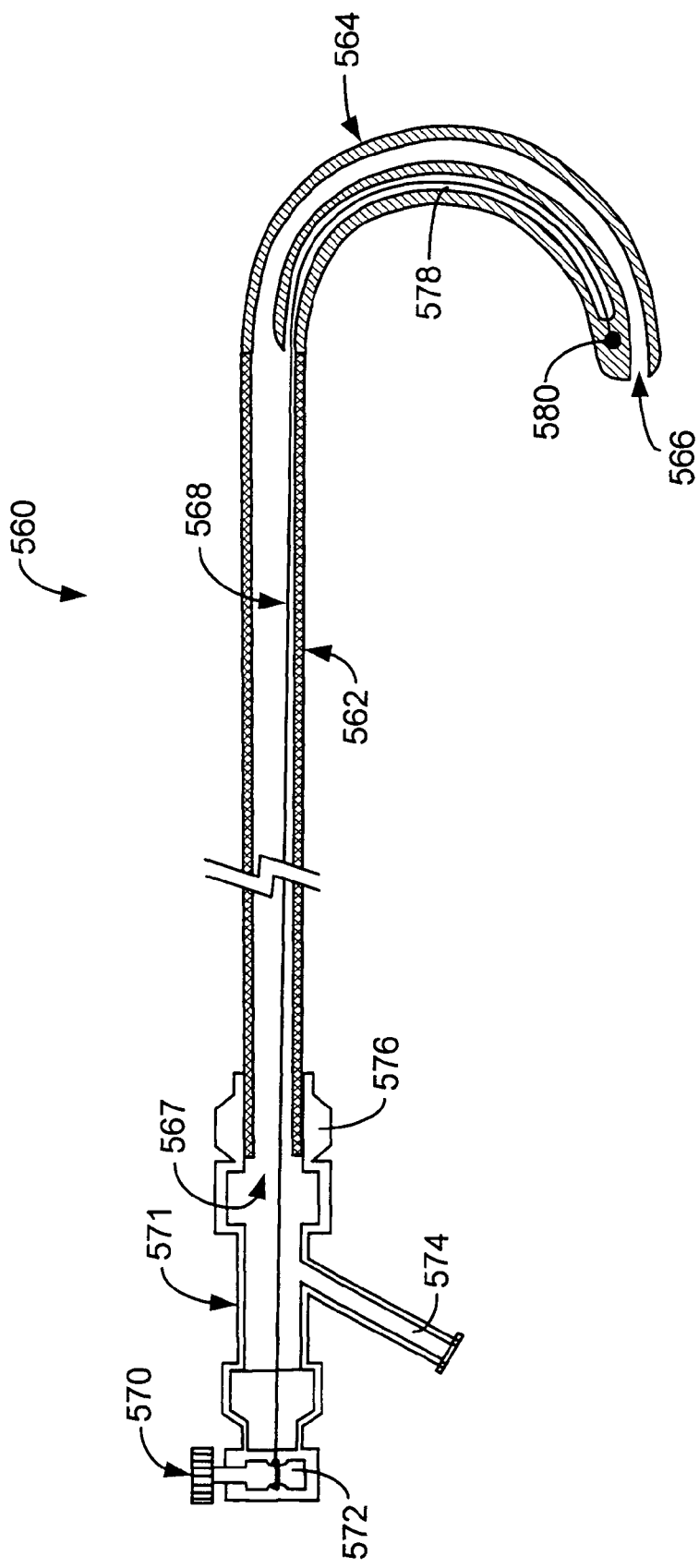

With reference now to FIGS. 15A and 15B, one embodiment of a steerable catheter device 560 is shown. Steerable catheter device 560 may be used in a method such as that just described in reference to FIGS. 14A-14F, for example in performing a function similar to that performed by second guide catheter 554. In other embodiments, catheter device 560 may perform any other suitable function. As shown, catheter device 560 suitably includes an elongate catheter body having a proximal portion 562 and a distal portion 564. At least one tensioning member 568, such as but not limited to a tensioning cord, extends from proximal portion 562 to distal portion 564 and is coupled with the distal portion 564 and at least one tensioning actuator 570/572 on the proximal portion. Tensioning actuator 570/572 may include, for example, a knob 570 and a barrel 572 for wrapping and unwrapping tensioning member 568 to apply and remove tension. Tensioning member 568 is coupled with distal portion 564 at one or more connection points 580. In some embodiments, catheter device 560 includes a proximal housing 571, handle or the like, coupled to the proximal end of proximal portion 562 via a hub 576 or other means. Housing 571 may be coupled with tensioning actuator 570/572 and may include one or more arms 574 for infusing fluid or for other functions. In the embodiment shown, arm 574 and housing 571 include a lumen 567 that is in fluid communication with a fluid lumen 566 of the catheter body. Fluid may be introduced through arm 574 to pass through fluid lumen 566 to provide, for example, for contrast material at the distal tip of catheter device 560 to enhance visualization of device 560 during a procedure. Any other suitable fluid(s) may be passed through lumens 567/566 for any other purpose. Another lumen 578 may be included in distal portion 564, through which tensioning member 568 passes before attaching at a distal location along distal portion 564.

FIG. 15B shows catheter device 560 in a deformed/bent configuration, after tension has been applied to distal portion 564 by applying tension to tensioning member 568, via knob 570 and barrel 572. The bend in distal portion 564 will allow it to conform more readily to a valve annulus, while catheter device 560 in its straight configuration will be more amenable to passage through vasculature of the patient. Tensioning member 568 may be manufactured from any suitable material or combination of materials, such as but not limited to Nitinol, polyester, nylon, polypropylene and/or other polymers. Some embodiments may include two or more tensioning members 568 and/or two or more tensioning actuators 570/572 to provide for changes in shape of distal portion 564 in multiple directions. In alternative embodiments, knob 570 and barrel 572 may be substituted with any suitable devices, such as a pull cord, button, lever or other actuator. Various alternatives may also be substituted for tensioning member 568 in various embodiments. For example, shaped expandable members, shape memory members and/or the like may be used to change the shape of distal portion 564.

Generally, proximal portion 562 of the catheter body is less flexible than distal portion 564. Proximal portion 562 may be made of any suitable material, such as PEBAX, FEP, nylon, polyethylene and/or the like, and may include a braided material, such as stainless steel, to provide stiffness and strength. Distal portion 564 may be made of similar or other materials, but the braided material is typically not included, to provide for greater flexibility. Both proximal and distal portions 562/564 may have any suitable lengths, diameters, overall configurations and the like. In one embodiment the catheter body is approximately 140 cm in length and 6 French in diameter, but any other suitable sizes may be used in other embodiments. Either proximal portion 562, distal portion 564 or preferably both, may be made from or coated with one or more friction resistant or lubricating material to enhance passage of device 560 through an introducer catheter and/or to enhance passage of a sheath or other device over catheter device 560.

Figure 16A:
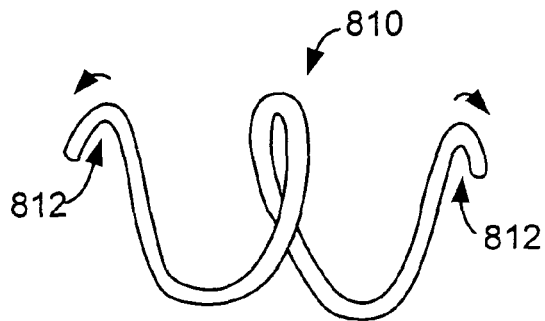
FIGS. 16A-16E show improved tissue anchors according to various embodiments of the present invention.
Figure 16B:
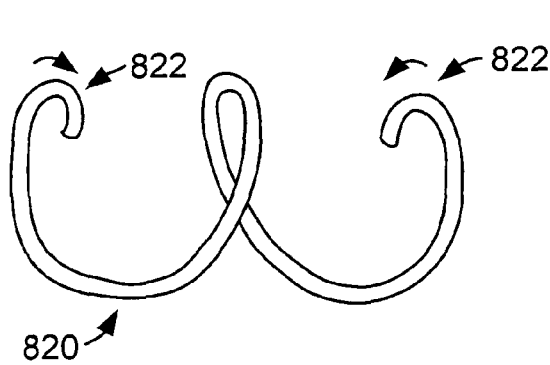
Figure 16D:
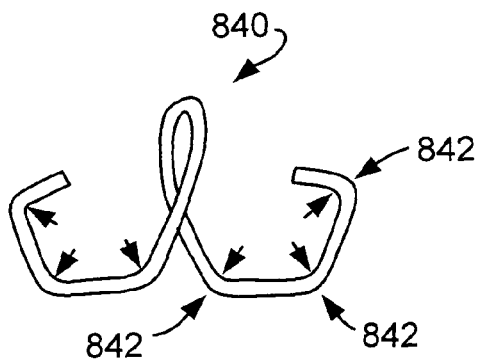
Figure 16C:
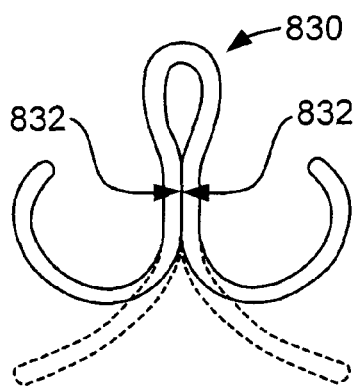
Figure 16E:
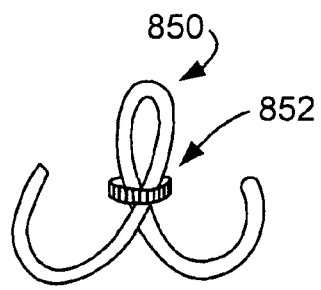

With reference now to FIGS. 16A-16E, another aspect of the present invention includes improved tissue anchors for enhancing anchor attachment to valve annulus tissue. Such improved anchors typically include one or more features to help prevent the anchors from pulling out of tissue, when the anchors are placed under tension from a cinched tether, and/or to help promote tissue ingrowth of the anchors to further enhance attachment. In one embodiment, as shown in FIG. 16A, a tissue anchor 810 includes outwardly facing hooks 812 or bends at the ends of the two arms of anchor 810. In another embodiment, as in FIG. 16B, a tissue anchor 820 includes inwardly facing hooks 822. In a related embodiment, shown in FIG. 16D, a tissue anchor 840 includes multiple bends 842. In any of these embodiments, hooks 812, 822 or bends 842 have been found to enhance attachment of anchors 810, 820, 840 to tissue and thus prevent anchor pullout. In another embodiment, shown in FIG. 16C, two arms of a tissue anchor 830 are attached at an attachment point 832. The attachment point 832 may be formed by any suitable technique, such as soldering or the like. In another embodiment, as in FIG. 16E, a belt 852 may be disposed over a tissue anchor 850 to hold the two arms of the anchor together. In either of the embodiments shown in FIGS. 16C and 16E, holding the two arms of the anchor together has been found to reduce pullout of the anchors 830, 850 from tissue.

In the embodiments just described or in alternative embodiments, tissue anchors may also have one or more features designed to enhance ingrowth and/or encapsulation of the anchors into annular tissue. Such features, for example, may include a coating, a porous and/or rough surface, an attachment such as a polyester band or belt, or any other suitable surface feature or added feature. By promoting encapsulation of tissue anchors, attachment strength of the anchors to tissue is enhanced.

Figure 17A:
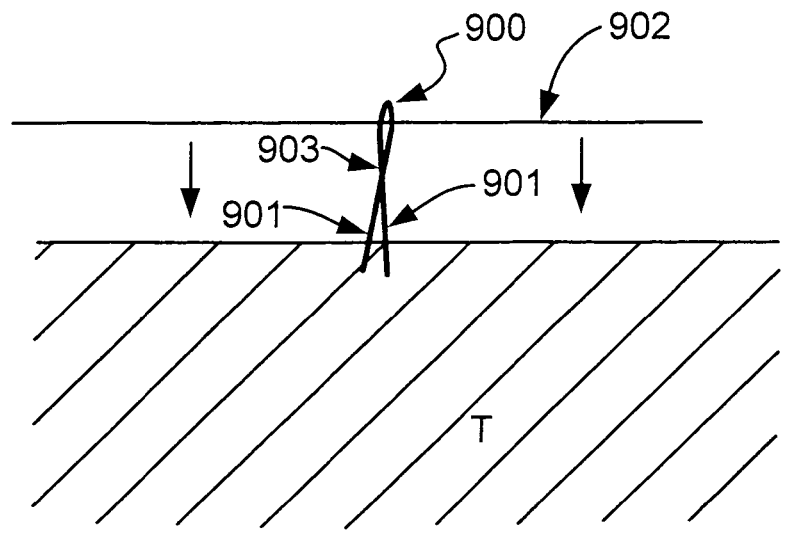
FIGS. 17A-17C show a self-forming anchor attaching to tissue of a valve annulus according to one embodiment of the present invention.
Figure 17B:
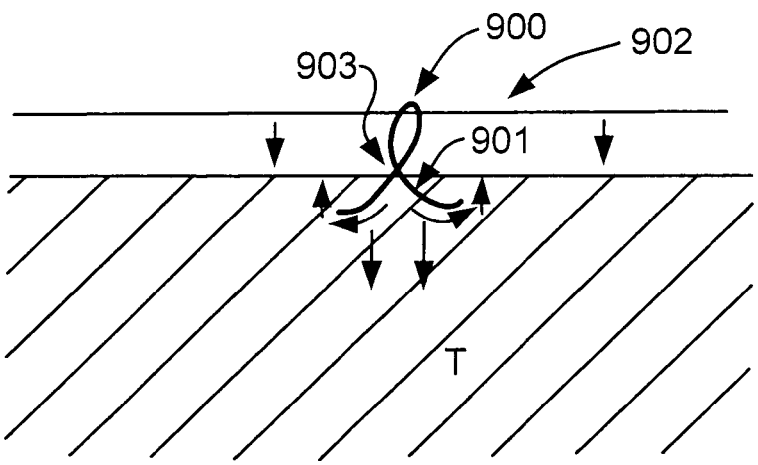
Figure 17C:
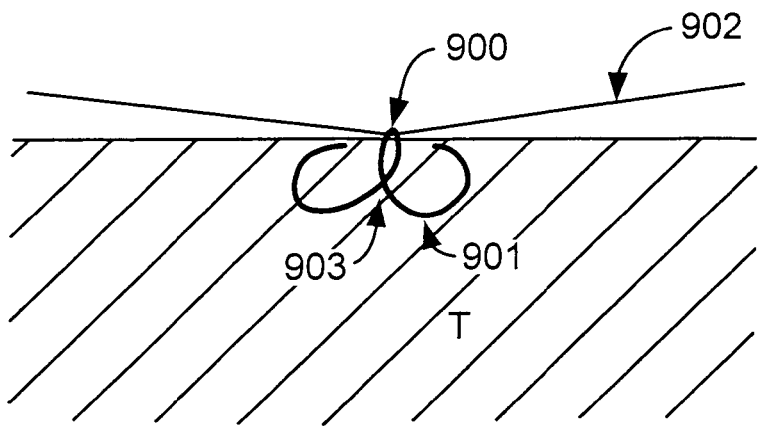

Referring now to FIGS. 17A-17C, in many embodiments, self-forming anchors 900 are stored in the delivery device in a straightened configuration, coupled with a tether 902, as shown in FIG. 17A. Basically, anchors 900 are held or restrained in that straightened state, while their natural configuration is curved. Thus, when the straightened anchor 900 is released from the delivery device into tissue T, the anchor 900 actually pulls itself into the tissue T, as shown in FIG. 17B, due to the storage of potential energy in the straightened state and the tendency of each of the arms 901 of anchors 900 to drive the tip of the arm into the tissue as illustrated. Arms 901 are joined together at a junction 903. Each arm 901 is braced against the other arm so that forces exerted by tissue T on each arm 901 are opposed by the other arm 901 wherein the arms are joined to one another. This eliminates the need for an anchor driving device, such as required with staples, thus substantially simplifying the assembly and method. In addition, bracing arms 901 against one another also helps to reduce or eliminate problems associated with tissue deflection. As shown by the hollow-tipped arrows in FIG. 17B, the anchor 900 pulls itself into tissue T as it assumes its natural, curved shape, and exerts forces in vertical, horizontal and curved directions. Finally, after pulling itself into tissue and assuming its natural shape, as in FIG. 17C, anchor 900 is fully embedded in the tissue T.

Figure 18:
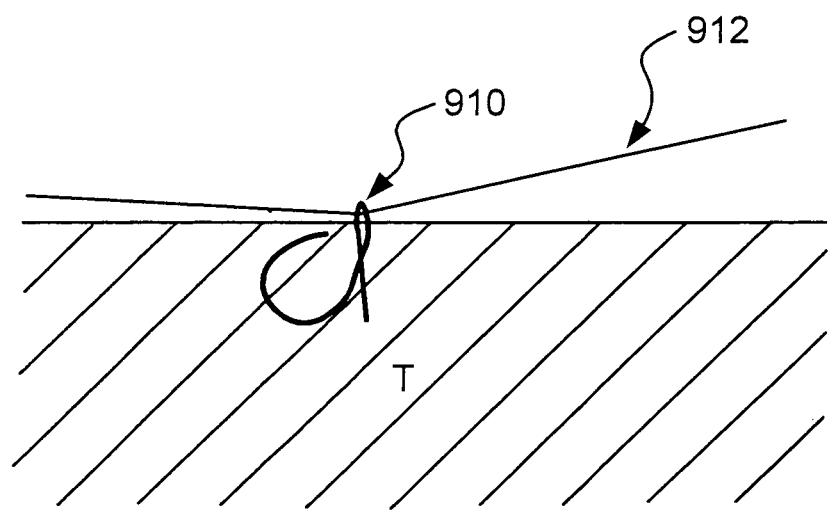
FIG. 18 shows a self-forming anchor attaching to tissue of a valve annulus according to another embodiment of the present invention.

In an alternative embodiment, as shown in FIG. 18, anchors 910 may have one curved arm and one straight arm. Such an anchor 910 will still pull itself into tissue T, thus embedding itself and positioning the tether 912 flush with the tissue T.

Figure 19A:
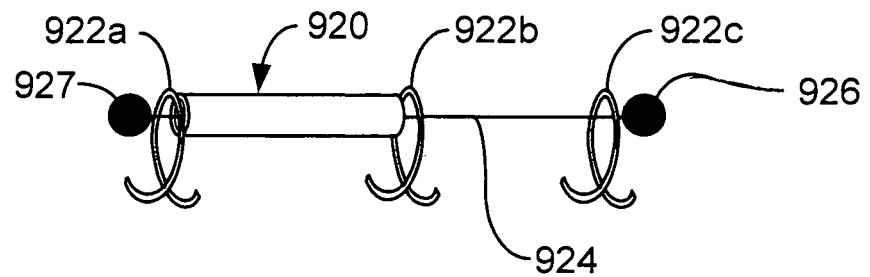
FIG. 19A shows an anchor device having a sleeve between two adjacent anchors according to one embodiment of the invention.

Referring now to FIG. 19A, some embodiments of a valve annulus anchor device may include anchors 922, a tether 924, a distal force applying member 927 coupled with the tether 924, a termination member 926 and one or more force distributing sleeves 920 disposed over the tether 924 and between adjacent anchors 922. In one embodiment, as shown, a separate sleeve 920 may be disposed between two adjacent anchors 922a, 922b. Additional sleeves 920 may optionally be disposed between other sets of two anchors, such as anchors 922b and 922c. In FIG. 19A, only three anchors 922 are shown for simplicity, but any number of anchors 922 and sleeves 920 between anchors may be used in various embodiments. Sleeve 920 acts to distribute force applied between two adjacent anchors 922, to help prevent such anchors 922 from pulling out of tissue when force is applied to tether 924. Sleeve 922 may be made of any suitable material, such as but not limited to metals, such as Nitinol, polymers, fabrics and the like. Sleeve 922 may be a solid cylindrical member, or alternatively may have patterned cut-outs, like a stent, or be made of ribbed, woven, braided, porous, nonporous or any other suitable material, pattern, configuration or the like. Sleeve 920 may be essentially rigid and axially incompressible, while in other embodiments it may be axially compressible. In one embodiment, sleeve 920 may be configured as two rings, disposed adjacent two anchors 922, with the rings being connected by a rod or shaft, so that tether 924 is not encircled by the sleeve 922.

Figure 19B:
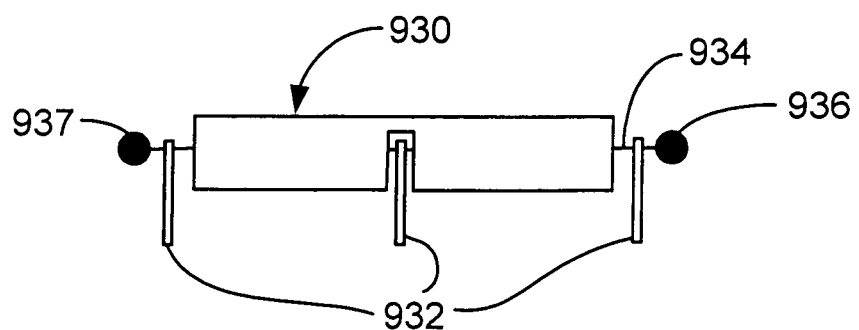
FIG. 19B shows an anchor device having a sleeve between three anchors according to one embodiment of the invention.

With reference now to FIG. 19B, in an alternative embodiment, a sleeve 930 may be disposed over a tether 934 so as to extend between more than two anchors 932. Such a sleeve 930 may thus distribute force applied between a termination member 936 and a force applying member 937 so as to help prevent anchor pull-out from tissue. Such a sleeve 930 may include one or more openings through which one or more middle anchors may extend. Again, sleeve 930 may have any suitable configuration, size, shape or the like and be made of any suitable material or combination of materials. Sleeve 930 may extend between three, four, five or any suitable number of anchors 932 in various embodiments. In an alternative embodiment, sleeve 930 may be pierced by one or more of the anchors 932 and thus attached to valve annulus tissue.

Although the foregoing is a complete and accurate description of the present invention, the description provided above is for exemplary purposes only, and variations may be made to the embodiments described without departing from the scope of the invention. Thus, the above description should not be construed to limit the scope of the invention as described in the appended claims.

What is claimed is:

1. A method for advancing an operational device into a left ventricle of a heart to contact ventricular wall tissue comprising:
   advancing an operational device into a left ventricle and circumferentially along at least a portion of the ventricular wall tissue at or adjacent to a mitral valve having leaflets, the operational device comprising a plurality of side wall openings facing the tissue below the leaflets;
   acting on the ventricular wall tissue by securing a series of anchors at or adjacent to the mitral valve, wherein the series of anchors are delivered through the plurality of side wall openings such that each anchor engages the tissue on a ventricular side of the heart without penetrating into tissue of a left atrium and wherein the series of anchors are directly coupled to a tether, the tether arranged to travel through the plurality of side wall openings to deliver the series of anchors, wherein the series of anchors comprise a proximal anchor coupled to the tether and a distal anchor secured to the tether and wherein the acting on step comprises pulling on the tether to reduce the distance between the proximal and distal anchors; and
   removing the operational device from the left ventricle.

2. The method according to claim 1 wherein a radius of curvature of the operational device in an expanded state is about 25%-50% larger than a radius of curvature of the mitral valve.

3. The method according to claim 1 wherein the advancing step comprises passing the operational device through the aorta.

4. The method according to claim 1 further comprising urging the operational device radially outwardly to seat the operational device against the ventricular wall tissue at or adjacent to a mitral valve, wherein the distal portion of the operational device is entirely within the ventricle, the urging step being carried out at least in part by virtue of the operational device having a radius of curvature when in an expanded state larger than the radius of curvature of the mitral valve.

5. The method according to claim 4 wherein the urging step further comprises radially outwardly expanding an expansible element associated with the operational device, and wherein the radially outwardly expanding step is carried out with an expansible element having a radius larger than the radius of the operational device.

6. The method according to claim 4 wherein the urging step further comprises radially outwardly expanding a balloon associated with the operational device.

7. The method according to claim 4 wherein the urging step is carried out:
   with an operational device having a length; and
   to seat the entire length of the operational device against the ventricular wall at or adjacent to the mitral valve.

8. The method according to claim 1 wherein the operational device advancing step is carried out using a steerable operational device.

9. The method according to claim 1 wherein the operational device advancing step comprises:
   advancing a guide catheter into a left ventricle and along at least a portion of the ventricular wall at or adjacent to the mitral valve;
   passing a flexible guide sheath over the guide catheter and along at least a portion of the ventricular wall at or adjacent to the mitral valve; and
   advancing the operational device through the guide sheath.

10. The method according to claim 9 further comprising withdrawing the guide catheter from the guide sheath before advancing the operational device through the guide sheath.

11. The method according to claim 9 further comprising removing the guide sheath from the ventricular wall at or adjacent to the mitral valve before the acting on step.

12. The method according to claim 9 wherein the guide catheter advancing step is carried out using a steerable guide catheter.

13. The method according to claim 1 wherein the acting on step is carried out using self-forming anchors.

14. The method according to claim 1 wherein the advancing step comprises advancing the operational device through a guide sheath.

15. The method according to claim 14 wherein the acting on step comprises delivering the anchors from a housing of the operational device, through a distal portion of the guide sheath and into the ventricular wall tissue at or adjacent to the mitral valve thereby attaching the distal portion of the guide sheath to the ventricular wall.

16. A method for advancing an operational device into a left ventricle of a heart to contact ventricular wall tissue comprising:
   advancing an operational device into a left ventricle and circumferentially along at least a portion of the ventricular wall tissue at or adjacent to a mitral valve having leaflets, the operational device comprising a plurality of side wall openings facing the tissue below the leaflets;
   acting on the ventricular wall tissue by securing a series of anchors at or adjacent to the mitral valve, wherein the series of anchors are delivered through the plurality of side wall openings such that each anchor engages the tissue on a ventricular side of the heart without penetrating into tissue of a left atrium and wherein the series of anchors are directly coupled to a tether, the tether arranged to travel through the plurality of side wall openings to deliver the series of anchors, wherein the series of anchors comprise a proximal anchor coupled to the tether and a distal anchor secured to the tether and wherein the acting on step comprises pulling on the tether to reduce the distance between the proximal and distal anchors; and
   removing the operational device from the left ventricle; and wherein:
   the advancing step is carried out using an operational device comprising: an elongate housing having a longitudinal axis and an open interior;
   wherein the series of anchors comprise tissue-engageable anchors, the anchors located within the open interior of the housing; each anchor having a first part and a second part, the second part having a tissue piercing tip, wherein the side wall openings are located in the housing and are sized for passage of the anchor tip-first through the openings;

each anchor placeable in a relatively straight, undeployed state generally parallel to the longitudinal axis within the housing; and the acting on step further comprises driving the anchors tip-first through the side wall openings with the anchors naturally assuming a curved, tissue-engaging deployed state after passing through the openings in the housing.

17. The method according to claim 16 wherein the advancing step is carried out using an anchor comprising said first part and two of said second part extending from the first part.

18. The method according to claim 17 wherein the second parts extend in directions generally opposite one another when in the deployed state.

19. The method according to claim 17 wherein the second parts have generally circular or semicircular shapes when in the deployed state.

20. The method according to claim 16 wherein each anchor is oriented generally perpendicular to the longitudinal axis when in the deployed state.

21. The method according to claim 16 wherein each anchor has a generally circular or semicircular shape when in the deployed state.

22. A method for advancing an operational device into a left ventricle of a heart to contact ventricular wall tissue comprising:

advancing an operational device into a left ventricle and circumferentially along at least a portion of the ventricular wall tissue at or adjacent to a mitral valve having leaflets, the operational device comprising a plurality of side wall openings facing the tissue below the leaflets;

acting on the ventricular wall tissue by securing a series of anchors at or adjacent to the mitral valve, wherein the series of anchors are delivered through the plurality of side wall openings such that each anchor engages the tissue on a ventricular side of the heart without penetrating into tissue of a left atrium and wherein the series of anchors are directly coupled to a tether, the tether arranged to travel through the plurality of side wall openings to deliver the series of anchors, and wherein the acting on step further comprises delivering the series of coupled anchors from a housing of the operational device into the ventricular wall tissue at or adjacent to the mitral valve and circumferentially tightening the mitral valve by placing the tether in tension; and removing the operational device from the left ventricle.

23. The method according to claim 22 wherein the anchors delivering step comprises driving at least one of the anchors through a biocompatible material thereby attaching the biocompatible material to the ventricular wall at or adjacent to the mitral valve.

24. The method according to claim 23 wherein the anchor delivering step is carried out using a strip of the biocompatible material and the anchors driving step comprises driving a plurality of the anchors through the strip of biocompatible material.

25. The method according to claim 23 wherein the anchor delivering step is carried out using a plurality of pieces of the biocompatible material and the anchors driving step comprises driving a plurality of the anchors through the pieces of biocompatible material.

26. A method for advancing an operational device into a left ventricle of a heart to contact ventricular wall tissue comprising:

advancing an operational device into a left ventricle and along at least a portion of the ventricular wall tissue at or adjacent to a mitral valve having leaflets, the operational device comprising an expansible element and comprising a plurality of side wall openings facing the tissue below the leaflets;

the operational device advancing step comprising steering the operational device circumferentially around the mitral valve, along the ventricular wall, wherein the distal portion of the operational device is entirely within the ventricle; radially outwardly expanding the expansible element to urge the operational device radially outwardly to seat the operational device against the ventricular wall at or adjacent to the mitral valve;

acting on the ventricular wall tissue by securing a series of anchors at or adjacent to the mitral valve, wherein the series of anchors are delivered through the plurality of side wall openings such that the each anchor engages the tissue on a ventricular side of the heart without penetrating into tissue of a left atrium and wherein the series of anchors are directly coupled to a tether, the tether arranged to travel through the plurality of side wall openings to deliver the series of anchors, wherein the series of anchors comprise a proximal anchor coupled to the tether and a distal anchor secured to the tether, and the acting on step comprises pulling on the tether to reduce the distance between the proximal and distal anchors; and removing the operational device from the left ventricle.

27. The method according to claim 26 wherein the advancing step comprises passing the operational device through the aorta.

28. The method according to claim 26 wherein the expansible element has a radius larger than the radius of the operational device.

29. The method according to claim 26 wherein the urging step is carried out with a balloon as the expansible element.

30. The method according to claim 26 wherein the acting on step is carried out using self-forming anchors.

31. The method according to claim 26 wherein the acting on step comprises delivering the anchors from a housing of the operational device into ventricular wall tissue at or adjacent to the mitral valve.

32. The method according to claim 26 wherein the advancing step is carried out using the operational device as the only steerable element.

33. A method for advancing an operational device into a left ventricle of a heart to contact ventricular wall tissue comprising:

advancing an operational device into a left ventricle and along at least a portion of the ventricular wall tissue at or adjacent to a mitral valve having leaflets, the operational device comprising an expansible element and comprising a plurality of side wall openings facing the tissue below the leaflets;

the operational device advancing step comprising steering the operational device circumferentially around the mitral valve, along the ventricular wall, wherein the distal portion of the operational device is entirely within the ventricle; radially outwardly expanding the expansible element to urge the operational device radially outwardly to seat the operational device against the ventricular wall at or adjacent to the mitral valve;

acting on the ventricular wall tissue by securing a series of anchors at or adjacent to the mitral valve, wherein the series of anchors are delivered through the plurality of side wall openings such that the each anchor engages the tissue on a ventricular side of the heart without penetrating into tissue of a left atrium and wherein the series of anchors are directly coupled to a tether, the tether arranged to travel through the plurality of side wall openings to deliver the series of anchors, wherein the acting on step further comprises circumferentially tightening the mitral valve by placing the tether in tension; and removing the operational device from the left ventricle.

34. A method for advancing an operational device into a left ventricle of a heart to contact ventricular wall tissue comprising:

advancing a guide catheter into a left ventricle and circumferentially along at least a portion of the ventricular wall tissue at or adjacent to a mitral valve, the mitral valve having leaflets and a mitral valve radius;

selecting a flexible guide sheath having a curveable portion, said curveable portion having a guide sheath radius when in an outwardly expanded curved state, the guide sheath radius being larger than the mitral valve radius;

passing the guide sheath over the guide catheter and along at least a portion of the ventricular wall tissue at or adjacent to the mitral valve;

advancing an operational device through the guide sheath, the operational device comprising a plurality of side wall openings facing the tissue below the leaflets, wherein the distal portion of the operational device is entirely within the ventricle;

acting on the ventricular wall tissue by securing a series of anchors at or adjacent to the mitral valve, wherein the series of anchors are delivered through the plurality of side wall openings such that each anchor engages the tissue on a ventricular side of the heart without penetrating into tissue of a left atrium and wherein the series of anchors are directly coupled to a tether, the tether arranged to travel through the plurality of side wall openings to deliver the series of anchors, wherein the series of anchors comprise a proximal anchor coupled to the tether and a distal anchor secured to the tether, and wherein the acting on step further comprises pulling on the tether to reduce the distance between the proximal and distal anchors; and removing the operational device from the left ventricle.

35. The method according to claim 34 wherein the guide sheath radius is about 25%-50% larger than the mitral valve radius.

36. The method according to claim 34 wherein the guide catheter advancing step is carried out using a steerable guide catheter.

37. The method according to claim 34 further comprising withdrawing the guide catheter from the guide sheath before the operational device advancing step.

38. The method according to claim 34 further comprising removing the guide sheath from the ventricular wall at or adjacent to the mitral valve before the acting on step.

39. The method according to claim 34 wherein the acting on step comprises urging the operational device radially outwardly to engage the ventricular wall tissue at or adjacent to the mitral valve.

40. The method according to claim 34 wherein the acting on step is carried out using self-forming anchors.

41. A method for advancing an operational device into a left ventricle of a heart to contact ventricular wall tissue comprising:

selecting a flexible guide catheter having a curveable portion, said curveable portion having a guide catheter radius when in outwardly expanded curved state;

advancing the guide catheter into a left ventricle and circumferentially along at least a portion of the ventricular wall tissue at or adjacent to a mitral valve, the mitral valve having leaflets and a mitral valve radius;

the selecting step being carried out with the guide catheter radius being larger than the mitral valve radius;

passing a curveable portion of a guide sheath over the guide catheter and along at least a portion of the ventricular wall tissue at or adjacent to the mitral valve;

advancing an operational device through the guide sheath, the operational device comprising a plurality of side wall openings facing the tissue below the leaflets, wherein the distal portion of the operational device is entirely within the ventricle;

acting on the ventricular wall tissue by securing a series of anchors at or adjacent to the mitral valve, wherein the series of anchors are delivered through the plurality of side wall openings such that each anchor engages the tissue on a ventricular side of the heart without penetrating into tissue of a left atrium and wherein the series of anchors are directly coupled to a tether, the tether arranged to travel through the plurality of side wall openings to deliver the series of anchors, wherein the series of anchors comprise a proximal anchor coupled to the tether and a distal anchor secured to the tether, and wherein the acting on step comprises pulling on the tether to reduce the distance between the proximal and distal anchors; and removing the operational device from the left ventricle.

42. The method according to claim 41 wherein the guide catheter radius is about 25%-50% larger than the mitral valve radius.

43. The method according to claim 41 wherein the guide catheter advancing step is carried out using a steerable guide catheter.

44. The method according to claim 41 further comprising withdrawing the guide catheter from the guide sheath before the operational device advancing step.

45. The method according to claim 41 further comprising removing the guide sheath from the ventricular wall at or adjacent to the mitral valve before the acting on step.

46. The method according to claim 41 wherein the acting on step comprises urging the operational device radially outwardly to engage the ventricular wall at or adjacent to the mitral valve.

47. The method according to claim 41 wherein the acting on step is carried out using self-forming anchors.

* * * * *